US008420596B2

(12) United States Patent
Ku et al.

(10) Patent No.: US 8,420,596 B2
(45) Date of Patent: Apr. 16, 2013

(54) MACROCYCLIC HEPATITIS C SERINE PROTEASE INHIBITORS

(75) Inventors: Yiyin Ku, Buffalo Grove, IL (US); Keith F. McDaniel, Wauconda, IL (US); Hui-Ju Chen, Grayslake, IL (US); Jason P. Shanley, Chicago, IL (US); Dale J. Kempf, Libertyville, IL (US); David J. Grampovnik, Waukegan, IL (US)

(73) Assignees: Abbott Laboratories, Abbott Park, IL (US); Enanta Pharmaceuticals, Inc., Watertown, MA (US)

( * ) Notice: Subject to any disclaimer, the term of this patent is extended or adjusted under 35 U.S.C. 154(b) by 577 days.

(21) Appl. No.: 12/584,716

(22) Filed: Sep. 10, 2009

(65) Prior Publication Data

US 2010/0144608 A1    Jun. 10, 2010

Related U.S. Application Data

(60) Provisional application No. 61/191,725, filed on Sep. 11, 2008, provisional application No. 61/209,689, filed on Mar. 10, 2009.

(51) Int. Cl.
   *A61K 38/00*    (2006.01)
(52) U.S. Cl.
   USPC .......................................................... 514/3.7
(58) Field of Classification Search ........................ None
   See application file for complete search history.

(56) References Cited

U.S. PATENT DOCUMENTS

| 5,831,002 | A  | 11/1998 | Haupt et al. |
| 6,268,207 | B1 | 7/2001  | Bailey |
| 6,323,180 | B1 | 11/2001 | Llinas-Brunet et al. |
| 6,329,379 | B1 | 12/2001 | Llinas-Brunet et al. |
| 6,329,417 | B1 | 12/2001 | Llinas-Brunet et al. |
| 6,410,531 | B1 | 6/2002  | Llinas-Brunet et al. |
| 6,420,380 | B2 | 7/2002  | Llinas-Brunet et al. |
| 6,534,523 | B1 | 3/2003  | Llinas-Brunet et al. |
| 6,608,027 | B1 | 8/2003  | Tsantrizos et al. |
| 6,642,204 | B2 | 11/2003 | Llinas-Brunet et al. |
| 6,653,295 | B2 | 11/2003 | Glunz et al. |
| 6,699,855 | B2 | 3/2004  | Zhang et al. |
| 6,727,366 | B2 | 4/2004  | Han et al. |
| 6,767,991 | B1 | 7/2004  | Llinas-Brunet et al. |
| 6,774,212 | B2 | 8/2004  | Han |
| 6,803,374 | B2 | 10/2004 | Priestley et al. |
| 6,846,806 | B2 | 1/2005  | Priestley |
| 6,867,185 | B2 | 3/2005  | Campbell et al. |
| 6,869,964 | B2 | 3/2005  | Campbell et al. |
| 6,872,805 | B2 | 3/2005  | Campbell et al. |
| 6,878,722 | B2 | 4/2005  | Campbell et al. |
| 6,939,854 | B2 | 9/2005  | Priestley |
| 6,995,174 | B2 | 2/2006  | Wang et al. |
| 7,037,911 | B2 | 5/2006  | Zhang |
| 7,041,698 | B2 | 5/2006  | Ripka et al. |
| 7,091,184 | B2 | 8/2006  | Llinas-Brunet et al. |
| 7,112,601 | B2 | 9/2006  | Glunz et al. |
| 7,119,072 | B2 | 10/2006 | Llinas-Brunet et al. |
| 7,122,627 | B2 | 10/2006 | Priestley et al. |
| 7,132,504 | B2 | 11/2006 | Scola et al. |
| 7,135,462 | B2 | 11/2006 | Scola et al. |
| 7,153,848 | B2 | 12/2006 | Hudyma et al. |
| 7,157,424 | B2 | 1/2007  | Chen et al. |
| 7,173,004 | B2 | 2/2007  | McPhee et al. |
| 7,176,208 | B2 * | 2/2007 | Nakajima et al. ........ 514/255.05 |
| 7,183,302 | B2 | 2/2007  | Romine et al. |
| 7,189,844 | B2 | 3/2007  | Gallou et al. |
| 7,309,708 | B2 | 12/2007 | Tu et al. |
| 7,323,447 | B2 | 1/2008  | Sin et al. |
| 7,348,425 | B2 | 3/2008  | Hudyma et al. |
| 7,368,452 | B2 | 5/2008  | Nakajima et al. |
| 7,375,218 | B2 | 5/2008  | Gallou |
| 7,491,794 | B2 | 2/2009  | Blatt et al. |
| 7,504,378 | B2 | 3/2009  | Llinas-Brunet et al. |
| 7,544,798 | B2 | 6/2009  | Busacca et al. |
| 7,566,719 | B2 | 7/2009  | Nakajima et al. |
| 7,592,419 | B2 | 9/2009  | Venkatraman et al. |
| 7,601,709 | B2 | 10/2009 | Miao et al. |
| 7,608,590 | B2 | 10/2009 | Rosenquist et al. |
| 7,642,235 | B2 | 1/2010  | Llinas-Brunet et al. |
| 7,642,339 | B2 | 1/2010  | Chaudhary et al. |
| 7,659,245 | B2 | 2/2010  | Simmen et al. |
| 7,687,459 | B2 | 3/2010  | Niu et al. |
| 7,741,281 | B2 | 6/2010  | D'Andrea et al. |
| 7,763,584 | B2 | 7/2010  | Wang et al. |
| 7,772,180 | B2 | 8/2010  | Sin et al. |
| 7,772,183 | B2 | 8/2010  | Carini et al. |
| 7,829,665 | B2 | 11/2010 | Blatt et al. |
| 2002/0016442 | A1 | 2/2002 | Llinas-brunet et al. |
| 2002/0037998 | A1 | 3/2002 | Llinas-Brunet et al. |
| 2002/0111313 | A1 | 8/2002 | Campbell et al. |
| 2003/0181363 | A1 | 9/2003 | Llinas-Brunet et al. |
| 2003/0186895 | A1 | 10/2003 | Llinas-Brunet et al. |
| 2003/0187018 | A1 | 10/2003 | Llinas-Brunet et al. |
| 2003/0191067 | A1 | 10/2003 | Llinas-Brunet et al. |
| 2003/0224977 | A1 | 12/2003 | Llinas-Brunet et al. |

(Continued)

FOREIGN PATENT DOCUMENTS

EP    1169339 A1    1/2002
EP    1437362 A1    7/2004

(Continued)

OTHER PUBLICATIONS

Ettmayer P. et al. J. Med. Chem. (2004) 47(10), pp. 2393-2404.*

(Continued)

*Primary Examiner* — Thomas Heard
(74) *Attorney, Agent, or Firm* — Edwards Wildman Palmer LLP; Jeffrey D. Hsi; Mark D. Russett

(57) ABSTRACT

The present invention relates to novel macrocyclic compounds and methods of treating a hepatitis C infection in a subject in need of such therapy with said macrocyclic compounds. The present invention further relates to pharmaceutical compositions comprising the compounds of the present invention, or pharmaceutically acceptable salts, esters, or prodrugs thereof, in combination with a pharmaceutically acceptable carrier or excipient.

20 Claims, No Drawings

U.S. PATENT DOCUMENTS

| | | |
|---|---|---|
| 2003/0232386 A1 | 12/2003 | Shah et al. |
| 2004/0002448 A1 | 1/2004 | Tsantrizos et al. |
| 2004/0038872 A1 | 2/2004 | Campbell et al. |
| 2004/0048802 A1 | 3/2004 | Ripka et al. |
| 2004/0058982 A1 | 3/2004 | Harris |
| 2004/0106559 A1 | 6/2004 | Wang et al. |
| 2004/0180815 A1 | 9/2004 | Nakajima et al. |
| 2004/0229776 A1 | 11/2004 | Chen et al. |
| 2004/0229777 A1 | 11/2004 | Cerreta et al. |
| 2004/0229818 A1 | 11/2004 | Llinas-Brunet |
| 2004/0248779 A1 | 12/2004 | Dersch et al. |
| 2004/0248806 A1 | 12/2004 | Temsamani et al. |
| 2004/0266668 A1 | 12/2004 | Nakajima et al. |
| 2005/0020503 A1 | 1/2005 | Llinas-Brunet et al. |
| 2005/0049187 A1 | 3/2005 | Brandenburg et al. |
| 2005/0075279 A1 | 4/2005 | Llinas-Brunet et al. |
| 2005/0080005 A1 | 4/2005 | Llinas-Brunet et al. |
| 2005/0090432 A1 | 4/2005 | McPhee et al. |
| 2005/0119168 A1 | 6/2005 | Venkatraman et al. |
| 2005/0143316 A1 | 6/2005 | Tu et al. |
| 2005/0148085 A1 | 7/2005 | Larsen |
| 2005/0153877 A1 | 7/2005 | Miao et al. |
| 2005/0153900 A1 | 7/2005 | Velazquez et al. |
| 2005/0164921 A1 | 7/2005 | Njoroge et al. |
| 2005/0192212 A1 | 9/2005 | Llinas-Brunet et al. |
| 2005/0209135 A1 | 9/2005 | Busacca et al. |
| 2005/0214366 A1 | 9/2005 | Harris |
| 2005/0215423 A1 | 9/2005 | Brenner et al. |
| 2005/0222045 A1 | 10/2005 | Auvin et al. |
| 2005/0267018 A1 | 12/2005 | Blatt et al. |
| 2005/0267151 A1 | 12/2005 | Busacca et al. |
| 2006/0009667 A1 | 1/2006 | Herweck et al. |
| 2006/0019905 A1 | 1/2006 | Bailey et al. |
| 2006/0046965 A1 | 3/2006 | Bailey et al. |
| 2006/0063915 A1 | 3/2006 | Gallou et al. |
| 2006/0063916 A1 | 3/2006 | Gallou |
| 2006/0068007 A1 | 3/2006 | Li et al. |
| 2006/0089300 A1 | 4/2006 | Llinas-Brunet et al. |
| 2006/0122123 A1 | 6/2006 | Chaudhary et al. |
| 2006/0166893 A1 | 7/2006 | Auvin et al. |
| 2006/0172950 A1 | 8/2006 | Wang et al. |
| 2006/0199773 A1 | 9/2006 | Sausker et al. |
| 2006/0205638 A1 | 9/2006 | Busacca et al. |
| 2006/0257980 A1 | 11/2006 | Li |
| 2006/0258868 A1 | 11/2006 | Bailey et al. |
| 2006/0275366 A1 | 12/2006 | Malcolm et al. |
| 2006/0276405 A1 | 12/2006 | Albrecht |
| 2006/0276407 A1 | 12/2006 | Albrecht et al. |
| 2006/0281688 A1 | 12/2006 | Zhang et al. |
| 2007/0004635 A1 | 1/2007 | Albrecht et al. |
| 2007/0010431 A1 | 1/2007 | Malcolm et al. |
| 2007/0010455 A1 | 1/2007 | Hewawasam et al. |
| 2007/0060510 A1 | 3/2007 | Nakajima et al. |
| 2007/0060565 A1 | 3/2007 | Meanwell et al. |
| 2007/0072809 A1 | 3/2007 | Cho et al. |
| 2007/0078081 A1 | 4/2007 | Casarez et al. |
| 2007/0078122 A1 | 4/2007 | Bergstrom et al. |
| 2007/0093414 A1 | 4/2007 | Carini et al. |
| 2007/0099825 A1 | 5/2007 | D'Andrea et al. |
| 2007/0161575 A1 | 7/2007 | Miao et al. |
| 2007/0179167 A1 | 8/2007 | Cottrell et al. |
| 2007/0184024 A1 | 8/2007 | Meanwell et al. |
| 2007/0185083 A1 | 8/2007 | Bergstrom et al. |
| 2007/0237818 A1 | 10/2007 | Malcolm et al. |
| 2007/0243166 A1 | 10/2007 | Llinas-Brunet et al. |
| 2007/0249637 A1 | 10/2007 | Collins et al. |
| 2007/0258947 A1 | 11/2007 | Njoroge et al. |
| 2007/0270405 A1 | 11/2007 | Bender et al. |
| 2007/0270406 A1 | 11/2007 | Gentles et al. |
| 2007/0275930 A1 | 11/2007 | Gentles et al. |
| 2007/0281884 A1 | 12/2007 | Sun et al. |
| 2007/0281885 A1 | 12/2007 | Sun et al. |
| 2007/0287664 A1 | 12/2007 | Ralston et al. |
| 2007/0287694 A1 | 12/2007 | Yeung et al. |
| 2007/0299078 A1 | 12/2007 | Niu et al. |
| 2008/0008681 A1 | 1/2008 | Niu et al. |
| 2008/0014173 A1 | 1/2008 | Scola et al. |
| 2008/0032936 A1 | 2/2008 | Gai et al. |
| 2008/0038225 A1 | 2/2008 | Sun et al. |
| 2008/0039375 A1 | 2/2008 | Moore et al. |
| 2008/0039470 A1 | 2/2008 | Niu et al. |
| 2008/0045536 A1 | 2/2008 | Vaccaro et al. |
| 2008/0107623 A1 | 5/2008 | D'Andrea et al. |
| 2008/0107624 A1 | 5/2008 | D'Andrea et al. |
| 2008/0107625 A1 | 5/2008 | D'Andrea et al. |
| 2008/0108632 A1 | 5/2008 | Lin et al. |
| 2008/0119461 A1 | 5/2008 | Sin et al. |
| 2008/0145334 A1 | 6/2008 | Wang et al. |
| 2008/0146537 A1 | 6/2008 | Bender et al. |
| 2008/0152619 A1 | 6/2008 | Sin et al. |
| 2008/0152622 A1 | 6/2008 | Nakajima et al. |
| 2008/0159982 A1 | 7/2008 | Wang et al. |
| 2008/0171015 A1 | 7/2008 | Bender et al. |
| 2008/0181868 A1 | 7/2008 | Sun et al. |
| 2008/0200497 A1 | 8/2008 | Bailey et al. |
| 2008/0242835 A1 | 10/2008 | Shu |
| 2008/0267916 A1 | 10/2008 | Gai et al. |
| 2008/0267917 A1 | 10/2008 | Niu et al. |
| 2008/0269228 A1 | 10/2008 | Moore et al. |
| 2008/0269502 A1 | 10/2008 | Gantz et al. |
| 2008/0279821 A1 | 11/2008 | Niu et al. |
| 2008/0311077 A1 | 12/2008 | Chaudhary et al. |
| 2009/0005387 A1 | 1/2009 | Niu et al. |
| 2009/0035271 A1 | 2/2009 | Sun et al. |
| 2009/0036708 A1 | 2/2009 | Jia et al. |
| 2009/0041721 A1 | 2/2009 | Niu et al. |
| 2009/0047252 A1 | 2/2009 | Cai et al. |
| 2009/0075869 A1 | 3/2009 | Holloway et al. |
| 2009/0093533 A1 | 4/2009 | Beigelman et al. |
| 2009/0105471 A1 | 4/2009 | Blatt et al. |
| 2009/0111757 A1 | 4/2009 | Lin et al. |
| 2009/0111969 A1 | 4/2009 | Blatt et al. |
| 2009/0111982 A1 | 4/2009 | Blatt et al. |
| 2009/0124808 A1 | 5/2009 | Busacca et al. |
| 2009/0130059 A1 | 5/2009 | Sun et al. |
| 2009/0148407 A1 | 6/2009 | Blatt et al. |
| 2009/0149491 A1 | 6/2009 | Liu et al. |
| 2009/0155209 A1 | 6/2009 | Blatt et al. |
| 2009/0162318 A1 | 6/2009 | Bender et al. |
| 2009/0163706 A1 | 6/2009 | Hildbrand et al. |
| 2009/0169510 A1 | 7/2009 | Blatt et al. |
| 2009/0175822 A1 | 7/2009 | Moore et al. |
| 2009/0176858 A1 | 7/2009 | Niu et al. |
| 2009/0180981 A1 | 7/2009 | Niu et al. |
| 2009/0186869 A1 | 7/2009 | Cottell et al. |
| 2009/0191153 A1 | 7/2009 | Sun et al. |
| 2009/0202480 A1 | 8/2009 | Parsy et al. |
| 2009/0257978 A1 | 10/2009 | Cho et al. |
| 2009/0269305 A1 | 10/2009 | Seiwert et al. |
| 2009/0274648 A1 | 11/2009 | Wang et al. |
| 2009/0274652 A1 | 11/2009 | Sin et al. |
| 2009/0281141 A1 | 11/2009 | Simmen et al. |
| 2009/0285773 A1 | 11/2009 | Sun et al. |
| 2009/0285774 A1 | 11/2009 | Sin et al. |
| 2009/0286814 A1 | 11/2009 | Lin et al. |
| 2009/0286843 A1 | 11/2009 | Blatt et al. |
| 2009/0297472 A1 | 12/2009 | Wang et al. |
| 2009/0304626 A1 | 12/2009 | Wang et al. |
| 2009/0304629 A1 | 12/2009 | Miao et al. |
| 2009/0306085 A1 | 12/2009 | Petter et al. |
| 2009/0326194 A1 | 12/2009 | Busacca et al. |
| 2010/0015092 A1 | 1/2010 | Nakajima et al. |
| 2010/0018355 A1 | 1/2010 | Crawford |
| 2010/0022578 A1 | 1/2010 | Raboisson et al. |
| 2010/0028300 A1 | 2/2010 | Llinas-Brunet et al. |
| 2010/0036116 A1 | 2/2010 | Scalone et al. |
| 2010/0041591 A1 | 2/2010 | Niu et al. |
| 2010/0041728 A1 | 2/2010 | Antonov et al. |
| 2010/0068182 A1 | 3/2010 | Huang et al. |
| 2010/0069294 A1 | 3/2010 | Petter et al. |
| 2010/0074890 A1 | 3/2010 | Hagel et al. |
| 2010/0080770 A1 | 4/2010 | Hiebert et al. |
| 2010/0080771 A1 | 4/2010 | Hiebert et al. |
| 2010/0081700 A1 | 4/2010 | Wang et al. |
| 2010/0081713 A1 | 4/2010 | Sharma et al. |
| 2010/0093792 A1 | 4/2010 | Berkenbusch et al. |
| 2010/0099695 A1 | 4/2010 | Liverton et al. |

| | | | |
|---|---|---|---|
| 2010/0113440 A1 | 5/2010 | Belfrage et al. | |
| 2010/0124545 A1 | 5/2010 | Zhang et al. | |
| 2010/0144608 A1 | 6/2010 | Ku et al. | |
| 2010/0150866 A1 | 6/2010 | Wang et al. | |
| 2010/0160403 A1 | 6/2010 | Link et al. | |
| 2010/0168384 A1 | 7/2010 | Mcdaniel et al. | |
| 2010/0196321 A1 | 8/2010 | Cooper et al. | |
| 2010/0240698 A1 | 9/2010 | Simmen et al. | |
| 2010/0260710 A1 | 10/2010 | Parsy et al. | |
| 2010/0272674 A1 | 10/2010 | Hiebert et al. | |
| 2010/0292219 A1 | 11/2010 | Agarwal et al. | |
| 2010/0297079 A1 | 11/2010 | Almond et al. | |
| 2011/0020272 A1 | 1/2011 | Schubert | |
| 2011/0059047 A1 | 3/2011 | Seiwert et al. | |
| 2011/0065737 A1 | 3/2011 | Liu et al. | |
| 2011/0178107 A1 | 7/2011 | Wang et al. | |

FOREIGN PATENT DOCUMENTS

| | | | |
|---|---|---|---|
| EP | 1472278 A2 | 11/2004 | |
| EP | 1455809 | 6/2011 | |
| WO | WO-96/40751 A1 | 12/1996 | |
| WO | WO-96/40752 A1 | 12/1996 | |
| WO | WO-99/07733 A2 | 2/1999 | |
| WO | WO-00/09543 A2 | 2/2000 | |
| WO | WO-00/09558 A1 | 2/2000 | |
| WO | WO-00/59929 A1 | 10/2000 | |
| WO | WO-02/060926 A2 | 8/2002 | |
| WO | WO-03/053349 A2 | 7/2003 | |
| WO | WO-03/064416 A1 | 8/2003 | |
| WO | WO-03/064455 A2 | 8/2003 | |
| WO | WO-03/064456 A1 | 8/2003 | |
| WO | WO-03/066103 A1 | 8/2003 | |
| WO | WO-03/099274 A1 | 12/2003 | |
| WO | WO-2004/030670 A1 | 4/2004 | |
| WO | WO-2004/037855 A1 | 5/2004 | |
| WO | WO-2004/039833 A1 | 5/2004 | |
| WO | 2004/072243 A2 | 8/2004 | |
| WO | WO-2004/087741 A1 | 10/2004 | |
| WO | WO-2004/089974 A1 | 10/2004 | |
| WO | WO-2004/092203 A2 | 10/2004 | |
| WO | 2004/093798 A2 | 11/2004 | |
| WO | WO 2004/093798 | * 11/2004 | |
| WO | WO-2004/093915 A1 | 11/2004 | |
| WO | WO-2004/094452 A2 | 11/2004 | |
| WO | WO-2004/103996 A1 | 12/2004 | |
| WO | WO-2005/028501 A1 | 3/2005 | |
| WO | WO-2005/037214 A2 | 4/2005 | |
| WO | WO-2005/046712 A1 | 5/2005 | |
| WO | WO-2005/051410 A1 | 6/2005 | |
| WO | WO-2005/051980 A1 | 6/2005 | |
| WO | WO-2005/054430 A2 | 6/2005 | |
| WO | WO-2005/070955 A1 | 8/2005 | |
| WO | WO-2005/075502 A1 | 8/2005 | |
| WO | WO-2005/090383 A2 | 9/2005 | |
| WO | WO-2005/095403 A2 | 10/2005 | |
| WO | WO-2005/116054 A1 | 12/2005 | |
| WO | WO-2006/000085 A1 | 1/2006 | |
| WO | WO-2006/005479 A2 | 1/2006 | |
| WO | WO-2006/020276 A2 | 2/2006 | |
| WO | WO-2006/033851 A2 | 3/2006 | |
| WO | WO-2006/033878 A1 | 3/2006 | |
| WO | WO-2006/036614 A2 | 4/2006 | |
| WO | WO-2006/096652 A2 | 9/2006 | |
| WO | WO-2006/114405 A2 | 11/2006 | |
| WO | WO-2006/119061 A2 | 11/2006 | |
| WO | WO-2006/122188 A2 | 11/2006 | |
| WO | WO-2006/128455 A2 | 12/2006 | |
| WO | WO-2006/130552 A2 | 12/2006 | |
| WO | WO-2006/130553 A2 | 12/2006 | |
| WO | WO-2006/130607 A2 | 12/2006 | |
| WO | WO-2006/130626 A2 | 12/2006 | |
| WO | WO-2006/130627 A2 | 12/2006 | |
| WO | WO-2006/130628 A2 | 12/2006 | |
| WO | WO-2006/130666 A2 | 12/2006 | |
| WO | WO-2006/130686 A2 | 12/2006 | |
| WO | WO-2006/130687 A2 | 12/2006 | |
| WO | WO-2006/130688 A2 | 12/2006 | |
| WO | WO-2007/001406 A2 | 1/2007 | |
| WO | WO-2007/005838 A2 | 1/2007 | |
| WO | WO-2007/008657 A2 | 1/2007 | |
| WO | WO-2007/009109 A2 | 1/2007 | |
| WO | WO-2007/009227 A1 | 1/2007 | |
| WO | 2007/014926 A1 | 2/2007 | |
| WO | WO-2007/014919 A1 | 2/2007 | |
| WO | WO-2007/014921 A1 | 2/2007 | |
| WO | WO-2007/014923 A1 | 2/2007 | |
| WO | WO-2007/014924 A1 | 2/2007 | |
| WO | WO-2007/014925 A1 | 2/2007 | |
| WO | WO-2007/015824 A2 | 2/2007 | |
| WO | WO-2007/016441 A1 | 2/2007 | |
| WO | WO-2007/030656 A1 | 3/2007 | |
| WO | WO-2007/044893 A2 | 4/2007 | |
| WO | WO-2007/044933 A1 | 4/2007 | |
| WO | WO-2007/056120 A1 | 5/2007 | |
| WO | WO-2007/131966 A1 | 11/2007 | |
| WO | WO-2007/139585 A1 | 12/2007 | |
| WO | WO-2007/143694 A2 | 12/2007 | |
| WO | WO-2007/148135 A1 | 12/2007 | |
| WO | WO-2008/002924 A2 | 1/2008 | |
| WO | WO-2008/008502 A1 | 1/2008 | |
| WO | WO-2008/008776 A2 | 1/2008 | |
| WO | WO-2008/019289 | 2/2008 | |
| WO | WO-2008/019289 A2 | 2/2008 | |
| WO | WO-2008/019303 A2 | 2/2008 | |
| WO | WO-2008/021956 A2 | 2/2008 | |
| WO | WO-2008/021960 A2 | 2/2008 | |
| WO | WO-2008/022006 A2 | 2/2008 | |
| WO | WO-2008/039538 A2 | 4/2008 | |
| WO | WO-2008/046860 A2 | 4/2008 | |
| WO | WO-2008/051475 A2 | 5/2008 | |
| WO | WO-2008/051514 A2 | 5/2008 | |
| WO | WO-2008/057208 A2 | 5/2008 | |
| WO | WO-2008/057209 A1 | 5/2008 | |
| WO | WO-2008/057871 A2 | 5/2008 | |
| WO | WO-2008/057873 A2 | 5/2008 | |
| WO | WO-2008/057875 A2 | 5/2008 | |
| WO | WO-2008/057995 A2 | 5/2008 | |
| WO | WO-2008/059046 A1 | 5/2008 | |
| WO | WO-2008/060927 A2 | 5/2008 | |
| WO | WO-2008/062457 A2 | 5/2008 | |
| WO | WO-2008/064057 A1 | 5/2008 | |
| WO | WO-2008/064061 A1 | 5/2008 | |
| WO | WO-2008/064066 A1 | 5/2008 | |
| WO | WO-2008/070733 A2 | 6/2008 | |
| WO | WO-2008/086161 A1 | 7/2008 | |
| WO | WO-2008/092954 A2 | 8/2008 | |
| WO | WO-2008/095058 A1 | 8/2008 | |
| WO | WO-2008/096001 A1 | 8/2008 | |
| WO | WO-2008/098368 A1 | 8/2008 | |
| WO | WO-2008/101665 A1 | 8/2008 | |
| WO | WO-2008/106130 A2 | 9/2008 | |
| WO | WO-2008/114006 A1 | 9/2008 | |
| WO | WO-2008/124384 A2 | 10/2008 | |
| WO | WO-2008/128921 A1 | 10/2008 | |
| WO | WO-2008/137779 A2 | 11/2008 | |
| WO | WO-2008/141227 A1 | 11/2008 | |
| WO | WO-2009/005676 A2 | 1/2009 | |
| WO | WO-2009/005677 A2 | 1/2009 | |
| WO | WO-2009/010804 A1 | 1/2009 | |
| WO | WO-2009/014730 A1 | 1/2009 | |
| WO | WO-2009/053828 A2 | 4/2009 | |
| WO | WO-2009/067108 A1 | 5/2009 | |
| WO | WO-2009/070689 A1 | 6/2009 | |
| WO | WO 2009/070692 A1 | 6/2009 | |
| WO | WO-2009/073713 A1 | 6/2009 | |
| WO | WO-2009/073719 A1 | 6/2009 | |
| WO | WO-2009/073780 A1 | 6/2009 | |
| WO | WO-2009/080542 A1 | 7/2009 | |
| WO | WO-2009/082697 A1 | 7/2009 | |
| WO | WO-2009/082701 A1 | 7/2009 | |
| WO | WO-2009/085659 A1 | 7/2009 | |
| WO | WO-2009/099596 A2 | 8/2009 | |
| WO | WO-2009/129109 A1 | 10/2009 | |
| WO | WO-2009/137432 A1 | 11/2009 | |
| WO | WO-2009/139792 A1 | 11/2009 | |
| WO | WO-2009/140475 A1 | 11/2009 | |
| WO | WO-2009/140500 A1 | 11/2009 | |
| WO | WO-2009/142842 A2 | 11/2009 | |

| WO | WO-2009/146347 A1 | 12/2009 |
| WO | WO-2009/148923 A1 | 12/2009 |
| WO | WO-2009/149377 A1 | 12/2009 |
| WO | WO-2010-000459 A1 | 1/2010 |
| WO | WO-2010/015545 A1 | 2/2010 |
| WO | WO-2010/021717 A2 | 2/2010 |
| WO | WO-2010/028236 A1 | 3/2010 |
| WO | WO-2010/033443 A1 | 3/2010 |
| WO | WO-2010/033444 A1 | 3/2010 |
| WO | WO-2010/033466 A1 | 3/2010 |
| WO | WO-2010/034105 A1 | 4/2010 |
| WO | WO-2010/036551 A1 | 4/2010 |
| WO | WO-2010/036871 A1 | 4/2010 |
| WO | WO-2010/036896 A1 | 4/2010 |
| WO | WO-2010/042834 A1 | 4/2010 |
| WO | WO-2010/048468 A1 | 4/2010 |
| WO | WO-2010/059667 A1 | 5/2010 |
| WO | WO-2010/059937 A1 | 5/2010 |
| WO | WO-2010/065577 A1 | 6/2010 |
| WO | WO-2010/077783 A1 | 7/2010 |
| WO | WO-2010/080389 A1 | 7/2010 |
| WO | WO-2010/088394 A1 | 8/2010 |
| WO | WO-2010/118078 A1 | 10/2010 |
| WO | WO-2010/120476 A2 | 10/2010 |
| WO | WO-2010/128521 A2 | 11/2010 |
| WO | WO-2010/135520 A1 | 11/2010 |
| WO | WO-2010/135748 A1 | 11/2010 |
| WO | WO-2011/017389 A1 | 2/2011 |
| WO | WO-2011/063501 A1 | 6/2011 |
| WO | WO-2011/063502 A1 | 6/2011 |

OTHER PUBLICATIONS

Singh, Yashveer et al, "Recent Trends in Targeted Anticancer Prodrug and Conjugate," DesignCurr Med Chem. 2008; 15(18): 1802-1826.*
Muller, Christa E. "Prodrug Approaches for Enhancing the Bioavailability of Drugs with Low Solubility," Chemistry & Biodiversity, vol. 6 (2009), pp. 2071-2083.*
Beaumont, et, al "Design of Ester Prodrugs to Enhance Oral Absorption of Poorly Permeable Compounds: Challenges to the Discovery Scientist," Current Drug Metabolism, 2003, 4, 461-485.*
Han, H.-K.. AAPS Pharmsci. (2000) 2(1), Article 6, pp. 1-11.*
Testa Prodrug research: futile or fertile? Biochemical Pharmacology (2004) 2097-2106.*
P. Ettmayer et al., J. Med. Chem., 47(10), pp. 2393-2404 (2004).
Y. Singh et al., "Recent Trends in targeted Anticancer Prodrug and Conjugate", DesignCurr Med. Chem., 15(18), pp. 1802-1826 (2008).
C.E. Muller et al., "Prodrug Approaches for Enhancing the Bioavailability of Drugs with Low Solubility", Chemistry & Biodiversity, vol. 6, pp. 2071-2083(2009).

Beaumont et al., "Design of Ester Prodrugs to Enhance Oral Absorption of Poorly Permeable Compounds: Challenges to the Discovery Scientist", Current Drug Metabolism, vol. 4, pp. 461-485 (2003).
H.K. Han et al., AAPS Pharmsci.—Article 6 2(1), pp. 1-11 (2000).
Testa et al., "Prodrug Research: Futile or Fertile?", Biochemical Pharmacology, pp. 2097-2106 (2004).
R. Ronn et al., "Exploration of acyl sulfonamides as carboxylic acid replacements in protease inhibitors of the hepatitis C virus full-length NS3", Bioorganic & Medicinal Chemistry, vol. 14, pp. 544-559 (2006).
International Search Report for corresponding PCT International Application No. PCT/US09/05082 dated Apr. 1, 2010.
Lu, Liangjun, et al.: "Mutations Conferring Resistance to a Potent Hepatitis C Virus Serine Protease Inhibitor in Vitro," Antimicrobial Agents and Chemotherapy, Jun. 2004, vol. 48, No. 6, pp. 2260-2266.
A. Johansson et al., "Acyl Sulfonamides as Potent protease Inhibitors of the Hepatitis C Virus Full-Length NS3 (Protease-Helicase/NTPase): A Comparative Study of Different C-Terminals", Bioorganic & Medicinal Chemistry, vol. 11, pp. 2551-2568 (2003).
N. Goudreau et al., "NMR Structural Characterization of Peptide Inhibitors Bound to the Hepatitis C Virus NS3 Protease: Design of a New P2 Substituent", J. Med. Chem., vol. 47, pp. 123-132 (2004).
N. Goudreau et al., "The terapeutic potential of NS3 protease inhibitors in HCV infection", Expert Opin. Investig. Drugs, 14(9), pp. 1129-1144 (2005).
J. Rancourt et al., "Peptide-Based Inhibitors of the Hepatitis C Virus NS3 Protease: Structure-Activity Relationship at the C-Terminal Position", J. Med. Chem., vol. 47, pp. 2511-2522 (2004).
B.W. Dymock et al., "Emerging therapies for hepatitis C virus infection", Emerging Drugs—Ashley Publications Ltd., 6(1), pp. 13-42 (2001).
M. Llinás-Brunet et al., "Peptide-Based Inhibitors of the Hepatitis C Virus Serine Protease", Bioorganic & Medicinal Chemistry Letters 8, pp. 1713-1718 (1998).
Y.S. Tsantrizos et al., "Macrocyclic Inhibitors of the NS3 Protease as Potential Therapeutic Agents of Hepatitis C Virus Infection", Angew. Chem. Int. Ed., 42(12), pp. 1355-1360 (2003).
J.L. Kim et al., "Crystal Structure of the Hepatitis C Virus NS3 Protease Domain Complexed with a Synthetic NS4A Cofactor Peptide", Cell, vol. 87, pp. 343-355 (1996).
G. Barbato et al., "Inhibitor binding induces active site stabilization of the HCV NS3 protein serine protease domain", The EMBO Journal, 19(6), pp. 1195-1206 (2000).

* cited by examiner

MACROCYCLIC HEPATITIS C SERINE PROTEASE INHIBITORS

RELATED APPLICATIONS

This application claims the benefit of U.S. provisional patent application Ser. No. 61/191,725, filed Sep. 11, 2008, and U.S. provisional patent application Ser. No. 61/209,689, filed Mar. 10, 2009. The disclosures of the aforementioned patent applications are incorporated herein in their entirety by this reference.

JOINT RESEARCH AGREEMENT

Inventions described in this application were made by or on behalf of Abbott Laboratories and Enanta Pharmaceuticals, Inc. whom are parties to a joint research agreement, that was in effect on or before the date such inventions were made and such inventions were made as a result of activities undertaken within the scope of the joint research agreement.

TECHNICAL FIELD

The present invention relates to novel macrocycles having activity against the hepatitis C virus (HCV) and useful in the treatment of HCV infections. More particularly, the invention relates to macrocyclic compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

SUMMARY OF THE INVENTION

The present invention relates to novel macrocyclic compounds and methods of treating a hepatitis C infection in a subject in need of such therapy with said macrocyclic compounds. The compounds of the present invention interfere with the life cycle of the hepatitis C virus and are useful as antiviral agents. The present invention further relates to pharmaceutical compositions comprising the compounds of the present invention, or pharmaceutically acceptable salts, esters or prodrugs thereof, in combination with a pharmaceutically acceptable carrier or excipient.

In one aspect, the invention provides a compound of formula I or formula I':

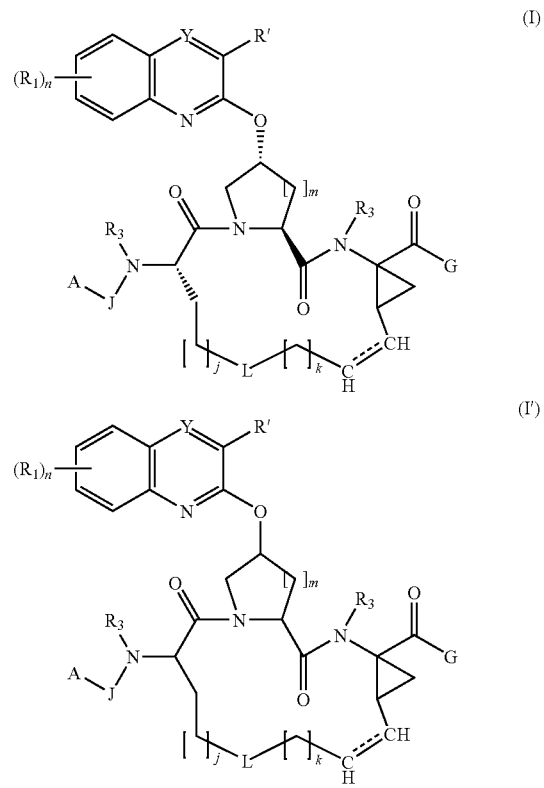

or a pharmaceutically acceptable salt, ester or prodrug thereof, wherein:

J is absent, optionally substituted alkylene, optionally substituted alkenylene, optionally substituted alkynylene, —C(O)—, —O—C(O)—, —N($R_3$)—C(O)—, —C(S)—, —C(=$NR_4$)—, —S(O)—, —S($O_2$)—, or —N($R_3$)—;

A is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

Each $R_1$ is independently selected from
(i) halogen, hydroxy, amino, —CN, —$CF_3$, —$N_3$, —$NO_2$, —$OR_4$, —$SOR_4$, —$SO_2R_4$, —N($R_3$)S($O_2$)—$R_4$, —N($R_3$)S($O_2$)N$R_3R_4$, —N$R_3R_4$, —C(O)O$R_4$, —C(O)$R_4$, —C(O)N$R_3R_4$, or —N($R_3$)C(O)$R_4$;
(ii) optionally substituted aryl;
(iii) optionally substituted heteroaryl;
(iv) optionally substituted heterocyclic;
(v) optionally substituted carbocyclic; or
(vi) optionally substituted alkyl, optionally substituted alkenyl, or optionally substituted alkynyl, each containing 0, 1, 2, or 3 heteroatoms selected from O, S, or N;

G is -E-$R_5$;

wherein E is absent; optionally substituted alkylene, optionally substituted alkenylene, optionally substituted alkynylene, each containing 0, 1, 2, or 3 heteroatoms selected from O, S, or N; or —O—, —S—, —N($R_3$)—, —N(R₃)S(O_p)—, —N(R₃)C(O)—, —N(R₃)C(O)S(O_p)—, —OS(O_p)—, —C(O)S(O_p)—, or —C(O)N(R₃)S(O_p)—;

p is 0, 1, or 2;

R₅ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;

R₃ and R₄ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

L is absent or is selected from optionally substituted alkylene, optionally substituted alkenylene or optionally substituted alkynylene, each containing 0, 1, 2, or 3 heteroatoms selected from O, S, or N;

Y is N or —C(R″)—;

wherein A, R₁, R′ and/or R″ can be taken together to form a ring;

j=0, 1, 2, 3, or 4;
k=0, 1, 2, or 3;
m=0, 1, or 2;
n is 0, 1, 2, 3, or 4; and

---- denotes a carbon-carbon single or double bond, wherein if Y is N, then R′ is optionally substituted heterocyclic, optionally substituted heteroaryl, optionally substituted aryl or optionally substituted carbocyclic, and comprises two or more fused rings, and wherein R′ is not

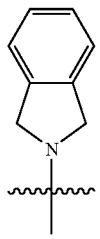 [SMILES: *N1Cc2ccccc2C1]

or

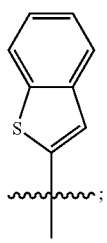 [SMILES: *c1cc2ccccc2s1]

wherein if Y is —C(R″)—, then R′ and R″ taken together with the carbon atoms to which they are attached form an aryl or heteroaryl ring, each said ring is optionally substituted;

provided that said compound is not tert-butyl (2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a- hexadecahydrocyclopropa[e]pyrrolo[1,2-a][1,4]diazacyclopentadecin-6-ylcarbamate.

In another aspect, the invention provides a pharmaceutical composition comprising a therapeutically effective amount of a compound of formula I or I', or a pharmaceutically acceptable salt, ester, or prodrug thereof, in combination with a pharmaceutically acceptable carrier or excipient.

In one aspect, the invention provides a method of treating a viral infection in a subject, comprising administering to the subject a therapeutically effective amount of a compound of formula I or I', or a pharmaceutically acceptable salt, ester or prodrug thereof, or a pharmaceutical composition comprising the same.

DETAILED DESCRIPTION OF THE INVENTION

The invention provides a compound of formula I or I':

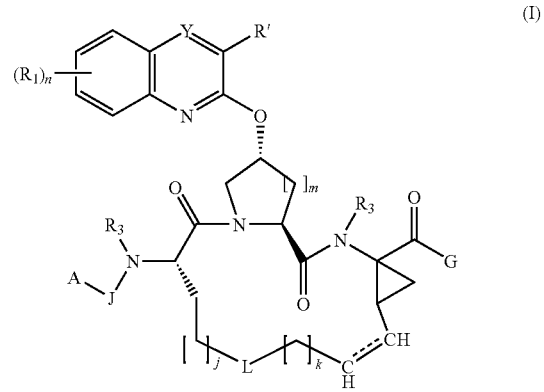

(I)

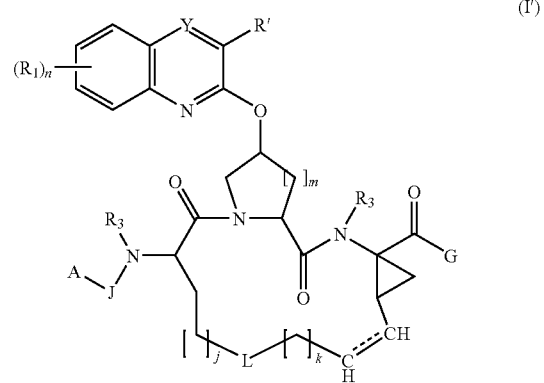

(I')

or a pharmaceutically acceptable salt, ester or prodrug thereof, wherein:

J is absent, optionally substituted alkylene, optionally substituted alkenylene, optionally substituted alkynylene, —C(O)—, —O—C(O)—, —N(R₃)—C(O)—, —C(S)—, —C(=NR₄)—, —S(O)—, —S(O₂)—, or —N(R₃)—;

A is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

Each R₁ is independently selected from
(i) halogen, hydroxy, amino, —CN, —CF₃, —N₃, —NO₂, —OR₄, —SR₄, —SOR₄, —SO₂R₄, —N(R₃)S(O₂)—

$R_4$, —$N(R_3)S(O_2)NR_3R_4$, —$NR_3R_4$, —$C(O)OR_4$, —$C(O)R_4$, —$C(O)NR_3R_4$, or —$N(R_3)C(O)R_4$;
(ii) optionally substituted aryl;
(iii) optionally substituted heteroaryl;
(iv) optionally substituted heterocyclic;
(v) optionally substituted carbocyclic; or
(vi) optionally substituted alkyl, optionally substituted alkenyl, or optionally substituted alkynyl, each containing 0, 1, 2, or 3 heteroatoms selected from O, S, or N;

G is -E-$R_5$;
wherein E is absent; optionally substituted alkylene, optionally substituted alkenylene, optionally substituted alkynylene, each containing 0, 1, 2, or 3 heteroatoms selected from O, S, or N; or —O—, —S—, —$N(R_3)$—, —$N(R_3)S(O_p)$—, —$N(R_3)C(O)$—, —$N(R_3)C(O)S(O_p)$—, —$OS(O_p)$—, —$C(O)S(O_p)$—, or —$C(O)N(R_3)S(O_p)$—;

p is 0, 1, or 2;
$R_5$ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;

$R_3$ and $R_4$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

L is absent or is selected from optionally substituted alkylene, optionally substituted alkenylene or optionally substituted alkynylene, each containing 0, 1, 2, or 3 heteroatoms selected from O, S, or N;

Y is N or —C(R")—;
wherein A, $R_1$, R' and/or R" can be taken together to form a ring;
j=0, 1, 2, 3, or 4;
k=0, 1, 2, or 3;
m=0, 1, or 2;
n is 0, 1, 2, 3, or 4; and
===== denotes a carbon-carbon single or double bond (i.e., 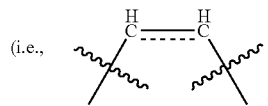 means

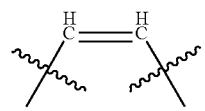 [SMILES: */C=C\*]

or

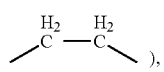 ), wherein if Y is N, then R' is optionally substituted heterocyclic, optionally substituted heteroaryl, optionally substituted aryl or optionally substituted carbocyclic, and comprises two or more fused rings, and wherein R' is not

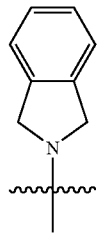

or

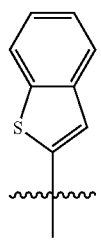;

wherein if Y is —C(R")—, then R' and R" taken together with the carbon atoms to which they are attached form an aryl or heteroaryl ring, each of which is optionally substituted;

provided that said compound is not tert-butyl (2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

It is understood that the embodiments of the invention discussed below with respect to the preferred variable selections can be taken alone or in combination with one or more of the other embodiments, or preferred variable selections, of the invention, as if each combination were explicitly listed herein.

In one aspect, the invention provides a compound of formula I or I', or a pharmaceutically acceptable salt, ester or prodrug thereof, wherein Y is CR", and R' and R" taken together with the carbon atoms to which they are attached form an optionally substituted aryl or an optionally substituted heteroaryl ring.

In another aspect, the invention provides a compound of formula I or I', or a pharmaceutically acceptable salt, ester or prodrug thereof, wherein Y is CR", and R' and R" taken together with the carbon atoms to which they are attached form an optionally substituted aryl ring, preferably phenyl.

Alternatively or additionally, k=3, j=1 and L is absent.

Alternatively or additionally, R' and R", and the atoms to which each is attached, form an aryl which is substituted by $(R_2)_x$, wherein each $R_2$ is independently selected from halogen, hydroxy, amino, —CN, —$CF_3$, —$N_3$, —$NO_2$, —$OR_4$, —$SR_4$, —$SOR_4$, —$SO_2R_4$, —$N(R_3)S(O_2)$—$R_4$, —$N(R_3)S(O_2)NR_3R_4$, —$NR_3R_4$, —$C(O)OR_4$, —$C(O)R_4$, —$C(O)NR_3R_4$, or —$N(R_3)C(O)R_4$; optionally substituted aryl; optionally substituted heteroaryl; optionally substituted heterocyclic; optionally substituted carbocyclic; or optionally substituted alkyl, optionally substituted alkenyl, or optionally substituted alkynyl, each containing 0, 1, 2, or 3 heteroatoms selected from O, S, or N; and x is 0, 1, 2, 3, or 4.

Alternatively or additionally, $R_1$ is absent (i.e., n=0) or is halogen, hydroxy, amino, —CN, —CF$_3$, —N$_3$, —NO$_2$, —OR$_4$, —SR$_4$, —SOR$_4$, —SO$_2$R$_4$, —N(R$_3$)S(O$_2$)—R$_4$, —N(R$_3$)S(O$_2$)NR$_3$R$_4$, —NR$_3$R$_4$, —C(O)OR$_4$, —C(O)R$_4$, —C(O)NR$_3$R$_4$, or —N(R$_3$)C(O)R$_4$.

Alternatively or additionally, R' and R", and the atoms to which each is attached, form an aryl which is substituted by $(R_2)_x$, wherein each $R_2$ is independently absent (i.e., x=0) or halogen.

Alternatively or additionally, $R_1$ is absent (i.e., n=0) or halogen.

Alternatively or additionally, E is —NH—, —NHS(O$_p$)—, or —NH(CO)S(O$_p$)—, and p is 2.

Alternatively or additionally, E is —NHS(O$_p$)—, and p is 2.

Alternatively or additionally, $R_5$ is cyclopropyl, cyclobutyl, cyclopentyl, cyclohexyl, cycloheptyl, pyridinyl, pyrimidinyl, furanyl, thienyl, pyrrolyl, pyrazolyl, pyrrolidinyl, morpholinyl, piperidinyl, piperazinyl, or imidazolyl, each of which is optionally substituted. In a further embodiment, $R_5$ is optionally substituted cyclopropyl or optionally substituted thienyl, preferably cyclopropyl or thienyl.

Alternatively or additionally, J is —C(O)—, —O—C(O)—, —C(S)—, —C(=NR$_4$)—, —S(O)—, or —S(O$_2$)—. Preferably, J is —C(O)—.

Alternatively or additionally, m is 1.

Alternatively or additionally, each $R_3$ is H.

Alternatively or additionally, A is optionally substituted —C$_1$-C$_8$ alkyl, containing 0, 1, 2, or 3 heteroatoms selected from O, S, or N; optionally substituted aryl, optionally substituted —C$_1$-C$_8$ alkoxy, optionally substituted heteroaryl, optionally substituted —C$_3$-C$_{12}$ cycloalkyl, or optionally substituted —C$_3$-C$_{12}$ heterocycloalkyl. In a further embodiment, A is selected from

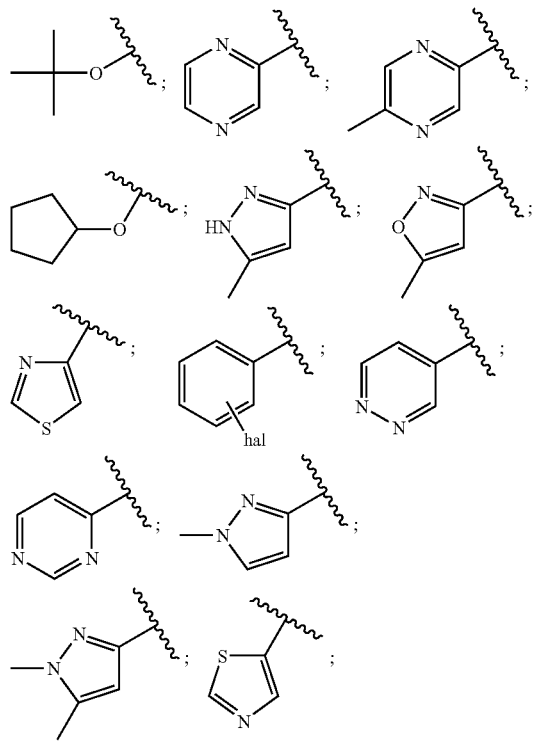

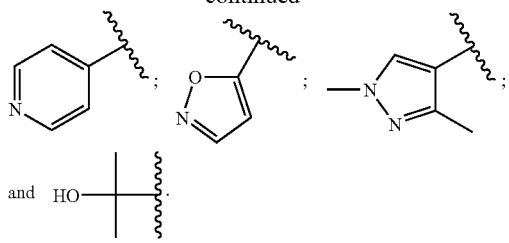

Preferably, A is a 5-methyl-pyrazin-2-yl.

In still another aspect, the invention provides a compound of formula I or I', or a pharmaceutically acceptable salt, ester or prodrug thereof, wherein Y is CR", and R' and R" taken together with the carbon atoms to which they are attached form an optionally substituted heteroaryl ring. The remaining variables are as defined above, including the alternative or preferred embodiments, as if repeated herein.

The invention also features a compound of formula I or I' (preferably formula I), or a pharmaceutically acceptable salt, ester or prodrug thereof, wherein Y is CR", and R' and R" taken together with the carbon atoms to which they are attached form an aryl or heteroaryl ring, preferably phenyl, which is optionally substituted with one or more R$_2$;

k=0, j=0, m=1, n=0, 1, 2, 3 or 4, and L is C$_3$-C$_6$alkylene, C$_3$-C$_6$alkenylene or C$_3$-C$_6$alkynylene and is optionally substituted with one or more R$_7$ (preferably butylene);

J is —C(O)— or —O—C(O)— (preferably —C(O)—);

A is C$_1$-C$_6$alkyl, C$_2$-C$_6$alkenyl, C$_2$-C$_6$alkynyl, C$_3$-C$_{10}$carbocyclic, aryl, heteroaryl or heterocyclic comprising 5 to 10 ring atoms, and A is optionally substituted with one or more R$_6$;

G is -E-R$_5$, E is —NHS(O$_2$)—; R$_5$ is C$_1$-C$_6$alkyl, C$_2$-C$_6$alkenyl, C$_2$-C$_6$alkynyl, C$_3$-C$_{10}$carbocyclic (preferably cyclopropyl), heteroaryl (preferably thienyl) or heterocyclic comprising 5 to 10 ring atoms, and R$_5$ is optionally substituted with one or more R$_7$;

each R$_1$ and R$_2$ is independently selected from halogen, hydroxy, amino, —CN, —CF$_3$, —N$_3$, —NO$_2$, —OR$_4$, —SR$_4$, —S(O)R$_4$, —S(O$_2$)R$_4$, —NR$_3$R$_4$, —C(O)OR$_4$, —C(O)R$_4$, —C(O)NR$_3$R$_4$, —N(R$_3$)C(O)R$_4$, C$_1$-C$_6$alkyl, C$_2$-C$_6$alkenyl, C$_2$-C$_6$alkynyl, C$_1$-C$_6$haloalkyl, C$_2$-C$_6$haloalkenyl, C$_2$-C$_6$haloalkynyl, C$_3$-C$_{10}$carbocyclic optionally substituted with one or more R$_7$, or heterocyclic comprising 5 to 10 ring atoms and optionally substituted with one or more R$_7$, wherein each R$_6$ and R$_7$ is independently selected at each occurrence from halogen, hydroxy, amino, —CF$_3$, —CN, —N$_3$, —NO$_2$, —C$_1$-C$_6$alkyl (preferably methyl), C$_2$-C$_6$alkenyl, C$_2$-C$_6$alkynyl, C$_1$-C$_6$haloalkyl, C$_2$-C$_6$haloalkenyl, or C$_2$-C$_6$haloalkynyl (and, preferably, R$_1$ and R$_2$ is absent in each instance); and R$_3$ and R$_4$ are each independently selected at each occurrence from hydrogen, C$_1$-C$_6$alkyl, C$_2$-C$_6$alkenyl, or C$_2$-C$_6$alkynyl and R$_3$ is preferably hydrogen.

The invention further features a compound of formula I or I' (preferably formula I), or a pharmaceutically acceptable salt, ester or prodrug thereof, wherein Y is CR", R' and R" taken together with the carbon atoms to which they are attached form a phenyl optionally substituted with one or more R$_2$;

k=3, j=1, m=1, n=0,1, 2, 3, or 4, and L is absent;

J is —C(O)— or —O—C(O)—;

A is $C_1$-$C_6$alkyl, aryl, heteroaryl, $C_5$-$C_6$carbocyclic or heterocyclic comprising 5 to 6 ring atoms, and is optionally substituted with one or more $R_6$;

G is -E-$R_5$, E is —NHS($O_2$)—; $R_5$ is $C_3$-$C_6$carbocyclic or heteroaryl, and is optionally substituted with one or more $R_7$; in one embodiment, $R_5$ is selected from cyclopropyl, cyclobutyl, cyclopentyl, cyclohexyl, cycloheptyl, pyridinyl, pyrimidinyl, furanyl, thienyl, pyrrolyl, pyrazolyl, pyrrolidinyl, morpholinyl, piperidinyl, piperazinyl, or imidazolyl, each of which is optionally substituted with one or more $R_7$; preferably, $R_5$ is cyclopropyl;

each $R_1$ and $R_2$ is independently selected from halogen, hydroxy, amino, —CN, —$N_3$, —$CF_3$, —$NO_2$, —$OR_4$, —$SR_4$, —S(O)$R_4$, —S($O_2$)$R_4$, —$NR_3R_4$, —C(O)$OR_4$, —C(O)$NR_3R_4$, —N($R_3$)C(O)$R_4$, $C_1$-$C_6$alkyl, $C_2$-$C_6$alkenyl, $C_2$-$C_6$alkynyl, $C_1$-$C_6$haloalkyl, $C_2$-$C_6$haloalkenyl, or $C_2$-$C_6$haloalkynyl;

$R_3$ is hydrogen; and each $R_4$ is independently selected from hydrogen, $C_1$-$C_6$alkyl, $C_2$-$C_6$alkenyl, or $C_2$-$C_6$alkynyl;

$R_6$ and $R_7$ is independently selected at each occurrence from halogen, hydroxy, amino, —$CF_3$, —CN, —$N_3$, —$NO_2$, —$C_1$-$C_6$alkyl (preferably methyl), $C_2$-$C_6$alkenyl, $C_2$-$C_6$alkynyl, $C_1$-$C_6$haloalkyl, $C_2$-$C_6$haloalkenyl, or $C_2$-$C_6$haloalkynyl;

A can be, for example, selected from the following groups, each group optionally substituted with one or more $R_6$:

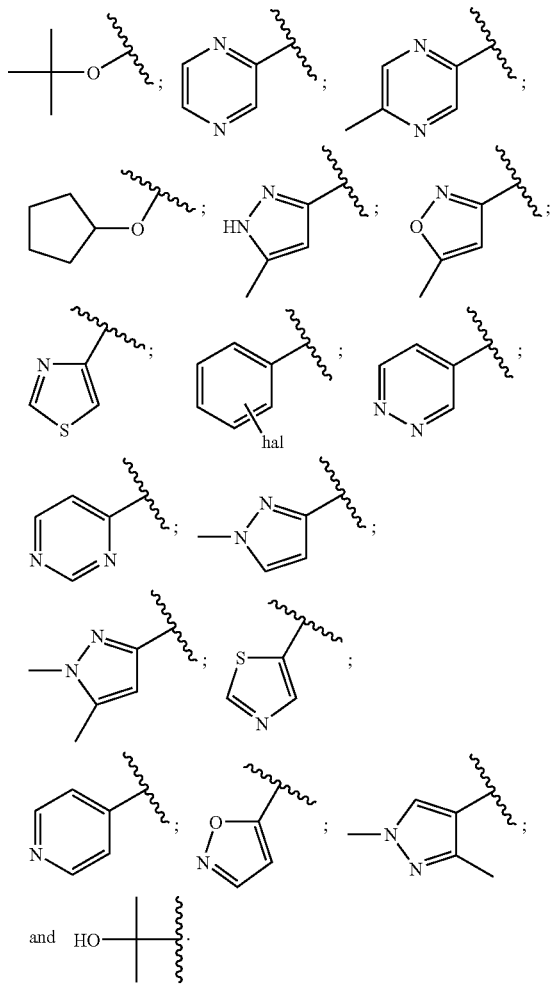

In yet another aspect, the invention provides a compound of formula I or I', or a pharmaceutically acceptable salt, ester or prodrug thereof, wherein R' is optionally substituted heterocyclic, optionally substituted heteroaryl, optionally substituted aryl or optionally substituted carbocyclic, and comprises two or more fused rings, and wherein R' is not

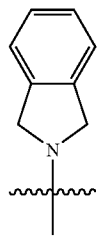

or

and Y is N.

In still another aspect, the invention provides a compound of formula I or I', or a pharmaceutically acceptable salt, ester or prodrug thereof, wherein R' is an optionally substituted heterocyclic or optionally substituted heteroaryl, comprises two or more fused rings, and wherein R' is not

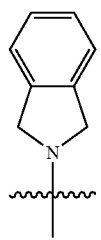

or

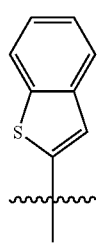

and Y is N. Preferably, R' is an optionally substituted fused bicyclic heterocyclic or fused bicyclic heteroaryl. Alternatively or additionally, R' is an optionally substituted with one or more $R_2$, and preferably with an alkyl or aryl.

The remaining variables are as defined above, including in the preferred and alternative embodiments.

In another aspect, the invention provides a compound of formula I or I' or a pharmaceutically acceptable salt, ester or prodrug thereof, wherein R' is optionally substituted heterocyclic, optionally substituted heteroaryl, optionally substituted aryl or optionally substituted carbocyclic, and comprises two or more fused rings, and wherein R' is not

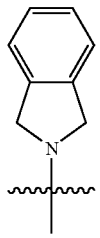 [SMILES: *N1Cc2ccccc2C1]

or

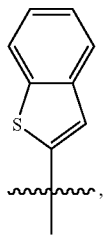 [SMILES: *c1cc2ccccc2s1]

and Y is N; wherein k=3, j=1 and L is absent.

Preferably, the compound has formula I.

Alternatively or additionally, m is 1.

Alternatively or additionally, each $R_3$ is H.

Alternatively or additionally, $R_1$ and $R_2$ are independently hydrogen or halogen.

Alternatively or additionally, E is —NHS($O_p$)—, and p is 2.

Alternatively or additionally, $R_5$ is cyclopropyl, cyclobutyl, cyclopentyl, cyclohexyl, cycloheptyl, pyridinyl, pyrimidinyl, furanyl, thienyl, pyrrolyl, pyrazolyl, pyrrolidinyl, morpholinyl, piperidinyl, piperazinyl, or imidazolyl, each of which is optionally substituted. In a further embodiment, $R_5$ is optionally substituted cyclopropyl or optionally substituted thienyl, and preferably cyclopropyl or thienyl.

Alternatively or additionally, J is —C(O)—.

Alternatively or additionally, A is optionally substituted —$C_1$-$C_8$ alkyl, containing 0, 1, 2, or 3 heteroatoms selected from O, S, or N; optionally substituted aryl, optionally substituted —$C_1$-$C_8$ alkoxy, optionally substituted heteroaryl, optionally substituted —$C_3$-$C_{12}$ cycloalkyl, or optionally substituted —$C_3$-$C_{12}$ heterocycloalkyl. In a further embodiment, A is selected from

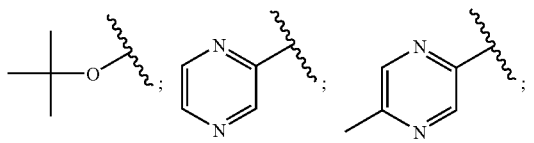

-continued

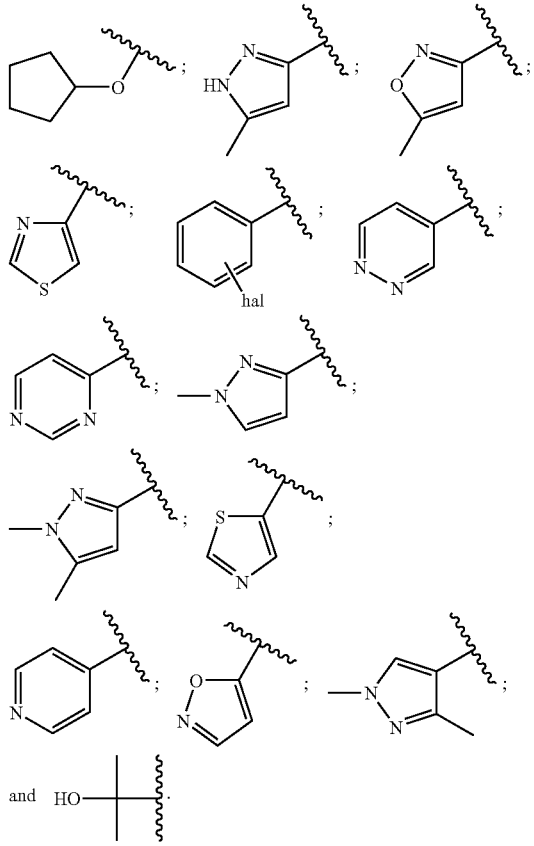

In another aspect, the invention provides a compound of formula I or I' or a pharmaceutically acceptable salt, ester or prodrug thereof, wherein Y is N, and R' is

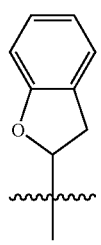

or

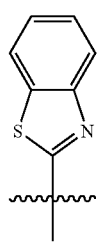

and is optionally substituted; provided that said compound is not tert-butyl (2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15, 16,16a-hexadecahydrocyclopropa[e]pyrrolo[1,2-a][1,4]
diazacyclopentadecin-6-ylcarbamate.

The invention also features a compound of formula I or formula I' (preferably formula I), or a pharmaceutically acceptable salt, ester or prodrug thereof, wherein Y is N, and R' is

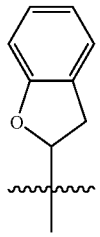 [SMILES: *C1Cc2ccccc2O1]

or

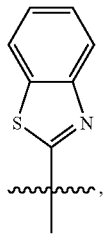 [SMILES: *c1nc2ccccc2s1]

and is optionally substituted with one or more $R_2$;

k=0, j=0, m=1, n=0,1, 2, 3, or 4, and L is $C_3$-$C_6$alkylene, $C_3$-$C_6$alkenylene or $C_3$-$C_6$alkynylene and is optionally substituted with one or more $R_7$;

J is —C(O)— or —O—C(O)—;

A is $C_1$-$C_6$alkyl, $C_2$-$C_6$alkenyl, $C_2$-$C_6$alkynyl, $C_3$-$C_{10}$carbocyclic, aryl, heteroaryl, or heterocyclic comprising 5 to 10 ring atoms, and A is optionally substituted with one or more $R_6$;

G is -E-$R_5$, E is —NHS($O_2$)-; $R_5$ is $C_1$-$C_6$alkyl, $C_2$-$C_6$alkenyl, $C_2$-$C_6$alkynyl, $C_3$-$C_{10}$carbocyclic, aryl, heteroaryl, or heterocyclic comprising 5 to 10 ring atoms, and $R_5$ is optionally substituted with one or more $R_7$;

each $R_1$ and $R_2$ is independently selected from halogen, hydroxy, amino, —CN, —$CF_3$, —$N_3$, —$NO_2$, —$OR_4$, —$SR_4$, —S(O)$R_4$, —S($O_2$)$R_4$, —$NR_3R_4$, —C(O)$OR_4$, —C(O)$R_4$, —C(O)$NR_3R_4$, —N($R_3$)C(O)$R_4$, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C_3$-$C_{10}$carbocyclic optionally substituted with one or more $R_7$, or heterocyclic comprising 5 to 10 ring atoms and optionally substituted with one or more $R_7$, wherein each $R_6$ and $R_7$ is independently selected from halogen, hydroxy, amino, —CN, —$CF_3$, —$N_3$, —$NO_2$, —$C_1$-$C_6$alkyl, $C_2$-$C_6$alkenyl, $C_2$-$C_6$alkynyl, $C_1$-$C_6$haloalkyl, $C_2$-$C_6$haloalkenyl, or $C_2$-$C_6$haloalkynyl; and $R_3$ or $R_4$ are each independently selected at each occurrence from hydrogen, $C_1$-$C_6$alkyl, $C_2$-$C_6$alkenyl, or $C_2$-$C_6$alkynyl;

provided that said compound is not tert-butyl (2R,6S,13aS, 14aR,16aS,Z)-2-(3-(benzo[d]thiazol-2-yl)quinoxalin-2-yloxy)-14a-(cyclopropylsulfonylcarbamoyl)-5,16-dioxo-1, 2,3,5,6,7,8,9,10,11,13a,14,14a,15,16,16a-hexadecahydrocyclopropa[e]pyrrolo[1,2-a][1,4]
diazacyclopentadecin-6-ylcarbamate.

The invention further features a compound of formula I or formula I' (preferably formula I), or a pharmaceutically acceptable salt, ester or prodrug thereof, wherein Y is N, and R' is

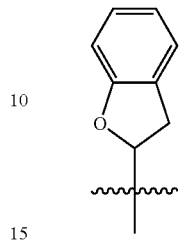

or

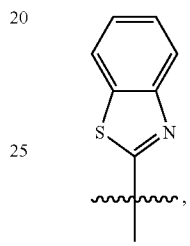

and is optionally substituted with one or more $R_2$;

k=0, j=0, m=1, n=0,1, 2, 3, or 4, and L is $C_3$-$C_6$alkylene, $C_3$-$C_6$alkenylene or $C_3$-$C_6$alkynylene and is optionally substituted with one or more halo;

J is —C(O)— or —O—C(O)—; A is $C_1$-$C_6$alkyl, aryl, heteroaryl, $C_3$-$C_{10}$carbocyclic or heterocyclic comprising 5 to 10 ring atoms, and is optionally substituted with one or more $R_6$;

G is -E-$R_5$, E is —NHS($O_2$)—; $R_5$ is $C_3$-$C_{10}$carbocyclic or heteroaryl, and is optionally substituted with one or more $R_7$;

each $R_1$ and $R_2$ are independently selected from halogen, hydroxy, amino, —CN, —$CF_3$, —$N_3$, —$NO_2$, —$OR_4$, —$SR_4$, —S(O)$R_4$, —S($O_2$)$R_4$, —$NR_3R_4$, —C(O)$OR_4$, —C(O)$R_4$, —C(O)$NR_3R_4$, —N($R_3$)C(O)$R_4$, $C_1$-$C_6$alkyl, $C_2$-$C_6$alkenyl, $C_2$-$C_6$alkynyl, $C_1$-$C_6$haloalkyl, $C_2$-$C_6$haloalkenyl, $C_2$-$C_6$haloalkynyl, $C_3$-$C_{10}$carbocyclic optionally substituted with one or more $R_7$, or heterocyclic comprising 5 to 10 ring atoms and optionally substituted with one or more $R_7$, wherein each $R_6$ and $R_7$ is independently selected from halogen, hydroxy, amino, —CN, —$CF_3$, —$N_3$, —$NO_2$, —$C_1$-$C_6$alkyl, $C_2$-$C_6$alkenyl, $C_2$-$C_6$alkynyl, $C_1$-$C_6$haloalkyl, $C_2$-$C_6$haloalkenyl, or $C_2$-$C_6$haloalkynyl; $R_3$ is hydrogen; and each $R_4$ is independently selected from hydrogen, $C_1$-$C_6$alkyl, $C_2$-$C_6$alkenyl, or $C_2$-$C_6$alkynyl;

provided that said compound is not tert-butyl (2R,6S,13aS, 14aR,16aS,Z)-2-(3-(benzo[d]thiazol-2-yl)quinoxalin-2-yloxy)-14a-(cyclopropylsulfonylcarbamoyl)-5,16-dioxo-1, 2,3,5,6,7,8,9,10,11,13a,14,14a,15,16,16a-hexadecahydrocyclopropa[e]pyrrolo[1,2-a][1,4]
diazacyclopentadecin-6-ylcarbamate.

In addition, the invention features a compound of formula I or formula I' (preferably formula I), or a pharmaceutically acceptable salt, ester or prodrug thereof, wherein Y is N, and R' is

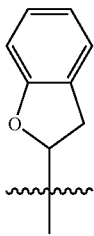 [SMILES: *C1Cc2ccccc2O1]

or

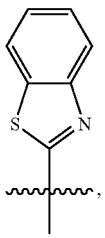 [SMILES: *c1nc2ccccc2s1]

and is optionally substituted with one or more $R_2$;

k=3, j=1, m=1, n=0,1, 2, 3, or 4, and L is absent; J is —C(O)— or —O—C(O)—; A is $C_5$-$C_6$carbocyclic or a heterocyclic comprising 5 to 6 ring atoms, and is optionally substituted with one or more $R_6$;

G is -E-$R_5$, E is —NHS($O_2$)—; $R_5$ is $C_3$-$C_6$carbocyclic or heteroaryl, and is optionally substituted with one or more $R_7$;

each $R_1$ and $R_2$ are independently selected from halogen, hydroxy, amino, —CN, —$CF_3$, —$N_3$, —$NO_2$, —$OR_4$, —$SR_4$, —S(O)$R_4$, —S($O_2$)$R_4$, —$NR_3R_4$, —C(O)$OR_4$, —C(O)$R_4$, —C(O)$NR_3R_4$, —N($R_3$)C(O)$R_4$, $C_1$-$C_6$alkyl, $C_2$-$C_6$alkenyl, $C_2$-$C_6$alkynyl, $C_1$-$C_6$haloalkyl, $C_2$-$C_6$haloalkenyl, or $C_2$-$C_6$haloalkynyl;

$R_3$ is hydrogen; and each $R_4$ is independently selected from hydrogen, $C_1$-$C_6$alkyl, $C_2$-$C_6$alkenyl, or $C_2$-$C_6$alkynyl and $R_6$ and $R_7$ are as defined above;

provided that said compound is not tert-butyl (2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

In one embodiment, $R_5$ is selected from cyclopropyl, cyclobutyl, cyclopentyl, cyclohexyl, cycloheptyl, pyridinyl, pyrimidinyl, furanyl, thienyl, pyrrolyl, pyrazolyl, pyrrolidinyl, morpholinyl, piperidinyl, piperazinyl, or imidazolyl, each of which is optionally substituted with one or more $R_7$. Preferably, $R_5$ is cyclopropyl. A can be, for example, selected from the following groups and optionally substituted with one or more $R_6$:

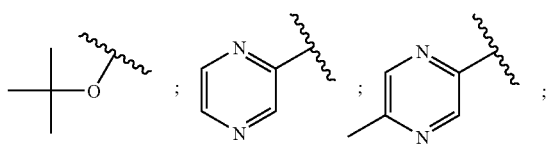

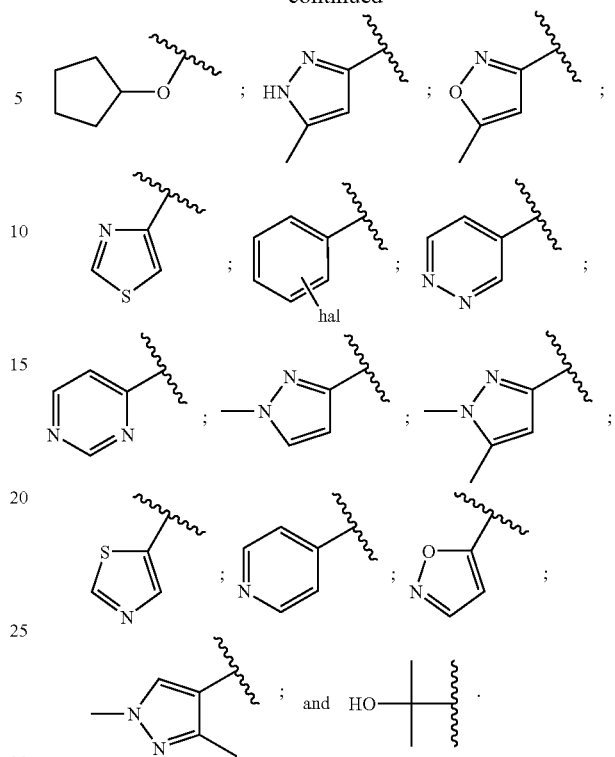

Representative compounds include, but are not limited to, the following compounds:

(1) tert-butyl (2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate;

(2) (2R,6S,13aS,14aR,16aS,Z)-2-(3-(benzo[d]thiazol-2-yl)quinoxalin-2-yloxy)-N-(cyclopropylsulfonyl)-6-(isonicotinamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(3) (2R,6S,13aS,14aR,16aS,Z)-2-(3-(benzo[d]thiazol-2-yl)quinoxalin-2-yloxy)-N-(cyclopropylsulfonyl)-6-(2-fluorobenzamido)-5,16-dioxo-1,2,3,5,6,7,8,9,10,11,13a,14,14a,15, 16,16a-hexadecahydrocyclopropa[e]pyrrolo[1,2-a][1,4]diazacyclopentadecine-14a-carboxamide;

(4) N-((2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide;

(5) (2R,6S,13aS,14aR,16aS,Z)-2-(3-(benzo[d]thiazol-2-yl)quinoxalin-2-yloxy)-N-(cyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(6) N-((2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-5-carboxamide;

(7) N-a2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16, 16a-hexadecahydrocyclopropa[e]pyrrolo[1,2-a][1,4] diazacyclopentadecin-6-yl)thiazole-4-carboxamide;

(8) (2R,6S,13aS,14aR,16aS,Z)-2-(3-(benzo[d]thiazol-2-yl) quinoxalin-2-yloxy)-N-(cyclopropylsulfonyl)-6-(1-methyl-1H-pyrazole-3-carboxamido)-5,16-dioxo-1,2,3,5,6, 7,8,9,10,11,13a,14,14a,15,16,16a-hexadecahydrocyclopropa[e]pyrrolo[1,2-a][1,4] diazacyclopentadecine-14a-carboxamide;

(9) (2R,6S,13aS,14aR,16aS,Z)-2-(3-(benzo[d]thiazol-2-yl) quinoxalin-2-yloxy)-N-(cyclopropylsulfonyl)-5,16-dioxo-6-(pyrimidine-4-carboxamido)-1,2,3,5,6,7,8,9,10,11, 13a,14,14a,15,16,16a-hexadecahydrocyclopropa[e] pyrrolo[1,2-a][1,4]diazacyclopentadecine-14a-carboxamide;

(10) (2R,6S,13aS,14aR,16aS,Z)-2-(3-(benzo[d]thiazol-2-yl) quinoxalin-2-yloxy)-N-(cyclopropylsulfonyl)-6-(1,3-dimethyl-1H-pyrazole-4-carboxamido)-5,16-dioxo-1,2,3, 5,6,7,8,9,10,11,13a,14,14a,15,16,16a-hexadecahydrocyclopropa[e]pyrrolo[1,2-a][1,4] diazacyclopentadecine-14a-carboxamide;

(11) (2R,6S,13aS,14aR,16aS,Z)-2-(3-(benzo[d]thiazol-2-yl) quinoxalin-2-yloxy)-N-(cyclopropylsulfonyl)-6-(3-fluorobenzamido)-5,16-dioxo-1,2,3,5,6,7,8,9,10,11,13a,14, 14a,15,16,16a-hexadecahydrocyclopropa[e]pyrrolo[1,2-a][1,4]diazacyclopentadecine-14a-carboxamide;

(12) tert-butyl (2R,6S,13aS,14aR,16aS,Z)-2-(3-(benzofuran-2-yl)quinoxalin-2-yloxy)-14a-(cyclopropylsulfonylcarbamoyl)-5,16-dioxo-1,2,3,5,6,7,8,9,10,11,13a,14,14a, 15,16,16a-hexadecahydrocyclopropa[e]pyrrolo[1,2-a][1, 4]diazacyclopentadecin-6-ylcarbamate;

(13) N-((2R,6S,13aS,14aR,16aS,Z)-2-(3-(benzofuran-2-yl) quinoxalin-2-yloxy)-14a-(cyclopropylsulfonylcarbamoyl)-5,16-dioxo-1,2,3,5,6,7,8,9,10,11,13a,14,14a,15,16, 16a-hexadecahydrocyclopropa[e]pyrrolo[1,2-a][1,4] diazacyclopentadecin-6-yl)-5-methylisoxazole-3-carboxamide;

(14) (2R,6S,13aS,14aR,16aS,Z)-2-(3-(benzofuran-2-yl)quinoxalin-2-yloxy)-N-(cyclopropylsulfonyl)-6-(5-methylpyrazine-2-carboxamido)-5,16-dioxo-1,2,3,5,6,7,8,9, 10,11,13a,14,14a,15,16,16a-hexadecahydrocyclopropa[e] pyrrolo[1,2-a][1,4]diazacyclopentadecine-14a-carboxamide;

(15) (2R,6S,13aS,14aR,16aS,Z)-2-(3-(benzofuran-2-yl)quinoxalin-2-yloxy)-N-(cyclopropylsulfonyl)-6-(1-methyl-1H-pyrazole-3-carboxamido)-5,16-dioxo-1,2,3,5,6,7,8,9, 10,11,13a,14,14a,15,16,16a-hexadecahydrocyclopropa[e] pyrrolo[1,2-a][1,4]diazacyclopentadecine-14a-carboxamide;

(16) (2R,6S,13aS,14aR,16aS,Z)-2-(3-(benzofuran-2-yl)quinoxalin-2-yloxy)-N-(cyclopropylsulfonyl)-6-(1,5-dimethyl-1H-pyrazole-3-carboxamido)-5,16-dioxo-1,2,3,5,6, 7,8,9,10,11,13a,14,14a,15,16,16a-hexadecahydrocyclopropa[e]pyrrolo[1,2-a][1,4] diazacyclopentadecine-14a-carboxamide;

(17) (2R,6S,13aS,14aR,16aS,Z)-2-(3-(benzofuran-2-yl)quinoxalin-2-yloxy)-N-(cyclopropylsulfonyl)-5,16-dioxo-6-(pyrimidine-4-carboxamido)-1,2,3,5,6,7,8,9,10,11,13a, 14,14a,15,16,16a-hexadecahydrocyclopropa[e]pyrrolo[1, 2-a][1,4]diazacyclopentadecine-14a-carboxamide;

(18) tert-butyl (2R,6S,13aS,14aR,16aS,Z)-2-(3-(benzo[b] thiophen-2-yl)quinoxalin-2-yloxy)-14a-(cyclopropylsulfonylcarbamoyl)-5,16-dioxo-1,2,3,5,6,7,8,9,10,11,13a, 14,14a,15,16,16a-hexadecahydrocyclopropa[e]pyrrolo[1, 2-a][1,4]diazacyclopentadecin-6-ylcarbamate;

(19) N-((2R,6S,13aS,14aR,16aS,Z)-2-(3-(benzo[b] thiophen-2-yl)quinoxalin-2-yloxy)-14a-(cyclopropylsulfonylcarbamoyl)-5,16-dioxo-1,2,3,5,6,7,8,9,10,11,13a, 14,14a,15,16,16a-hexadecahydrocyclopropa[e]pyrrolo[1, 2-a][1,4]diazacyclopentadecin-6-yl)-5-methylisoxazole-3-carboxamide;

(20) (2R,6S,13aS,14aR,16aS,Z)-2-(3-(benzo[b]thiophen-2-yl)quinoxalin-2-yloxy)-N-(cyclopropylsulfonyl)-6-(5-methylpyrazine-2-carboxamido)-5,16-dioxo-1,2,3,5,6,7, 8,9,10,11,13a,14,14a,15,16,16a-hexadecahydrocyclopropa[e]pyrrolo[1,2-a][1,4] diazacyclopentadecine-14a-carboxamide;

(21) (2R,6S,13aS,14aR,16aS,Z)-2-(3-(benzo[b]thiophen-2-yl)quinoxalin-2-yloxy)-N-(cyclopropylsulfonyl)-6-(1-methyl-1H-pyrazole-3-carboxamido)-5,16-dioxo-1,2,3,5, 6,7,8,9,10,11,13a,14,14a,15,16,16a-hexadecahydrocyclopropa[e]pyrrolo[1,2-a][1,4] diazacyclopentadecine-14a-carboxamide;

(22) (2R,6S,13aS,14aR,16aS,Z)-2-(3-(benzo[b]thiophen-2-yl)quinoxalin-2-yloxy)-N-(cyclopropylsulfonyl)-6-(1,5-dimethyl-1H-pyrazole-3-carboxamido)-5,16-dioxo-1,2,3, 5,6,7,8,9,10,11,13a,14,14a,15,16,16a-hexadecahydrocyclopropa[e]pyrrolo[1,2-a][1,4] diazacyclopentadecine-14a-carboxamide;

(23) (2R,6S,13aS,14aR,16aS,Z)-2-(3-(benzo[b]thiophen-2-yl)quinoxalin-2-yloxy)-N-(cyclopropylsulfonyl)-5,16-dioxo-6-(pyrimidine-4-carboxamido)-1,2,3,5,6,7,8,9,10,11, 13a,14,14a,15,16,16a-hexadecahydrocyclopropa[e] pyrrolo[1,2-a][1,4]diazacyclopentadecine-14a-carboxamide;

(24) tert-butyl (2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4] diazacyclopentadecin-6-ylcarbamate;

(25) (2R,6S,13aS,14aR,16aS,Z)-N-(cyclopropylsulfonyl)-5, 16-dioxo-2-(phenanthridin-6-yloxy)-6-(pyrazine-2-carboxamido)-1,2,3,5,6,7,8,9,10,11,13a,14,14a,15,16,16a-hexadecahydrocyclopropa[e]pyrrolo[1,2-a][1,4] diazacyclopentadecine-14a-carboxamide;

(26) Cyclopentyl (2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4] diazacyclopentadecin-6-ylcarbamate;

(27) (2R,6S,13aS,14aR,16aS,Z)-N-(cyclopropylsulfonyl)-6-(5-methyl-1H-pyrazole-3-carboxamido)-5,16-dioxo-2-(phenanthridin-6-yloxy)-1,2,3,5,6,7,8,9,10,11,13a,14, 14a,15,16,16a-hexadecahydrocyclopropa[e]pyrrolo[1,2-a][1,4]diazacyclopentadecine-14a-carboxamide;

(28) N-((2R,6S,13aS,14aR,16aS,Z)-14a-(cyclopropylsulfonylcarbamoyl)-5,16-dioxo-2-(phenanthridin-6-yloxy)-1, 2,3,5,6,7,8,9,10,11,13a,14,14a,15,16,16a-hexadecahydrocyclopropa[e]pyrrolo[1,2-a][1,4] diazacyclopentadecin-6-yl)-5-methylisoxazole-3-carboxamide;

(29) (2R,6S,13aS,14aR,16aS,Z)-N-(cyclopropylsulfonyl)-6-(5-methylpyrazine-2-carboxamido)-5,16-dioxo-2-(phenanthridin-6-yloxy)-1,2,3,5,6,7,8,9,10,11,13a,14, 14a,15,16,16a-hexadecahydrocyclopropa[e]pyrrolo[1,2-a][1,4]diazacyclopentadecine-14a-carboxamide;

(30) N-((2R,6S,13aS,14aR,16aS,Z)-14a-(cyclopropylsulfonylcarbamoyl)-5,16-dioxo-2-(phenanthridin-6-yloxy)-1, 2,3,5,6,7,8,9,10,11,13a,14,14a,15,16,16a-hexadecahydrocyclopropa[e]pyrrolo[1,2-a][1,4] diazacyclopentadecin-6-yl)thiazole-5-carboxamide;

(31) (2R,6S,13aS,14aR,16aS,Z)-N-(cyclopropylsulfonyl)-6-(2-fluorobenzamido)-5,16-dioxo-2-(phenanthridin-6-yloxy)-1,2,3,5,6,7,8,9,10,11,13a,14,14a,15,16,16a-hexa-

(32) (2R,6S,13aS,14aR,16aS,Z)-N-(cyclopropylsulfonyl)-5,16-dioxo-2-(phenanthridin-6-yloxy)-6-(pyridazine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(33) (2R,6S,13aS,14aR,16aS,Z)-N-(cyclopropylsulfonyl)-5,16-dioxo-2-(phenanthridin-6-yloxy)-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(34) (2R,6S,13 aS,14aR,16aS,Z)-N-(cyclopropylsulfonyl)-6-(1-methyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(35) (2R,6S,13aS,14aR,16aS,Z)-N-(cyclopropylsulfonyl)-6-(2-hydroxy-2-methylpropanamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(36) (2R,6S,13aS,14aR,16aS,Z)-N-(cyclopropylsulfonyl)-6-(1,5-dimethyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(37) Cyclopentyl (2R,6S,13aS,14aR,16aS,Z)-14a-(cyclopropylsulfonylcarbamoyl)-2-(2-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate;

(38) tert-Butyl (2R,6S,13aS,14aR,16aS,Z)-14a-(cyclopropylsulfonylcarbamoyl)-2-(2,9-difluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate;

(39) tert-butyl (2R,6S,13aR,14aR,16aS)-14a-(cyclopropylsulfonylcarbamoyl)-5,16-dioxo-2-(phenanthridin-6-yloxy)octadecahydrocyclopropa[e]pyrrolo[1,2-a][1,4]diazacyclopentadecin-6-ylcarbamate;

(40) Cyclopentyl (2R,6S,13aR,14aR,16aS)-14a-(cyclopropylsulfonylcarbamoyl)-5,16-dioxo-2-(phenanthridin-6-yloxy)octadecahydrocyclopropa[e]pyrrolo[1,2-a][1,4]diazacyclopentadecin-6-ylcarbamate;

(41) tert-Butyl (2R,6S,13aR,14aR,16aS)-5,16-dioxo-2-(phenanthridin-6-yloxy)-14a-(thiophen-2-ylsulfonylcarbamoyl)octadecahydrocyclopropa[e]pyrrolo[1,2-a][1,4]diazacyclopentadecin-6-ylcarbamate;

(42) (2R,6S,13aS,14aR,16aS,Z)-N-(cyclopropylsulfonyl)-6-(5-methyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(43) Cyclopentyl (1aR,3aS,5R,9S,16aS,Z)-1a-(cyclopropylsulfonylcarbamoyl)-5-(2-fluorophenanthridin-6-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecin-9-ylcarbamate;

(44) tert-butyl (1aR,3aS,5R,9S,16aS,Z)-1a-(cyclopropylsulfonylcarbamoyl)-5-(9-fluorophenanthridin-6-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecin-9-ylcarbamate;

(45) tert-butyl (1aR,3aS,5R,9S,16aS,Z)-1a-(cyclopropylsulfonylcarbamoyl)-5-(8-fluorophenanthridin-6-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecin-9-ylcarbamate;

(46) (1aR,3aS,5R,9S,16aR,Z)-5-(3-(benzo[d]thiazol-2-yl)quinoxalin-2-yloxy)-N-(cyclopropylsulfonyl)-9-(isonicotinamido)-3,8-dioxo-1,1a,2,3,3a,4,5,6,8,9,10,11,12,13,14,16a-hexadecahydrocyclopropa[e]pyrrolo[1,2-a][1,4]diazacyclopentadecine-1a-carboxamide;

(47) (1aR,3aS,5R,9S,16aR,Z)-5-(3-(benzo[d]thiazol-2-yl)quinoxalin-2-yloxy)-N-(cyclopropylsulfonyl)-9-(5-methylpyrazine-2-carboxamido)-3,8-dioxo-1,1a,2,3,3a,4,5,6,8,9,10,11,12,13,14,16a-hexadecahydrocyclopropa[e]pyrrolo[1,2-a][1,4]diazacyclopentadecine-1a-carboxamide;

(48) cyclopentyl (2R,6S,13aR,14aR,16aS)-14a-(cyclopropylsulfonylcarbamoyl)-5,16-dioxo-2-(phenanthridin-6-yloxy)octadecahydrocyclopropa[e]pyrrolo[1,2-a][1,4]diazacyclopentadecin-6-ylcarbamate;

(49) tert-butyl (1aR,3aS,5R,9S,16aS,Z)-1a-(cyclopropylsulfonylcarbamoyl)-5-(2,9-difluorophenanthridin-6-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecin-9-ylcarbamate;

(50) tert-butyl (1aR,3aS,5R,9S,16aS,Z)-1a-(cyclopropylsulfonylcarbamoyl)-5-(2,10-difluorophenanthridin-6-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecin-9-ylcarbamate;

(51) tert-butyl (1aR,3aS,5R,9S,16aR,Z)-1a-(cyclopropylsulfonylcarbamoyl)-5-(3-(naphthalen-2-yl)quinoxalin-2-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecin-9-ylcarbamate;

(52) tert-butyl (1aR,3aS,5R,9S,16aR,Z)-1a-(cyclopropylsulfonylcarbamoyl)-5-(3-(naphthalen-1-yl)quinoxalin-2-yloxy)-3,8-dioxo-1,1a,2,3,3a,4,5,6,8,9,10,11,12,13,14,16a-hexadecahydrocyclopropa[e]pyrrolo[1,2-a][1,4]diazacyclopentadecin-9-ylcarbamate;

(53) tert-butyl (1aR,3aS,5R,9S,16aR,Z)-5-(3-(1H-indol-5-yl)quinoxalin-2-yloxy)-1a-(cyclopropylsulfonylcarbamoyl)-3,8-dioxo-1,1a,2,3,3a,4,5,6,8,9,10,11,12,13,14,16a-hexadecahydrocyclopropa[e]pyrrolo[1,2-a][1,4]diazacyclopentadecin-9-ylcarbamate;

(54) tert-butyl (1aR,3aS,5R,9S,16aR,Z)-5-(3-(1H-indol-6-yl)quinoxalin-2-yloxy)-1a-(cyclopropylsulfonylcarbamoyl)-3,8-dioxo-1,1a,2,3,3a,4,5,6,8,9,10,11,12,13,14,16a-hexadecahydrocyclopropa[e]pyrrolo[1,2-a][1,4]diazacyclopentadecin-9-ylcarbamate;

(55) tert-butyl (1aR,3aS,5R,9S,16aR,Z)-1a-(cyclopropylsulfonylcarbamoyl)-3,8-dioxo-5-(3-(quinolin-3-yl)quinoxalin-2-yloxy)-1,1a,2,3,3a,4,5,6,8,9,10,11,12,13,14,16a-hexadecahydrocyclopropa[e]pyrrolo[1,2-a][1,4]diazacyclopentadecin-9-ylcarbamate;

(56) tert-butyl (1aR,3aS,5R,9S,16aR,Z)-5-(3-(benzo[d][1,3]dioxol-5-yl)quinoxalin-2-yloxy)-1a-(cyclopropylsulfonylcarbamoyl)-3,8-dioxo-1,1a,2,3,3a,4,5,6,8,9,10,11,12,13,14,16a-hexadecahydrocyclopropa[e]pyrrolo[1,2-a][1,4]diazacyclopentadecin-9-ylcarbamate;

(57) (1aR,3aS,5R,9S,16aR,Z)-5-(3-(benzo[b]thiophen-2-yl)quinoxalin-2-yloxy)-N-(cyclopropylsulfonyl)-9-(5-methylpyrazine-2-carboxamido)-3,8-dioxo-1,1a,2,3,3a,4,5,6,8,9,10,11,12,13,14,16a-hexadecahydrocyclopropa[e]pyrrolo[1,2-a][1,4]diazacyclopentadecine-1a-carboxamide; and

(58) tert-butyl (1aR,3aS,5R,9S,16aS,Z)-1a-(cyclopropylsulfonylcarbamoyl)-3,8-dioxo-5-(thiazolo[4,5-c]quinolin-4-yloxy)-1,1a,2,3,3a,4,5,6,8,9,10,11,12,13,14,16a-hexadecahydrocyclopropa[e]pyrrolo[1,2-a][1,4]
diazacyclopentadecin-9-ylcarbamate; and

(59) tert-Butyl (2R,6S,13aS,14aR,16aS,Z)-14a-(cyclopropylsulfonylcarbamoyl)-2-(3,9-difluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

In another aspect, the invention provides a pharmaceutical composition comprising a therapeutically effective amount of a compound of formula I or I' described herein, or the embodiments described above, or a pharmaceutically acceptable salt, ester, or prodrug thereof, in combination with a pharmaceutically acceptable carrier or excipient.

According to another embodiment, the pharmaceutical compositions of the present invention may further contain one or more other anti-HCV agents. Examples of anti-HCV agents include, but are not limited to, α-interferon; β-interferon; pegylated interferon-α; pegylated interferon-lambda; ribavirin; viramidine; R-5158; nitazoxanide; amantadine; Debio-025, NIM-811; HCV polymerase inhibitors such as R7128, R1626, R4048, T-1106, PSI-7851, PF-00868554, ANA-598, IDX184, IDX102, IDX375, GS-9190, VCH-759, VCH-916, MK-3281, BCX-4678, MK-3281, VBY708, ANA598, GL59728 or GL60667; BMS-790052; BMS-791325; BMS-650032; HCV entry, helicase or internal ribosome entry site inhibitors; or other HCV replication inhibitors such as GS-9132, ACH-1095, AP-H005, A-831, A-689, AZD2836. For further details see S. Tan, A. Pause, Y. Shi, N. Sonenberg, Hepatitis C Therapeutics: Current Status and Emerging Strategies, *Nature Rev. Drug Discov.*, 1, 867-881 (2002); WO 00/59929 (2000); WO 99/07733 (1999); WO 00/09543 (2000); WO 99/50230 (1999); U.S. Pat. No. 5,861,297 (1999); and US2002/0037998 (2002).

According to an additional embodiment, the pharmaceutical compositions of the present invention may further contain another HCV protease inhibitor, such as telaprevir, boceprevir, ITMN-191, BI-201335, TMC-435, MK-7009, VBY-376, VX-500, VX-813, PHX-B, ACH-1625, IDX136, or IDX316.

In other embodiments, the invention provides a pharmaceutical composition further comprising pegylated interferon, another anti-viral, anti-bacterial, anti-fungal or anti-cancer agent, or an immune modulator, and/or further comprising a cytochrome P450 monooxygenase inhibitor or a pharmaceutically acceptable salt thereof. In certain embodiments, the cytochrome P450 monooxygenase inhibitor is ritonavir.

In another aspect, the invention provides for the use of a compound of the invention to manufacture an agent for preventing or treating viral infection. In another aspect, the invention provides for the use of a compound of the invention to manufacture an agent for preventing or treating hepatitis C infection. The present invention also contemplates the use of a solvate (e.g., hydrate) of a compound of the invention to manufacture pharmaceutical compositions for preventing or treating hepatitis C infection. As used herein, "solvate" refers to the physical association of a compound of the invention with one or more solvent molecule, whether organic or inorganic. This physical association often includes hydrogen bonding. In certain instances, the solvate is capable of isolation, for example, when one or more solvate molecules are incorporated in the crystal lattice of the crystalline solid.

In another embodiment, the compounds or pharmaceutical compositions of the invention are administered with ritonavir, either simultaneously or sequentially. In certain embodiments, a compound or a pharmaceutical composition of the invention is administered in the same composition as ritonavir. In another embodiment, a compound or a pharmaceutical composition thereof of the invention is administered in a different composition than ritonavir.

According to yet another embodiment, the pharmaceutical compositions of the present invention may further comprise inhibitor(s) of other targets in the HCV life cycle, including, but not limited to, helicase, polymerase, metalloprotease, CD81, NS5A, cyclophilin, and internal ribosome entry site (IRES).

In one aspect, the invention provides a method of treating a viral infection in a subject, comprising administering to the subject a therapeutically effective amount of a compound of formula I or I' described herein, or a pharmaceutically acceptable salt, ester or prodrug thereof, or a pharmaceutical composition comprising the same.

According to a further embodiment, the present invention includes methods of treating hepatitis C infections in a subject in need of such treatment by administering to said subject an anti-HCV virally effective amount or an inhibitory amount of the compounds or pharmaceutical compositions of the present invention.

According to another embodiment, the present invention includes methods of treating hepatitis C infections in a subject in need of such treatment by administering to said subject a compound or a pharmaceutical composition of the present invention. The methods can further include administration of an additional therapeutic agent, including another antiviral agent or an anti-HCV agent as described hereinabove. The additional agent can be co-administered (such as concurrently administered or sequentially administered) with a compound (a pharmaceutically acceptable salt, ester or prodrug thereof) or a pharmaceutical composition of the present invention. The additional agent(s) and a compound (or a pharmaceutically acceptable salt, ester or prodrug thereof) of the present invention can be formulated in the same composition, or in different compositions but co-administered concurrently or sequentially. The methods herein can further include the step of identifying that the subject is in need of treatment for hepatitis C infection. The identification can be by subjective (e.g., health care provider determination) or objective (e.g., diagnostic test) means.

In one aspect, the invention provides a method of inhibiting the replication of hepatitis C virus, the method comprising contacting a hepatitis C virus with an effective amount of a compound or pharmaceutical composition of the invention.

In another embodiment, the invention provides a method as described above, further comprising administering an additional anti-hepatitis C virus agent. Examples of anti-hepatitis C virus agents include, but are not limited to, α-interferon; β-interferon; pegylated interferon-α; pegylated interferon-lambda; ribavirin; viramidine; R-5158; nitazoxanide; amantadine; Debio-025, NIM-811; HCV polymerase inhibitors such as R7128, R1626, R4048, T-1106, PSI-7851, PF-00868554, ANA-598, IDX184, IDX102, IDX375, GS-9190, VCH-759, VCH-916, MK-3281, BCX-4678, MK-3281, VBY708, ANA598, GL59728 or GL60667; BMS-790052; BMS-791325; BMS-650032; HCV entry, helicase or internal ribosome entry site inhibitors; or other HCV replication inhibitors such as GS-9132, ACH-1095, AP-H005, A-831, A-689, AZD2836. For further details see S. Tan, A. Pause, Y. Shi, N. Sonenberg, Hepatitis C Therapeutics: Current Status and Emerging Strategies, *Nature Rev. Drug Discov.*, 1, 867-881 (2002); WO 00/59929 (2000); WO 99/07733 (1999); WO 00/09543 (2000); WO 99/50230 (1999); U.S. Pat. No. 5,861,297 (1999); and US2002/0037998 (2002). Preferably, a compound or a pharmaceutical composition of the present invention is co-administered with, or used in combination with, pegylated interferon (e.g., pegylated interferon alpha-2a or 2b) and ribavirin. Ritonavir or another cytochrome P450 monooxygenase inhibitor can also be used to enhance the pharmacokinetics of the compound of the present invention. The patient being treated is preferably infected with HCV genotype-1 (e.g., genotype 1a or 1b). Patients infected with other HCV genotypes, such as genotypes 2, 3, 4, 5 or 6, can also be treated with a compound or a pharmaceutical composition of the present invention.

In another embodiment, the invention provides a method as described above, further comprising administering another HCV protease inhibitor, an HCV polymerase inhibitor, an HCV helicase inhibitor, or an internal ribosome entry site (IRES)inhibitor, such as telaprevir, boceprevir, ITMN-191, BI-201335, TMC-435, MK-7009, VBY-376, VX-500, VX-813, PHX-B, ACH-1625, IDX136, IDX316, pegylated interferon, another anti-viral, anti-bacterial, anti-fungal or anti-cancer agent, or an immune modulator, and/or further comprising a cytochrome P450 monooxygenase inhibitor or a pharmaceutically acceptable salt thereof In certain embodiments, the cytochrome P450 monooxygenase inhibitor is ritonavir.

An additional embodiment of the present invention includes methods of treating biological samples by contacting the biological samples with the compounds of the present invention.

Yet another aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group. The number of carbon atoms in a hydrocarbyl substituent can be indicated by the prefix "$C_x$-$C_y$," where x is the minimum and y is the maximum number of carbon atoms in the substituent.

The prefix "halo" indicates that the substituent to which the prefix is attached is substituted with one or more independently selected halogen radicals. For example, "haloalkyl" means an alkyl substituent wherein at least one hydrogen radical is replaced with a halogen radical.

If a linking element in a depicted structure is "absent", then the left element in the depicted structure is directly linked to the right element in the depicted structure. For example, if a chemical structure is depicted as X-L-Y wherein L is absent, then the chemical structure is X—Y.

The term "alkyl" as used herein, refers to a saturated, straight- or branched-chain hydrocarbon radical typically containing from 1 to 20 carbon atoms. For example, "$C_1$-$C_6$ alkyl" or "$C_1$-$C_8$ alkyl" contains from one to six, or from one to eight, carbon atoms, respectively. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds and typically from 2 to 20 carbon atoms. For example, "$C_2$-$C_6$ alkenyl" or "$C_2$-$C_8$ alkenyl" contains from two to six, or from two to eight carbon atoms, respectively. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds and typically from 2 to 20 carbon atoms. For example, "$C_2$-$C_6$ alkynyl" or "$C_2$-$C_8$ alkynyl" contains from two to six, or from two to eight, carbon atoms, respectively. Representative alkynyl groups include, but are not limited to, for example, ethynyl, 1-propynyl, 1-butynyl, heptynyl, octynyl and the like.

The term "alkylene" refers to a divalent group derived from a straight or branched saturated hydrocarbyl chain typically containing from 1 to 20 carbon atoms, more typically from 1 to 8 carbon atoms, and even more typically from 1 to 6 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkenylene" refers to a divalent unsaturated hydrocarbyl group which may be linear or branched and which has at least one carbon-carbon double bond. An alkenylene group typically contains 2 to 20 carbon atoms, more typically from 2 to 8 carbon atoms, and even more typically from 2 to 6 carbon atoms. Non-limiting examples of alkenylene groups include —C(H)=C(H)—, —C(H)=C(H)—$CH_2$—, —C(H)=C(H)—$CH_2$—$CH_2$—, —$CH_2$—C(H)=C(H)—$CH_2$—, —C(H)=C(H)—CH($CH_3$)—, and —$CH_2$—C(H)=C(H)—CH($CH_2CH_3$)—.

The term "alkynylene" refers to a divalent unsaturated hydrocarbon group which may be linear or branched and which has at least one carbon-carbon triple bond. Representative alkynylene groups include, by way of example, —C≡C—, —C≡C—$CH_2$—, —C≡C—$CH_2$—$CH_2$—, —$CH_2$—C≡C—$CH_2$—, —C≡C—CH($CH_3$)—, and —$CH_2$—C≡C—CH($CH_2CH_3$)—.

The term "cycloalkyl" denotes a monovalent group derived from a monocyclic or polycyclic saturated carbocyclic ring compound. Examples of cycloalkyl include, but not limited to, cyclopropyl, cyclobutyl, cyclopentyl, cyclohexyl, bicyclo[2.2.1]heptyl, and bicyclo[2.2.2]octyl and the like.

The terms "carbocycle" or "carbocyclic" or "carbocyclyl" refer to a saturated (e.g., "cycloalkyl"), partially saturated (e.g., "cycloalkenyl" or "cycloalkynyl") or completely unsaturated (e.g., "aryl") ring system containing zero heteroatom ring atom and typically from 3 to 18 carbon ring atoms. A carbocyclyl may be, without limitation, a single ring, or two or more fused rings, or bridged or spiro rings. A carbocyclyl may contain, for example, from 3 to 14 ring members (i.e., $C_3$-$C_{14}$carbocyclyl, such as $C_3$-$C_{14}$cycloalkyl), from 3 to 10 ring members (i.e., $C_3$-$C_{10}$carbocyclyl, such as $C_3$-$C_{10}$cycloalkyl), from 3 to 8 ring members (i.e., $C_3$-$C_8$carbocyclyl, such as $C_3$-$C_8$cycloalkyl), or from 3 to 6 ring members (i.e., $C_3$-$C_6$carbocyclyl, such as $C_3$-$C_6$cycloalkyl). A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, fluorenyl, indanyl, 1,2,3,4-tetrahydro-naphthyl, indenyl, isoindenyl, bicyclodecanyl, anthracenyl, phenanthrene, benzonaphthenyl (also known as "phenalenyl"), decalinyl, and norpinanyl and the like. A carbocyclyl group can be attached to the parent molecular moiety through any substitutable carbon atom of the group.

The term "aryl" refers to an aromatic carbocyclyl containing from 6 to 14 carbon ring atoms. Non-limiting examples of aryls include phenyl, naphthalenyl, anthracenyl, and indenyl and the like. An aryl group can be connected to the parent molecular moiety through any substitutable carbon atom of the group.

The term "aralkyl" or "arylalkyl" refers to an alkyl residue attached to an aryl ring. Examples of aralkyl include, but are not limited to, benzyl, phenethyl and the like.

The term "heteroaryl" means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heteroaralkyl" or "heteroarylalkyl" refers to an alkyl residue attached to a heteroaryl ring. Examples include, but are not limited to, pyridinylmethyl, pyrimidinylethyl and the like.

The term "heterocycloalkyl" refers to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

The terms "heterocyclic" or "heterocyclo" or "heterocyclyl" refer to a saturated (e.g., "heterocycloalkyl"), partially unsaturated (e.g., "heterocycloalkenyl" or "heterocycloalkynyl") or completely unsaturated (e.g., "heteroaryl") ring system typically containing from 3 to 18 ring atoms, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results. A heterocyclyl may be, without limitation, a single ring, which typically contains from 3 to 14 ring atoms, from 3 to 8 ring atoms, from 3 to 6 ring atoms, or from 5 to 6 ring atoms. Non-limiting examples of single-ring heterocyclyls include furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, or diazepinyl. A heterocyclyl may also include, without limitation, two or more rings fused together, such as, for example, naphthyridinyl, thiazolpyrimidinyl, thienopyrimidinyl, pyrimidopyrimidinyl, or pyridopyrimidinyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

The terms "optionally substituted", "optionally substituted alkyl," "optionally substituted "optionally substituted alkenyl," "optionally substituted alkynyl", "optionally substituted carbocyclic," "optionally substituted aryl", " optionally substituted heteroaryl," "optionally substituted heterocyclic," and any other optionally substituted group as used herein, refer to groups that are substituted or unsubstituted by independent replacement of one, two, or three or more of the hydrogen atoms thereon with substituents including, but not limited to:

—F, —Cl, —Br, —I,

—OH, protected hydroxy, alkoxy, oxo, thiooxo,

—$NO_2$, —CN, $CF_3$, $N_3$,

—$NH_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl, —$CONH_2$, —CONH-alkyl, —CONH-alkenyl, —CONH-alkynyl, —CONH-cycloalkyl, —CONH-aryl, —CONH-heteroaryl, —CONH-heterocycloalkyl, —$OCO_2$-alkyl, —$OCO_2$-alkenyl, —$OCO_2$-alkynyl, —$OCO_2$-cycloalkyl, —$OCO_2$-aryl, —$OCO_2$-heteroaryl, —$OCO_2$-heterocycloalkyl, —$OCONH_2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —$NHCO_2$-alkyl, —$NHCO_2$-alkenyl, —$NHCO_2$-alkynyl, —$NHCO_2$-cycloalkyl, —$NHCO_2$-aryl, —$NHCO_2$-heteroaryl, —$NHCO_2$-heterocycloalkyl, —NHC(O)$NH_2$, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, NHC(S)$NH_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —NHC(NH)$NH_2$, —NHC(NH)NH-alkyl, —NHC(NH)NH-alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl-$SO_2NH_2$, —$SO_2$NH-alkyl, —$SO_2$NH-alkenyl, —$SO_2$NH-alkynyl, —$SO_2$NH-cycloalkyl, —$SO_2$NH-aryl, —$SO_2$NH-heteroaryl, —$SO_2$NH-heterocycloalkyl, —$NHSO_2$-alkyl, —$NHSO_2$-alkenyl, —$NHSO_2$-alkynyl, —$NHSO_2$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

It is understood that the aryls, heteroaryls, carbocyclics, heterocyclics, alkyls, and the like can be further substituted.

The terms "halo" and "halogen," as used herein, refer to an atom selected from fluorine, chlorine, bromine and iodine.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "leaving group," or "LG", as used herein, refers to any group that leaves in the course of a chemical reaction involving the group and includes but is not limited to halogen, brosylate, mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, Protective Groups in Organic Synthesis, 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, Protective Groups in Organic Synthesis, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "alkylamino" refers to a group having the structure —N(R$_a$R$_b$), where R$_a$ and R$_b$ are independent H or alkyl.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water, alcohol or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, polysorbate, dimethylformamide, oils (in particular, cottonseed, groundnut, corn, germ, olive, castor, and sesame oils), mono- or di-glycerides, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, antioxidants, sweetening, flavoring, and perfuming agents. The liquid dosage form can also be encapsulated in a gelatin capsule, wherein a compound of the present invention can be dissolved in a pharmaceutically acceptable carrier containing, for example, one or more solubilizating agents (e.g., polysorbate 80 and mono and diglycerides), and other suitable excipients (e.g., an antioxidants such as ascorbyl palmitate, or a sweetening or flavoring agent).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Immediate release forms are also contemplated by the present invention.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, viral infections are treated or prevented in a subject, such as a human or another animal, by administering to the subject a therapeutically effective amount of a compound of the invention (or a pharmaceutically acceptable salt, ester or prodrug thereof), in such amounts and for such time as is necessary to achieve the desired result. The term "therapeutically effective amount" of a compound of the invention, as used herein, means a sufficient amount of the compound so as to decrease the viral load in a subject and/or decrease the subject's HCV symptoms. As is well understood in the medical arts a therapeutically effective amount of a compound of this invention will be at a reasonable benefit/risk ratio applicable to any medical treatment.

Antiviral Activity

An inhibitory amount or dose of the compounds of the present invention may range from about 0.1 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a subject such as a human or lower mammal by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "anti-hepatitis C virally effective amount" of a compound of the invention, as used herein, means a sufficient amount of the compound so as to decrease the viral load in a biological sample or in a subject. As well understood in the medical arts, an anti-hepatitis C virally effective amount of a compound of this invention will be at a reasonable benefit/risk ratio applicable to any medical treatment.

The term "inhibitory amount" of a compound of the present invention means a sufficient amount to decrease the hepatitis C viral load in a biological sample or a subject. It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells. Thus, another embodiment of the present invention is a method of treating a biological sample by contacting said biological sample with an inhibitory amount of a compound or pharmaceutical composition of the present invention.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present invention comprise administration to a patient in need of such treatment from about 10 mg to about 1000 mg of the compound(s) of this invention per day in single or multiple doses. In another embodiment, the treatment regimen comprises administration to a patient in need of such treatment from about 25 mg to about 6000 mg of a compound(s) of this invention per day in single or multiple doses, either with or without a cytochrome P450 monooxygenase inhibitor such as ritonavir. The suitable daily dose for the co-administered cytochrome P450 monooxygenase inhibitor (e.g., ritonavir) can range, without limitation, from 10 to 200 mg. Preferably, a compound(s) of the present invention, or a combination of a compound(s) of the invention and ritonavir, is administered once daily or twice daily to achieve the desired daily dose amount. For instance, when used without ritonavir, a compound of the present invention can be administered to a patient twice a day with a total daily dose of 4000, 4200, 4400, 4600, 4800 or 5000 mg. For another instance, when used in combination with ritonavir, a compound of the present invention can be administered to a patient once or twice a day with a total daily dose of 200, 400, 600 or 800 mg, where the amount of ritonavir can be 25, 50 or 100 mg per administration.

Synthetic Methods

The compounds and processes of the present invention will be better understood in connection with the following synthetic schemes that illustrate the methods by which the compounds of the invention may be prepared.

Definitions of variables in the structures in the schemes herein are commensurate with those of corresponding positions in the formulae delineated herein.

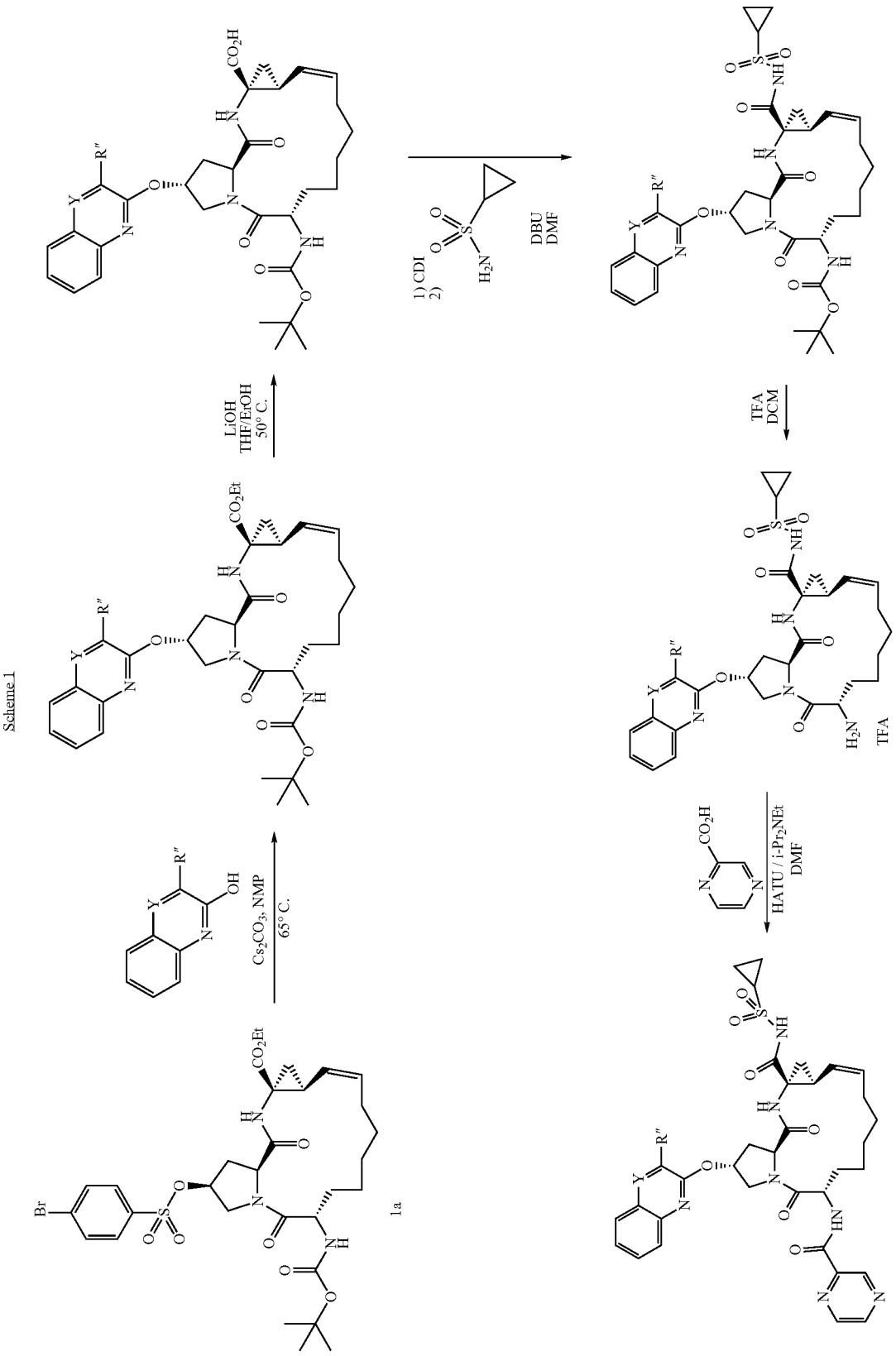

Scheme 1 describes the synthesis of various compounds of the invention. The starting material was displaced at the leaving groups by reaction with a nucleophile to provide a nucleophile substituted macrocycle. Base hydrolysis of the ester to the acid was followed by coupling of a sulfonamide derivative. The protected nitrogen was then deprotected and substituted with another group.

In one aspect, the invention provides a method of producing a compound of formula I, comprising the step of reacting a compound of formula II:

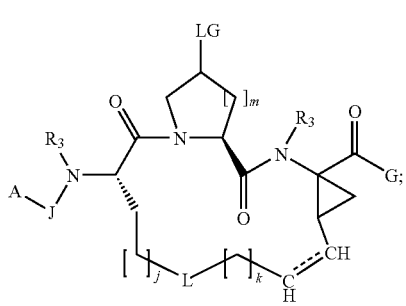

(II)

wherein,

J is absent, optionally substituted alkylene, optionally substituted alkenylene, optionally substituted alkynylene, —C(O)—, —O—C(O)—, —N($R_3$)—C(O)—, —C(S)—, —C(=$NR_4$)—, —S(O)—, —S($O_2$)—, or —N($R_3$)—;

A is optionally substituted alkyl, optionally substituted alkenyl, or optionally substituted alkynyl, each containing 0, 1, 2, or 3 heteroatoms selected from O, S, or N; optionally substituted aryl, optionally substituted arylalkyl, optionally substituted alkoxy, optionally substituted heteroaryl, optionally substituted heterocyclic, or optionally substituted carbocyclic;

G is -E-$R_5$;

wherein E is absent; optionally substituted alkylene, optionally substituted alkenylene, optionally substituted alkynylene, each containing 0, 1, 2, or 3 heteroatoms selected from O, S, or N; or —O—, —S—, —N($R_3$)—, —N($R_3$)S($O_p$)—, —N($R_3$)C(O)—, —N($R_3$)C(O)S($O_p$)—, —OS($O_p$)—, —C(O)S($O_p$)—, or —C(O)N($R_3$)S($O_p$)—;

p is 0, 1, or 2;

$R_5$ is H; optionally substituted alkyl, optionally substituted alkenyl, or optionally substituted alkynyl, each containing 0, 1, 2, or 3 heteroatoms selected from O, S, or N; optionally substituted carbocyclic, optionally substituted heterocyclic, optionally substituted aryl, or optionally substituted heteroaryl;

Each $R_3$ and $R_4$ is independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

L is absent or is selected from optionally substituted alkylene, optionally substituted alkenylene or optionally substituted alkynylene, each containing 0, 1, 2, or 3 heteroatoms selected from O, S, or N;

j=0, 1, 2, 3, or 4;

k=0, 1, 2, or 3;

m=0, 1, or 2;

n is 0, 1, 2, 3, or 4; and

═══ denotes a carbon-carbon single or double bond; and

LG is a leaving group;

with a compound of formula III:

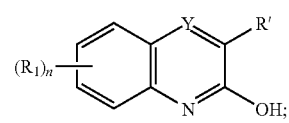

(III)

wherein:

Each $R_1$ is independently selected from (i) halogen, hydroxy, amino, —CN, —$CF_3$, —$N_3$, —$NO_2$, —$O_4$, —$SR_4$, —$SOR_4$, —$SO_2R_4$, —N($R_3$)S(O)$_2$—$R_4$, —N($R_3$)($SO_2$)$NR_3R_4$, —$NR_3R_4$, —C(O)$OR_4$, —C(O)$R_4$, —C(O)$NR_3R_4$, or —N($R_3$)C(O)$R_4$;

(ii) optionally substituted aryl;

(iii) optionally substituted heteroaryl;

(iv) optionally substituted heterocyclic;

(v) optionally substituted carbocyclic; or (vi) optionally substituted alkyl, optionally substituted alkenyl, or optionally substituted alkynyl, each containing 0, 1, 2, or 3 heteroatoms selected from O, S, or N;

$R_3$ and $R_4$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

Y is N or C(R");

wherein if Y is N, then R' is optionally substituted heterocyclic, optionally substituted heteroaryl, optionally substituted aryl or optionally substituted carbocyclic, and comprises two or more fused rings, and wherein R' is not

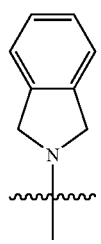 [SMILES: *N1Cc2ccccc2C1]

or

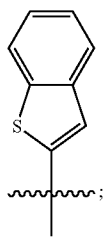 [SMILES: *c1cc2ccccc2s1]

further provided that said compound is not tert-butyl (2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate;

wherein if Y is —C(R")—, then R' and R" taken together with the carbon atoms to which they are attached form an aryl or heteroaryl ring, each said ring is optionally substituted;

wherein A, $R_1$, R' and/or R" can be taken together to form a ring; to thereby produce a compound of formula I or I'.

A compound of formula I can also be prepared according to the process depicted in Scheme 2, wherein A, J, L, G, Y, R' $R_1$, $R_3$, n, m, j, and k are defined hereinabove, and

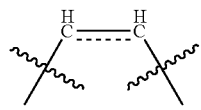

is

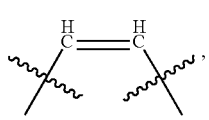 [SMILES: */C=C\*]

and wherein Q is halogen or a leaving group, PG and $PG_N$ are each independently an amino protecting group, and $PG_C$ is a carboxylic acid protecting group. Compound (b) can be prepared by reacting

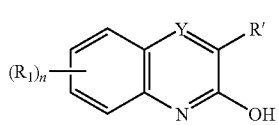

with a halogenation agent such as $POCl_3$. Non-limiting examples of amino protecting group include $C_1$-$C_6$alkoxycarbonyl (e.g., tert-butoxycarbonyl or Boc), carboxybenzyl, p-methoxybenzyl carbonyl, 9-fluorenylmethyloxycarbonyl, benzyl, p-methoxybenzyl, 3,4-dimethoxybenzyl, p-methoxyphenyl, benzoyl, or tosyl or other suitable sulfonamides. Non-limiting examples of carboxylic acid protecting group include $C_1$-$C_6$alkyl (e.g., tert-butyl, methyl or ethyl), benzyl, or silyl, all of which protect carboxylic acid moieties in the form of esters.

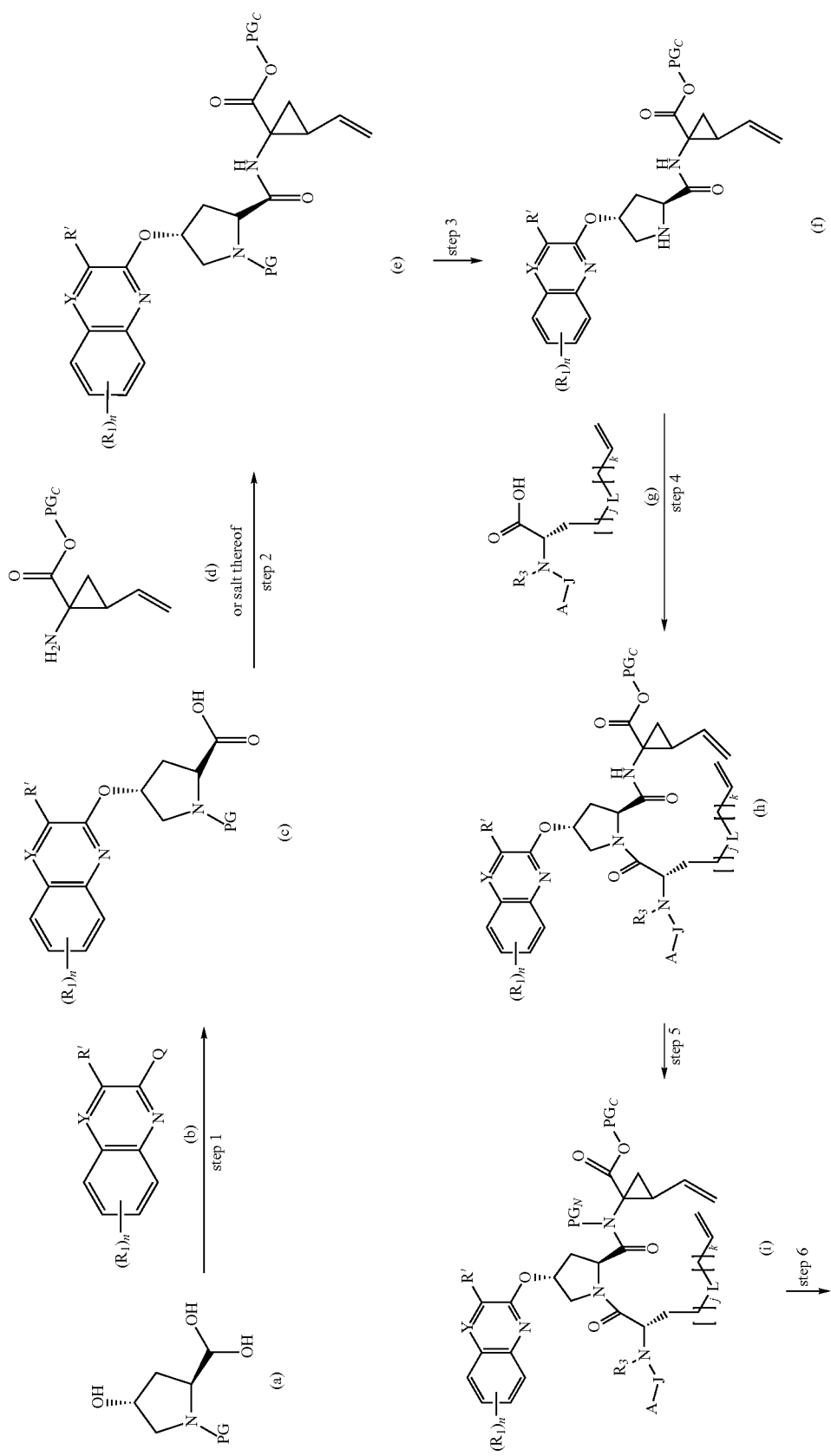

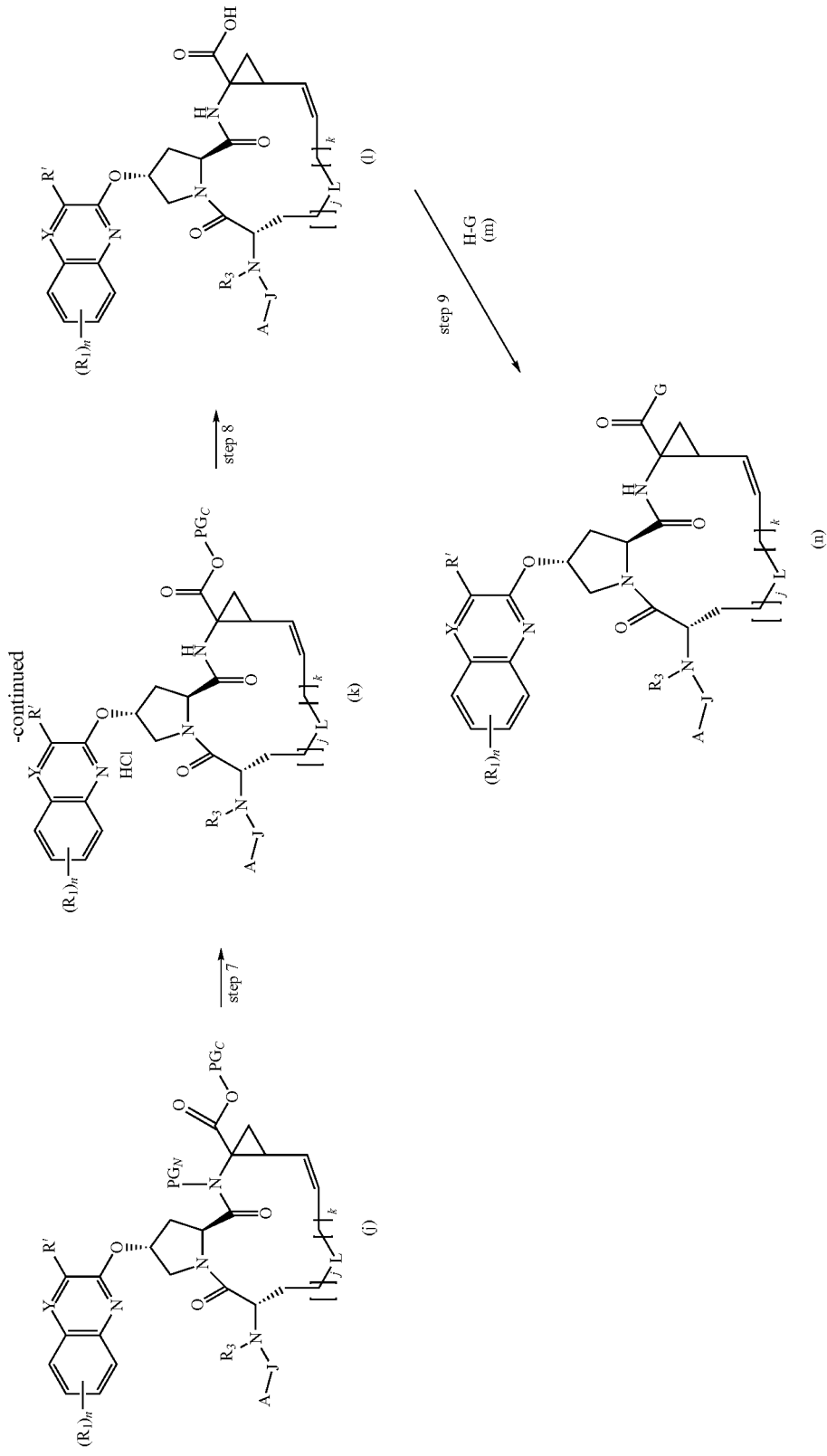

In step 1, compound (a) reacts with compound (b) to form compound (c), where the reaction can be conducted, as a non-limiting example, in the presence of sodium tert-butoxide or potassium tert-butoxide. Preferably, the reaction is conducted in the absence of lanthanum chloride. Also preferably, the yield of this reaction is at least 50%. More preferably, the yield of the reaction is at least 60%, 70%, or 80%. Highly preferably, the yield of the reaction is at least 90% or 95%. Preferred PG is $C_1$-$C_6$alkoxycarbonyl, such as tert-butoxycarbonyl or Boc.

Compound (c) can then be reacted with compound (d), or a salt thereof such as TsOH salt, to form compound (e) (step 2), followed by de-protection of the amino group to create compound (0 or a salt thereof (e.g., HCl salt) (step 3). Preferred $PG_C$ includes, but is not limited to, $C_1$-$C_6$alkyl such as ethyl. Compound (f) can then be reacted with compound (g) to form compound (h) (step 4), which is subsequently amino-protected to form compound (i) (step 5) and then subjected to ring-closing metathesis to form compound (j) (step 6). Preferred $PG_N$ includes, but is not limited to, $C_1$-$C_6$alkoxycarbonyl, such as tert-butoxycarbonyl or Boc. General processes for ring-closing metathesis (RCM) are well known in the art. Preferred processes involve the use of transition metal catalysts, such as those described in U.S. Pat. No. 6,921,753 and U.S. Patent Application Publication No. 20070043180. Non-limiting examples of suitable catalysts include Zhan Catalyst-1 B

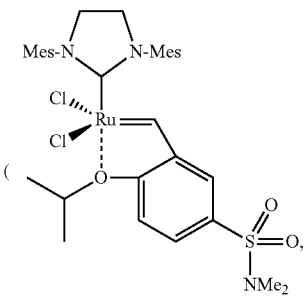

where Mes is 2,4,6-trimethylphenyl; also known as Zhan-B) and Zhan Catalyst-1C

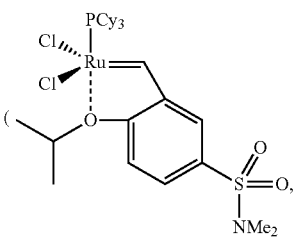

where Cy is cyclohexyl), both of which are commercially available from Zannan Pharma, Ltd. (Shanghai, China). De-protection of the amino moiety in compound (j) leads to compound (k) (or its free-base) (step 7). In certain cases, compound (h) can directly undergo the ring-closing metathesis reaction to make compound (k) (or its free-base), without the amino protecting and de-protecting steps.

The carboxylic acid moiety in compound (k) can then be deprotected to form compound (1) (step 8), which reacts with compound (m) to form compound (n) (step 9). G in compound (m) is defined as -E-$R_5$, wherein E and $R_5$ are defined hereinabove.

A compound of formula I', as described herein, can be similarly prepared according to Scheme 2.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The compounds and processes of the present invention will be better understood in connection with the following examples, which are intended as an illustration only and not to limit the scope of the invention. The following examples can be prepared according to either Scheme 1 or Scheme 2 as described above. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1 tert-butyl (2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

Example 1a (2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate A solution of (2S,6S,13aS,14aR,16aS,Z)-ethyl 6-(tert-butoxycarbonylamino)-2-hydroxy-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate and DABCO in toluene was stirred at room temperature (rt). To this solution was added a solution of 4-bromobenzene-1-sulfonyl chloride in toluene. After the addition was complete the reaction mixture was quenched with 10% aqueous sodium carbonate and the mixture stirred for 15 min. Tetrahydrofuran was added and the mixture was washed with 0.5 M HCl, water, and then saturated aqueous sodium chloride. The organic layer was dried over anhydrous magnesium sulfate, filtered, and evaporated under reduced pressure and dried to provide the title compound.

Example 1b (2R,6S,13aR,14aR,16aS,Z)-ethyl 6-(tert-butoxycarbonylamino)-2-(3-chloroquinoxalin-2-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (1b)

To a solution of compound 1a (15.0 g, 21.0 mmol) in NMP (55 ml) was added 3-chloroquinoxalin-2-ol (4.56 g, 25.3 mmol) followed by $Cs_2CO_3$ (17.1 g, 52.6 mmol). The resulting mixture was heated to 70° C. for 18 hours. The reaction mixture was cooled to room temperature, and then partitioned between ethyl acetate (300 ml) and 1 N HCl (100 ml). The organic layer was separated, washed with brine (100 ml), dried over anhydrous magnesium sulfate, and concentrated under reduced pressure to obtain the crude product as a solid. The solid was purified by column chromatography on silica gel (EtOAc-hexane gradient) to obtain the title compound as a solid (6.2 g, 45% yield); MS(ESI): m/z=656.3 [M+H]

Example 1c (2R,6S,13aR,14aR,16aS,Z)-ethyl 6-(tert-butoxycarbonylamino)-5,16-dioxo-2-(3-phenylquinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylate (1c)

To a microwave vessel was added the product from 1b (700 mg, 1.07 mmole), 2-(tributylstannyl)benzo[d]thiazole (905 mg, 2.13 mmole), palladium-tetrakis(triphenylphosphine) (113 mg, 0.11 mmole) and dioxane (5 ml). The vessel was evacuated and nitrogen introduced, which was repeated twice. The mixture was reacted in a microwave reactor at 110 degrees C. for 1 hr. The reaction was diluted with MeCN and washed 3 times with hexane. The MeCN layer was evaporated and purified by column chromatography on silica gel (CHCl3-EtOAc gradient) to obtain the title compound (692 mg, 86% yield). MS(ESI): m/z=755.2 [M+H].

Example 1d (2R,6S,13aR,14aR,16aS,Z)-2-(3-(benzo[d]thiazol-2-yl)quinoxalin-2-yloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (1d)

To a solution of the product of Example 1c (692 mg, 0.95 mmol) in tetrahydrofuran (5 ml)/ethanol (2.5 ml)/water (2.5 ml) was added lithium hydroxide monohydrate (154 mg, 3.7 mmole). The resulting mixture was heated to 50° C. for one hour and cooled to room temperature. The organic solvents were mostly removed under reduced pressure, EtOAc (100 ml) was added and then washed with 1 N HCl (30 ml). The organic layer was separated, washed with brine (20 ml), dried over anhydrous $MgSO_4$, and concentrated under reduced pressure to afford 666 mg of product 1d.

Example 1f

To a solution of product of Example 1d (666 mg, 0.92 mmol) in 1,2-dichloroethane (9 ml) was added 1,1'-carbonyldiimidazole (246 mg, 1.52 mmol). The reaction mixture was stirred at 40 degrees C. for 2 hours. To the above solution was then added the cyclopropanesulfonamide (184 mg, 1.52 mmol) followed by DBU (0.23 ml, 1.52 mmol). The resulting mixture was stirred at 40 degrees C. for 1 hour. The reaction mixture was diluted with EtOAc (100 ml) and washed with 1 N HCl (20 ml.) then saturated sodium chloride (20 ml). The organic layer was separated, dried over anhydrous $MgSO_4$, filtered, and concentrated under reduced pressure. The residue was purified by column chromatography on silica gel ($CHCl_3$/EtOAc gradient) to obtain the title compound (322 mg, 38% yield). MS (ESI): m/z=830.0 [M+H].

Example 2

(2R,6S,13aS,14aR,16aS,Z)-2-(3-(benzo[d]thiazol-2-yl)quinoxalin-2-(cyclopropylsulfonyl)-6-(isonicotinamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide

Example 2a (2R,6S,13aS,14aR,16aS,Z)-6-amino-2-(3-(benzo[d]thiazol-2-yl)quinoxalin-2-yloxy)-N-(cyclopropylsulfonyl)-5,16-dioxo-1,2,3,5,6,7,8,9,10,11,13a,14,14a,15,16,16a-hexadecahydrocyclopropa[1,2-a][1,4]diazacyclopentadecine-14a-carboxamide To a suspension of the product of Example 1 (320 mg, 0.39 mmol) in EtOAc (3 mL) was added a 4 M solution of HCl in dioxane (1.9 mL, 7.7 mmol). The reaction mixture was stirred at room temperature for 20 h. The solvent was evaporated under reduced pressure and the resulting solid dried under vacuum to provide (2R,6S,13aR,14aR,16aS,Z)-6-amino-2-(3-(benzo[d]thiazol-2-yl)quinoxalin-2-yloxy)-N-(cyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide, Hydrochloric Acid (295 mg, quant. yield).

Example 2b

To a solution of Example 2a (28 mg, 0.037 mmol) in dichloromethane (0.5 mL) was added isonicotinic acid (5.0 mg, 0.040 mmol), HATU (16.7 mg, 0.044 mmol) and diisopropylethylamine (0.021 mL, 0.12 mmol). The reaction mixture was stirred at 25° C. for 2 hrs. and evaporated. Purification of the crude material via reverse phase chromatography eluting with acetonitrile/water/TFA provided the title compound.
MS (ESI): m/z=835.0 [M+H].

Example 3

(2R,6S,13aS,14aR,16aS,Z)-2-(3-(benzo[d]thiazol-2-yl)quinoxalin-2-yloxy)-N-(cyclopropylsulfonyl)-6-(2-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 3 was prepared according to the procedure utilized for the preparation of Example 2, replacing isonicotinic acid with 2-fluorobenzoic acid. Purification of the crude material via reverse phase chromatography eluting with acetonitrile/water/TFA provided the title compound.
MS (ESI): m/z=851.9 [M+H].

Example 4

N-((2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide Example 4 was prepared according to the procedure utilized for the preparation of Example 2, replacing isonicotinic acid with 5-methylisoxazole-3-carboxylic acid. Purification of the crude material via reverse phase chromatography eluting with acetonitrile/water/TFA provided the title compound.
MS (ESI): m/z=838.9 [M+H].

Example 5

(2R,6S,13aS,14aR,16aS,Z)-2-(3-(benzo[d]thiazol-2-yl)quinoxalin-2-yloxy-N-(cyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 5 was prepared according to the procedure utilized for the preparation of Example 2, replacing isonicotinic acid with 5-methylpyrazine-2-carboxylic acid. Purification of the crude material via reverse phase chromatography eluting with acetonitrile/water/TFA provided the title compound.
MS (ESI): m/z=849.9 [M+H].

Example 6

N-((2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-5-carboxamide Example 6 was prepared according to the procedure utilized for the preparation of Example 2, replacing isonicotinic acid with isoxazole-5-carboxylic acid. Purification of the crude material via reverse phase chromatography eluting with acetonitrile/water/TFA provided the title compound. MS (ESI): m/z=824.9 [M+H].

Example 7

N-((2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-4-carboxamide Example 7 was prepared according to the procedure utilized for the preparation of Example 2, replacing isonicotinic acid with thiazole-4-carboxylic acid. Purification of the crude material via reverse phase chromatography eluting with acetonitrile/water/TFA provided the title compound. MS (ESI): m/z=840.9 [M+H].

Example 8

(2R,6S,13aS,14aR,16aS,Z)-2-(3-(benzo[d]thiazol-2-yl)quinoxalin-2-(cyclopropylsulfonyl)-6-(1-methyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 8 was prepared according to the procedure utilized for the preparation of Example 2, replacing isonicotinic acid with 1-methyl-1H-pyrazole-3-carboxylic acid. Purification of the crude material via reverse phase chromatography eluting with acetonitrile/water/TFA provided the title compound. MS (ESI): m/z=838.0 [M+H].

Example 9

(2R,6S,13aS,14aR,16aS,Z)-2-(3-(benzo[d]thiazol-2-yl)quinoxalin-2-yloxy)-N-(cyclopropylsulfonyl)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 9 was prepared according to the procedure utilized for the preparation of Example 2, replacing isonicotinic acid with pyrimidine-4-carboxylic acid. Purification of the crude material via reverse phase chromatography eluting with acetonitrile/water/TFA provided the title compound. MS (ESI): m/z=835.9[M+H].

Example 10

(2R,6S,13aS,14aR,16aS,Z)-2-(3-(benzo[d]thiazol-2-yl)quinoxalin-2-yloxy)-N-(cyclopropylsulfonyl)-6-(1,3-dimethyl-1H-pyrazole-4-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 10 was prepared according to the procedure utilized for the preparation of Example 2, replacing isonicotinic acid with 1,3-dimethyl-1H-pyrazole-4-carboxylic acid. Purification of the crude material via reverse phase chromatography eluting with acetonitrile/water/TFA provided the title compound. MS (ESI): m/z=852.0[M+H].

Example 11

(2R,6S,13aS,14aR,16aS,Z)-2-(3-(benzo[d]thiazol-2-yl)quinoxalin-2-yloxy)-N-(cyclopropylsulfonyl)-6-(3-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 11 was prepared according to the procedure utilized for the preparation of Example 2, replacing isonicotinic acid with 3-fluorobenzoyl chloride. Purification of the crude material via reverse phase chromatography eluting with acetonitrile/water/TFA provided the title compound. MS (ESI): m/z=838.0 [M+H].

Example 12 tert-butyl (2R,6S,13aS,14aR,16aS,Z)-2-(3-(benzofuran-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Example 12a tert-butyl (2R,6S,13aS,14aR,16aS,Z)-14a-(cyclopropylsulfonylcarbamoyl)-2-hydroxy-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

To a solution of tert-butyl (2R,6S,13aS,14aR,16aS,Z)-2-(9H-fluoren-9-ylideneaminooxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate (20.0 g, 26.8 mmol) in acetic acid (80 ml) stirring at 40° C. was zinc dust (10.52 g, 166 mmol). After the addition was complete the reaction mixture was stirred at 40° C. for 1 hour. The mixture was then cooled to room temperature, diluted with toluene, and filtered through Celite. The mother liquor was washed with water, 1 N HCl, and saturated aqueous sodium chloride, dried over anhydrous magnesium sulfate and filtered. The filtrate was then evaporated under reduced pressure to provide the title compound 12a (14.8 g, 97% yield).

Example 12b tert-butyl (2R,6S,13aS,14aR,16aS,Z)-2-(3-chloroquinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate.

A solution of compound 12a (10.0 g, 17.6 mmol), cesium carbonate (17.2, 52.8 mmol), and 2,3-dichloroquinoxaline (3.50 g, 17.6 mmol) in dimethylformamide (175 ml) was heated to 70° C. for 18 hours. An additional portion of 2,3-dichloroquinoxaline (0.70 g, 3.5 mmol) was added and the reaction mixture was stirred at 70° C. for 18 hours. The reaction mixture was cooled to room temperature, and then partitioned between ethyl acetate (300 ml) and 1 N HCl (100 ml). The organic layer was separated, washed with brine (100 ml), dried over anhydrous magnesium sulfate, and concentrated under reduced pressure to obtain the crude product as a solid. The solid was purified by column chromatography on silica gel (EtOAc-hexane gradient) to obtain the title compound as a solid (4.7 g, 37% yield); MS(ESI): m/z=731.1 [M+H].

Example 12c

To a microwave vessel was added the product from 12b (0.40 g 0.547 mmole), benzofuran-2-yltributylstannane (0.245 g, 0.602 mmole), tris(dibenzylideneacetone)dipalladium(0) (50 mg, 0.055 mmol), 1,3,5,7-tetramethyl-2,4,8-trioxa-6-phenyl-6-phospha-adamantane (32 mg, 0.11 mmol), sodium bicarbonate (46 mg, 0.547 mmol) and dioxane (3 mL). The vessel was evacuated and nitrogen introduced. The mixture was reacted in a microwave reactor at 110 degrees C. for 1 hr. The reaction mixture was diluted with ethyl acetate, washed with 1 N HCl followed by saturated aqueous sodium chloride, and dried over anhydrous magnesium sulfate. The mixture was filtered through Celite and evaporated under reduced pressure. The residue was dissolved in acetonitrile and washed with hexane (five times) and then evaporated under reduced pressure. The residue was purified by column chromatography on silica gel (CHCl$_3$-EtOAc gradient) to obtain the title compound (386 mg, 87% yield). MS(ESI): m/z=813.0 [M+H].

Example 13

N-a2R,6S,13aS,14aR,16aS,Z)-2-(3-(benzofuran-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide

Example 13a (2R,6S,13aS,14aR,16aS,Z)-6-amino-2-(3-(benzofuran-2-yl)quinoxalin-2-yloxy)-N-(cyclopropylsulfonyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride The product of Example 12 (0.386 g, 0.475 mmol) was dissolved in a mixture of ethyl acetate (2.4 mL) and 4 N HCl in dioxane (2.4 mL) and stirred at room temperature for one hour. The mixture was then evaporated under reduced pressure to provide the title compound (0.338 mg, 100% yield).

Example 13b

A mixture of the product of Example 13a (30 mg, 0.040 mmol), 5-methylisoxazole-3-carboxylic acid (5.1 mg, 0.040 mmol), N-ethyl-N-isopropylpropan-2-amine (15.6 mg, 0.12 mmol), and HATU (18.3 mg, 0.048 mmol) in dichloromethane (0.5 mL) was stirred at room temperature for one hour and then evaporated. Purification of the crude material via reverse phase chromatography eluting with acetonitrile/water/TFA provided the title compound (14 mg, 42% yield). MS (ESI): m/z=822.0[M+H].

Example 14

(2R,6S,13aS,14aR,16aS,Z)-2-(3-(benzofuran-2-yl)quinoxalin-2-yloxy)-N-(cyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 14 was prepared according to the procedure utilized for the preparation of Example 13, replacing 5-methylisoxazole-3-carboxylic acid with 5-methylpyrazine-2-carboxylic acid. Purification of the crude material via reverse phase chromatography eluting with acetonitrile/water/TFA provided the title compound.
MS (ESI): m/z=833.0 [M+H].

Example 15

(2R,6S,13aR,14aR,16aS,Z)-2-(3-(benzofuran-2-yl)quinoxalin-2-yloxy)-N-(cyclopropylsulfonyl)-6-(1-methyl-1H-pyrazole-3-carboxamido)-5,16-dioxo-1,2,3,5,6,7,8,9,10,11,13a,14,14a,15,16,16a-hexadecahydrocyclopropalelpyrrolo[1,2-a][1,4]diazacyclopentadecine-14a-carboxamide Example 15 was prepared according to the procedure utilized for the preparation of Example 13, replacing 5-methylisoxazole-3-carboxylic acid with 1-methyl-1H-pyrazole-3-carboxylic acid. Purification of the crude material via reverse phase chromatography eluting with acetonitrile/water/TFA provided the title compound.
MS (ESI): m/z=821.1 [M+H].

Example 16

(2R,6S,13aS,14aR,16aS,Z)-2-(3-(benzofuran-2-yl)quinoxalin-2-yloxy)-N-(cyclopropylsulfonyl)-6-(1,5-dimethyl-1H-pyrazole-3-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 16 was prepared according to the procedure utilized for the preparation of Example 13, replacing 5-methylisoxazole-3-carboxylic acid with 1,5-dimethyl-1H-pyrazole-3-carboxylic acid. Purification of the crude material via reverse phase chromatography eluting with acetonitrile/water/TFA provided the title compound.
MS (ESI): m/z=835.0 [M+H].

Example 17

(2R,6S,13aS,14aR,16aS,Z)-2-(3-(benzofuran-2-yl)quinoxalin-2-yloxy)-N-(cyclopropylsulfonyl)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 17 was prepared according to the procedure utilized for the preparation of Example 13, replacing 5-methylisoxazole-3-carboxylic acid with pyrimidine-4-carboxylic acid. Purification of the crude material via reverse phase chromatography eluting with acetonitrile/water/TFA provided the title compound.
MS (ESI): m/z=818.9 [M+H].

Example 18 tert-butyl (2R,6S,13aS,14aR,16aS,Z)-2-(3-(benzo[b]thiophen-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Example 18 was prepared according to the procedure utilized for the preparation of Example 12, replacing benzofuran-2-yltributylstannane with benzo[b]thiophen-2-yltributylstannane. Purification of the crude material via silica gel chromatography eluting with hexane/ethyl acetate (1:2) provided the title compound.
MS (ESI): m/z=829.1 [M+H].

Example 19

N-((2R,6S,13aS,14aR,16aS,Z)-2-(3-(benzo[b]
thiophen-2-yl)quinoxalin-2-yloxy)-14a-(cyclopropylsulfonylcarbamoyl)-5,16-dioxo-1,2,3,5,6,7,8,9,
10,11,13a,14,14a,15,16,16a-
hexadecahydrocyclopropa[e]pyrrolo[1,2-a][1,4]
diazacyclopentadecin-6-yl)-5-methylisoxazole-3-
carboxamide

Example 19a (2R,6S,13aS,14aR,16aS,Z)-6-amino-2-(3-(benzo[b]
thiophen-2-yl)quinoxalin-2-yloxy)-N-(cyclopropylsulfonyl)-5,16-dioxo-1,2,3,5,6,7,8,9,10,11,13a,14,
14a,15,16,16a-hexadecahydrocyclopropa[e]pyrrolo
[1,2-a][1,4]diazacyclopentadecine-14a-carboxamide
hydrochloride The product of Example 18 (0.296 g, 0.357 mmol) was dissolved in a mixture of ethyl acetate (1.7 mL) and 4 N HCl in dioxane (1.7 mL) and stirred at room temperature for one hour. The mixture was then evaporated under reduced pressure to provide the title compound (0.262 mg, 96% yield).

Example 19b

A mixture of the product of Example 19a (30 mg, 0.039 mmol), 5-methylisoxazole-3-carboxylic acid (5.0 mg, 0.039 mmol), N-ethyl-N-isopropylpropan-2-amine (15.2 mg, 0.118 mmol), and HATU (17.9 mg, 0.047 mmol) in dichloromethane (0.5 mL) was stirred at room temperature for one hour and then evaporated. Purification of the crude material via reverse phase chromatography eluting with acetonitrile/water/TFA provided the title compound (18 mg, 53% yield).
MS (ESI): m/z=837.9[M+H].

Example 20

(2R,6S,13aS,14aR,16aS,Z)-2-(3-(benzo[b]thiophen-
2-yl)quinoxalin-2-yloxy)-N-(cyclopropylsulfonyl)-6-
(5-methylpyrazine-2-carboxamido)-5,16-dioxo-1,2,
3,5,6,7,8,9,10,11,13a,14,14a,15,16,16a-
hexadecahydrocyclopropa[e]pyrrolo[1,2-a][1,4]
diazacyclopentadecine-14a-carboxamide Example 20 was prepared according to the procedure utilized for the preparation of Example 19, replacing 5-methylisoxazole-3-carboxylic acid with 5-methylpyrazine-2-carboxylic acid. Purification of the crude material via reverse phase chromatography eluting with acetonitrile/water/TFA provided the title compound.
MS (ESI): m/z=848.7 [M+H].

Example 21

(2R,6S,13aS,14aR,16aS,Z)-2-(3-(benzo[b]thiophen-
2-yl)quinoxalin-2-yloxy)-N-(cyclopropylsulfonyl)-6-
(1-methyl-1H-pyrazole-3-carboxamido)-5,16-dioxo-
1,2,3,5,6,7,8,9,10,11,13a,14,14a,15,16,16a-
hexadecahydrocyclopropa[e]pyrrolo[1,2-a][1,4]
diazacyclopentadecine-14a-carboxamide Example 21 was prepared according to the procedure utilized for the preparation of Example 19, replacing 5-methylisoxazole-3-carboxylic acid with 1-methyl-1H-pyrazole-3-carboxylic acid. Purification of the crude material via reverse phase chromatography eluting with acetonitrile/water/TFA provided the title compound.
MS (ESI): m/z=836.9 [M+H].

Example 22

(2R,6S,13aS,14aR,16aS,Z)-2-(3-(benzo[b]thiophen-
2-yl)quinoxalin-2-yloxy)-N-(cyclopropylsulfonyl)-6-
(1,5-dimethyl-1H-pyrazole-3-carboxamido)-5,16-
dioxo-1,2,3,5,6,7,8,9,10,11,13a,14,14a,15,16,16a-
hexadecahydrocyclopropa[e]pyrrolo[1,2-a][1,4]
diazacyclopentadecine-14a-carboxamide Example 22 was prepared according to the procedure utilized for the preparation of Example 19, replacing 5-methylisoxazole-3-carboxylic acid with 1,5-dimethyl-1H-pyrazole-3-carboxylic acid. Purification of the crude material via reverse phase chromatography eluting with acetonitrile/water/TFA provided the title compound.
MS (ESI): m/z=851.0 [M+H].

Example 23

(2R,6S,13aS,14aR,16aS,Z)-2-(3-(benzo[b]thiophen-
2-yl)quinoxalin-2-yloxy)-N-(cyclopropylsulfonyl)-5,
16-dioxo-6-(pyrimidine-4-carboxamido)-1,2,3,5,6,7,
8,9,10,11,13a,14,14a,15,16,16a-
hexadecahydrocyclopropa[e]pyrrolo[1,2-a][1,4]
diazacyclopentadecine-14a-carboxamide Example 23 was prepared according to the procedure utilized for the preparation of Example 19, replacing 5-methylisoxazole-3-carboxylic acid with pyrimidine-4-carboxylic acid. Purification of the crude material via reverse phase chromatography eluting with acetonitrile/water/TFA provided the title compound.
MS (ESI): m/z=835.1 [M+H].

Example 24 tert-butyl (2R,6S,13aS,14aR,16aS,Z)-14a-(cyclopropylsulfonylcarbamoyl)-5,16-dioxo-2-(phenanthridin-
6-yloxy)-1,2,3,5,6,7,8,9,10,11,13a,14,14a,15,16,16a-
hexadecahydrocyclopropa[e]pyrrolo[1,2-a][1,4]
diazacyclopentadecin-6-ylcarbamate

Example 24a (2S,6S,13aS,14aR,16aS,Z)-ethyl 2-(4-bromophenylsulfonyloxy)-6-(tert-butoxycarbonylamino)-5,16-
dioxo-1,2,3,5,6,7,8,9,10,11,13a,14,14a,15,16,16a-
hexadecahydrocyclopropa[e]pyrrolo[1,2-a][1,4]
diazacyclopentadecine-14a-carboxylate A solution of (2S,6S,13aS,14aR,16aS,Z)-ethyl 6-(tert-butoxycarbonylamino)-2-hydroxy-5,16-dioxo-1,2,3,5,6,7,8,9,
10,11,13a,14,14a,15,16,16a-hexadecahydrocyclopropa[e]
pyrrolo[1,2-a][1,4]diazacyclopentadecine-14a-carboxylate
(22.1 g, 44.8 mmol) and DABCO (8.5 g, 76.7 mmol) in toluene (88 mL) was stirred at room temperature. To this solution was added a solution of 4-bromobenzene-1-sulfonyl chloride 17.2 g, 67.2 mmol) in toluene (44 mL). After the addition was complete the reaction mixture was quenched with 10% aqueous sodium carbonate (110 mL) and the mixture stirred for 15 min. Tetrahydrofuran (44 mL) was added and the mixture was washed with 0.5 M HCl, water, and then saturated aqueous sodium chloride. The organic layer was dried over anhydrous magnesium sulfate, filtered, and evaporated under reduced pressure and dried to provide the title compound (27.7 g, 87% yield), which was used without further purification.

Example 24b (2R,6S,13aS,14aR,16aS,Z)-ethyl 6-(tert-butoxycarbonylamino)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylate To a solution of the compound of Example 24a (11.0 g, 15.4 mmol) in NMP (100 ml) was added phenanthridine-6 (5H)-one (3.15 g, 16.2 mmol) followed by $Cs_2CO_3$ (7.53 g, 23.1 mmol). The resulting mixture was heated to 55° C. for four hours. The reaction mixture was cooled to room temperature, and then partitioned between ethyl acetate (250 ml) and 5% aqueous sodium bicarbonate solution (200 ml). The organic layer was separated, washed with 5% aqueous sodium bicarbonate solution (200 ml) followed by brine (150 ml), dried over anhydrous sodium sulfate, and concentrated under reduced pressure to obtain the crude product as a solid. The solid was then dissolved in methyl t-butyl ether (200 ml), the resulting suspension was stirred at room temperature for 1 hour and filtered. The filtrate contained the desired product was concentrated under reduced pressure to obtain 7.95 g of product 24b as a solid; MS-DCI/$NH_3$: 671 $(M+H)^+$.

Example 24c (2R,6S,13aS,14aR,16aS,Z)-6-(tert-butoxycarbonylamino)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid (24c)

To a solution of the product of Example 24b (7.8 g, 11.6 mmol) in tetrahydrofuran (40 ml)/ethanol (40 ml) was added an aqueous lithium hydroxide solution (0.84 g of lithium hydroxide in 40 ml of $H_2O$). The resulting mixture was heated to 50° C. for two hours and cooled to room temperature. The organic solvents were mostly removed under reduced pressure, and the resulting residue was acidified with 10% citric acid aqueous solution and extracted with ethyl acetate (200 ml). The organic layer was separated, washed with brine (200 ml), dried over anhydrous $Na_2SO_4$, filtered and concentrated under reduced pressure to give a light yellow solid, which was further dried in a vacuum oven at 45° C. for 18 h to afford 7.5 g of product 24c as a light yellow solid; MS-DCI/$NH_3$: 643 $(M+H)^+$.

Example 24d tert-butyl (2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate To a solution of product of Example 24c (7.46 g, 11.6 mmol) in DMF (80 ml) was added 1,1'-carbomyldiimidazole (5.64 g, 34.8 mmol). The reaction mixture was stirred at room temperature for 6 hours. To the above solution was then added cyclopropanesulfonamide (4.21 g, 34.8 mmol) followed by DBU (5.73 ml, 36.0 mmol). The resulting mixture was stirred at room temperature for 14 hours. To the reaction mixture was added EtOAc (200 ml), 10% aqueous citric acid solution (200 ml) and saturated aqueous sodium chloride (50 ml). The organic layer was separated, washed with saturated aqueous sodium chloride (100 ml), dried over anhydrous $Na_2SO_4$, filtered, and concentrated under reduced pressure. The residue was purified by column chromatography on silica gel (ethyl acetate/heptane gradient) to obtain the title compound as a white solid (6.40 g, 74% yield). MS (ESI): m/z=746.1 [M+H].

Example 25

(2R,6S,13aS,14aR,16aS,Z)-N-(cyclopropylsulfonyl)-5,16-dioxo-2-(phenanthridin-6-yloxy)-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

Example 25a (2R,6S,13aS,14aR,16aS,Z)-6-amino-N-(cyclopropylsulfonyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide hydrochloride To a suspension of the product of Example 24 (0.35 g, 0.47 mmol) in acetonitrile (5 mL) was added a 4 M solution of HCl in dioxane (0.6 mL, 2.4 mmol). The reaction mixture was stirred at room temperature for 4 h. The solvent was evaporated under reduced pressure and the resulting solid dried under vacuum to provide the title compound (0.32 g, quant. yield).

Example 25b (2R,6S,13aS,14aR,16aS,Z)-N-(cyclopropylsulfonyl)-5,16-dioxo-2-(phenanthridin-6-yloxy)-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide To a solution of Example 25a (320 mg, 0.47 mmol) in dimethylformamide (5 mL) was added pyrazinecarboxylic acid (0.065 g, 0.52 mmol), HATU (214 mg, 0.56 mmol) and diisopropylethylamine (0.2 mL, 1.18 mmol). The reaction mixture was stirred at 25° C. for 2 h and then partitioned between 5% aqueous sodium bicarbonate and ethyl acetate. The organic layer was dried over anhydrous magnesium sulfate, filtered, and evaporated. The residue was purified by crystallization from ethyl acetate/hexane to give the desired product (155 mg, 44% yield) as an off-white solid.

MS (ESI): m/z=752.0 [M+H].

Example 26

Cyclopentyl (2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate

Example 26a (2R,6S,13aS,14aR,16aS,Z)-ethyl 6-(cyclopentyloxycarbonylamino)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylate Example 26a was prepared according to the procedure utilized for the preparation of Example 24b, replacing the compound of Example 24a with compound (2S,6S,13aS,14aR,16aS,Z)-ethyl 2-(4-bromophenylsulfonyloxy)-6-(cyclopentyloxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate, to provide the title compound.
MS (DCUNH$_3$): m/z=683.0 [M+H]

Example 26b (2R,6S,13aS,14aR,16aS,Z)-6-(cyclopentyloxycarbonylamino)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid Example 26b was prepared according to the procedure utilized for the preparation of Example 24c, replacing compound 24b with compound 26a, to provide the title compound.
MS (DCUNH$_3$): m/z=655.0 [M+H].

Example 26c

Cyclopentyl (2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate
The title compound of Example 26 was prepared according to the procedure utilized for the preparation of Example 24, replacing compound 24c with compound 26b, to provide the title compound.
MS (DCl/NH$_3$): m/z=758.0 [M+H].

Example 27

(2R,6S,13aR,14aR,16aS,Z)-N-(cyclopropylsulfonyl)-6-(5-methyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 27 was prepared according to the procedure utilized for the preparation of Example 25, replacing 2-pyrazinecarboxylic acid with 5-methyl-1H-pyrazole-3-carboxylic acid. Purification of the crude material via reverse phase chromatrography eluting with acetonitrile/water/TFA provided the title compound.
MS (ESI): m/z=754.2 [M+H].

Example 28

N-((2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide Example 28 was prepared according to the procedure utilized for the preparation of Example 25, replacing 2-pyrazinecarboxylic acid with 5-methylisoxazole-3-carboxylic acid. Purification of the crude material via reverse phase chromatography eluting with acetonitrile/water/TFA provided the title compound.
MS (ESI): m/z=755.1 [M+H].

Example 29

(2R,6S,13aS,14aR,16aS,Z)-N-(cyclopropylsulfonyl)-6-(5-methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 29 was prepared according to the procedure utilized for the preparation of Example 25, replacing 2-pyrazinecarboxylic acid with 5-methylpyrazine-2-carboxylic acid. Purification of the crude material via reverse phase chromatography eluting with acetonitrile/water/TFA provided the title compound.
MS (ESI): m/z=766.1 [M+H].

Example 30

N-((2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-5-carboxamide Example 30 was prepared according to the procedure utilized for the preparation of Example 25, replacing 2-pyrazinecarboxylic acid with thiazole-5-carboxylic acid. Purification of the crude material via reverse phase chromatography eluting with acetonitrile/water/TFA provided the title compound.
MS (ESI): m/z=757.1 [M+H].

Example 31

(2R,6S,13aS,14aR,16aS,Z)-N-(cyclopropylsulfonyl)-6-(2-fluorobenzamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 31 was prepared according to the procedure utilized for the preparation of Example 25, replacing 2-pyrazinecarboxylic acid with 2-fluorobenzoic acid. Purification of the crude material via reverse phase chromatography eluting with acetonitrile/water/TFA provided the title compound.
MS (ESI): m/z=768.1 [M+H].

Example 32

(2R,6S,13aS,14aR,16aS,Z)-N-(cyclopropylsulfonyl)-5,16-dioxo-2-(phenanthridin-6-yloxy)-6-(pyridazine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 32 was prepared according to the procedure utilized for the preparation of Example 25, replacing 2-pyrazinecarboxylic acid with pyridazine-4-carboxylic acid. Purification of the crude material via reverse phase chromatography eluting with acetonitrile/water/TFA provided the title compound.
MS (ESI): m/z=752.1 [M+H].

Example 33

(2R,6S,13aS,14aR,16aS,Z)-N-(cyclopropylsulfonyl)-5,16-dioxo-2-(phenanthridin-6-yloxy)-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 33 was prepared according to the procedure utilized for the preparation of Example 25, replacing 2-pyrazinecarboxylic acid with pyrimidine-4-carboxylic acid. Purification of the crude material via reverse phase chromatography eluting with acetonitrile/water/TFA provided the title compound.
MS (ESI): m/z=752.1 [M+H].

Example 34

(2R,6S,13aS,14aR,16aS,Z)-N-(cyclopropylsulfonyl)-6-(1-methyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 34 was prepared according to the procedure utilized for the preparation of Example 25, replacing 2-pyrazinecarboxylic acid with 1-methyl-1H-pyrazole-3-carboxylic acid. Purification of the crude material via reverse phase chromatography eluting with acetonitrile/water/TFA provided the title compound.
MS (ESI): m/z=754.2 [M+H].

Example 35

(2R,6S,13aS,14aR,16aS,Z)-N-(cyclopropylsulfonyl)-6-(2-hydroxy-2-methylpropanamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 35 was prepared according to the procedure utilized for the preparation of Example 25, replacing 2-pyrazinecarboxylic acid with 2-hydroxy-2-methylpropanoic acid. Purification of the crude material via reverse phase chromatography eluting with acetonitrile/water/TFA provided the title compound.
MS (ESI): m/z=732.2 [M+H].

Example 36

(2R,6S,13aS,14aR,16aS,Z)-N-(cyclopropylsulfonyl)-6-(1,5-dimethyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 36 was prepared according to the procedure utilized for the preparation of Example 25, replacing 2-pyrazinecarboxylic acid with 1,5-dimethyl-1H-pyrazole-3-carboxylic acid. Purification of the crude material via reverse phase chromatography eluting with acetonitrile/water/TFA provided the title compound.
MS (ESI): m/z=768.1 [M+H].

Example 37

Cyclopentyl (2R,6S,13aS,14aR,16aS,Z)-14a-(cyclopropylsulfonylcarbamoyl)-2-(2-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Example 37a 5'-Fluoro-2'-nitrobiphenyl-2-carboxylate To a microwave vessel was added 2-(methoxycarbonyl)phenylboronic acid (63.4 mg, 0.352 mmol), 2-bromo-4-fluoro-1-nitrobenzene (77 mg, 0.35 mmol), diacetoxypalladium (0.93 mg, 4.1 mmol) and dicyclohexyl(2',6'-dimethoxybiphenyl-2-yl)phosphine (3.47 mg, 8.45 µmol). Ethanol (1760 µl) and sodium carbonate (176 µl, 0.352 mmol) were added and the mixture was reacted in a microwave reactor at 100° C. for 30 min. The reaction mixture was diluted with dichloromethane, dried over anhydrous sodium sulfate, filtered, and concentrated under reduced pressure. The residue was purified by preparative thin layer chromatography (eluant: 9:1 hexane/ethyl acetate) to provide methyl 5'-fluoro-2'-nitrobiphenyl-2-carboxylate (37a, 54.8 mg, 0.199 mmol, 56.6% yield).

Example 37b 2-fluoro-5-hydroxyphenanthridin-6(5H)-one

To a solution of the product of Example 37a (methyl 5'-fluoro-2'-nitrobiphenyl-2-carboxylate, 56.79 mg, 0.206 mmol) in methanol (9 mL) was added 10% palladium on carbon (15.6 mg, 0.015 mmol). The flask was fitted with a hydrogen balloon and de-gassed three times with hydrogen. The reaction mixture was stirred, diluted with dimethylformamide, and filtered. The filtrate was concentrated to provide 2-fluoro-5-hydroxyphenanthridin-6(5H)-one (37b, 46.36 mg, 0.202 mmol, 98% yield).

Example 37c

2-Fluorophenanthridin-6(5H)-one

A mixture of the product of Example 37b (2-fluoro-5-hydroxyphenanthridin-6(5H)-one, 46.4 mg, 0.202 mmol), acetic acid (3 mL), and zinc (99 mg, 1.517 mmol) was heated under reflux at 130° C. for 1 h. The mixture was diluted with dimethylformamide and filtered and the filtrate was concentrated to give a tan solid (100 mg). The solid was partitioned between dichloromethane/dimethylformamide (2/1, 50 mL) and sodium carbonate (10 ml). The organic layer was washed with water (2×10 ml) and concentrated to provide 2-fluorophenanthridin-6(5H)-one (37c, 38.2 mg, 88% yield).

Example 37d (2R,6S,13aS,14aR,16aS,Z)-ethyl 6-(cyclopentyloxycarbonylamino)-2-(2-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate Example 37d was prepared according to the procedure used for the preparation of Example 37b, substituting (2S,6S,13aS,14aR,16aS,Z)-ethyl 2-(4-bromophenylsulfonyloxy)-6-(cyclopentyloxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate for 1a, and substituting 2-fluorophenanthridin-6(5H)-one (80c) for phenanthridin-6(5H)-one, to provide the title compound in 48% yield.

Example 37e (2R,6S,13aS,14aR,16aS,Z)-6-(cyclopentyloxycarbonylamino)-2-(2-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid Example 37e was prepared according to the procedure used for the preparation of Example 67c, substituting the product of Example 37d for the product of Example 24b.

Example 37f

Cyclopentyl (2R,6S,13aS,14aR,16aS,Z)-14a-(cyclopropylsulfonylcarbamoyl)-2-(2-fluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbama The compound of Example 37 was prepared according to the procedure used for the preparation of Example 24, substituting the product of Example 37e for the product of Example 24c (14.6 mg, 78% yield).
MS (ESI): m/z=776.1 [M+H].

Example 38 tert-Butyl (2R,6S,13aR,14aR,16aS,Z)-14a-(cyclopropylsulfonylcarbamoyl)-2-(2,9-difluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Example 38a Methyl 5,5'-difluoro-2'-nitrobiphenyl-2-carboxylate To 2-bromo-4-fluoro-1-nitrobenzene (185.16 mg, 0.842 mmol) was added Pd$_2$dba$_3$ (23.12 mg, 0.025 mmol) and copper powder (271 mg, 4.26 mmol). Dimethylsulfoxide (2.3 ml) and methyl 2-bromo-4-fluorobenzoate (0.122 ml, 0.842 mmol) were added and the mixture was stirred vigorously at 100° C. for 2 h. The mixture was cooled to room temperature, diluted with ethyl acetate (20 ml), and filtered. The filtrate was washed with water and dried (anhydrous Na$_2$SO$_4$) and concentrated to give a yellow oil (279.8 mg). This oil was utilized without purification for the preparation of Example 38b.

Example 38b 2,9-Difluoro-5-hydroxyphenanthridin-6(5H)-one

To the product of Example 38a (279.8 mg) was added methanol (7.5 mL) and 10% palladium on carbon (76 mg, 0.071 mmol). The flask was fitted with a hydrogen balloon and the mixture was de-gased and back-filled with hydrogen three times. The mixture was stirred under hydrogen for 16 h, diluted with dimethylformamide and filtered. The filtrate was concentrated to give a red solid. This material was triturated with dichloromethane/hexane (9/1) and filtered to provide the title compound (Example 38b, 43.15 mg, 0.175 mmol, quantitative yield).

Example 38c 2,9-Difluorophenanthridin-6(5H)-one

Example 38c was prepared according to the procedure used for the preparation of Example 37c, substituting the product of Example 38b for the product of Example 80b.

Example 38d (2R,6S,13aS,14aR,16aS,Z)-ethyl 6-(tert-butoxycarbonylamino)-2-(2,9-difluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate Example 38d was prepared according to the procedure used for the preparation of Example 24c, substituting the product of Example 38c for phenanthridine-6(5H)-one.

Example 38e (2R,6S,13aS,14aR,16aS,Z)-6-(tert-butoxycarbonylamino)-2-(2,9-difluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylic acid Example 38e was prepared according to the procedure used for the preparation of Example 24c, substituting the product of Example 38d for the product of Example 24b.

Example 38f tert-Butyl (2R,6S,13aS,14aR,16aS,Z)-14a-(cyclopropylsulfonylcarbamoyl)-2-(2,9-difluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate Example 38 was prepared according to the procedure used for the preparation of Example 24, substituting the product of Example 38e for the product of Example 24c.
MS (ESI): m/z=782.1 [M+H].

Example 39 tert-butyl (2R,6S,13aR,14aR,16aS)-14a-(cyclopropylsulfonylcarbamoyl)-5,16-dioxo-2-(phenanthridin-6-yloxy)octadecahydrocyclopropa[e]pyrrolo[1,2-a][1,4]diazacyclopentadecin-6-ylcarbamate Argon degassed ethanol (0.8 ml) was added to the product of Example 24 (79.1 mg, 0.106 mmol) and Crabtree's Catalyst (3.45 mg, 4.24 μmol) (4 mole %) in a 4 mL pressure bottle. The vessel was sparged three times with argon and then pressurized with hydrogen (50 psi). The mixture was heated to 50° C. under hydrogen and stirred for 4.5 hr at 50° C.

The reaction mixture was concentrated and purified by reverse phase chromatography, eluting with an acetonitrile (1% TFA)/water gradient to provide the title compound as a white solid (70.41 mg, 0.094 mmol, 89% yield).

MS (ESI): m/z=748.2 [M+H].

Example 40

Cyclopentyl (2R,6S,13aR,14aR,16aS)-14a-(cyclopropylsulfonylcarbamoyl)-5,16-dioxo-2-(phenanthridin-6-yloxy)octadecahydrocyclopropa[e]pyrrolo[1,2-a][1,4]diazacyclopentadecin-6-ylcarbamate Example 40 was prepared according to the procedure utilized for the preparation of Example 39, replacing the product of Example 24 with the product of Example 26.

MS (ESI): m/z=760.2 [M+H].

Example 41 tert-Butyl (2R,6S,13aR,14aR,16aS)-5,16-dioxo-2-(phenanthridin-6-yloxy)-14a-(thiophen-2-ylsulfonylcarbamoyl)octadecahydrocyclopropa[e]pyrrolo[1,2-a][1,4]diazacyclopentadecin-6-ylcarbamate Example 41 was prepared according to the procedure utilized for the preparation of Example 24, replacing cyclopropanesulfonamide with thiophene-2-sulfonamide.

MS (ESI): m/z=788.0 [M+H].

Example 42

(2R,6S,13aS,14aR,16aS,Z)-N-(cyclopropylsulfonyl)-6-(2-methylpyrimidine-5-carboxamido)-5,16-dioxo-2-(3-(benzo[d]thiazol-2-yl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

Example 42a (S)-2-(2-methylpyrimidine-5-carboxamido)non-8-enoic acid

Boc-2(S)-amino-non-8-eoic acid dicyclohexylamine salt can be suspended in isopropyl acetate, washed several times with an aqueous citric acid solution and then once with water. The washed product, concentrated and then re-diluted in isopropyl acetate, can be reacted with HCl to produce 2(S)-amino-non-8-eoic acid HCl salt. 2-Methylpyrimidine-5-carboxylic acid, N,N'-disuccinimidyl carbonate, and N,N-dimethylaminopyridine can be dissolved in N-methyl-2-pyrrolidone (NMP) and stirred. 2(S)-Amino-non-8-eoic acid HCl salt is subsequently added, followed by triethylamine, and stirred to produce the title compound of Example 42a, which can be crystallized out by adding HCl followed by water.

Example 42b (1R,2S)-ethyl-1-((2S,4R)-N-(tert-butoxycarbonyl)-1-((S)-2-(2-methylpyrimidine-5-carboxamido)non-8-enoyl)-4-(3-(benzo[d]thiazol-2-yl)quinoxalin-2-yloxy)pyrrolidine-2-carboxamido)-2-vinylcyclopropanecarboxylate (2S,4R)-N-Boc-4-hydroxyproline can be reacted with 2-chloro-3-(thiophen-2-yl)quinoxaline in NMP, in the presence of sodium t-butoxide, to produce (2S,4R)-1-(tert-butoxycarbonyl)-4-(3-(benzo[d]thiazol-2-yl)quinoxalin-2-yloxy)pyrrolidine-2-carboxylic acid. Methyl tertiary butyl ether (MTBE) and water can then be added. The aqueous layer is separated, washed, and then HCl is added, followed by extraction with MTBE. The extracted product can be mixed with diisopropylethylamine (DIPEA) and HATU (CAS #148893-10-1), and then reacted with (1R,2S)-ethyl-1-amino-2-vinylcyclopropanecarboxylate tosylate salt in dimethylformide (DMF) and toluene. The reaction produces (2S,4R)-tert-butyl 2-((1R,2S)-1-(ethoxycarbonyl)-2-vinylcyclopropylcarbamoyl)-4-(3-(benzo[d]thiazol-2-yl)quinoxalin-2-yloxy)pyrrolidine-1-carboxylate, which can be extracted with MTBE and washed with HCl, further extracted, washed, dried, and dissolved in 2-propanol.

HCl can be added to the 2-propanol solution to produce (1R,2S)-ethyl 1-((2S,4R)-4-(3-(benzo[d]thiazol-2-yl)quinoxalin-2-yloxy)pyrrolidine-2-carboxamido)-2-vinylcyclopropanecarboxylate, which can be crystallized out by neutralizing with NaOH.

(1R,2S)-ethyl 1-((2S,4R)-4-(3-(benzo[d]thiazol-2-yl)quinoxalin-2-yloxy)pyrrolidine-2-carboxamido)-2-vinylcyclopropanecarboxylate, the title compound of Example 42a, N-hydroxy-5-norbornene-2,3-dicarboximide, and N-(3-dimethylaminopropyl)-N'-ethylcarbodiimide hydrochloride can be mixed and stirred in DMF for hours, followed by addition of N,N-dimethylethylene diamine. The reaction produces (1R,2S)-ethyl 1-((2S,4R)-1-((S)-2-(2-methylpyrimidine-5-carboxamido)non-8-enoyl)-4-(3-(benzo[d]thiazol-2-yl)quinoxalin-2-yloxy)pyrrolidine-2-carboxamido)-2-vinylcyclopropanecarboxylate, which can be dissolved in isopropyl acetate and extracted with aqueous $H_3PO_4$, and then extracted with aqueous $K_2HPO_4$. The product can be reacted with di-tert-butyldicarbonate in the presence of dimethylaminopyridine, followed by extraction with a mixture of a citric acid solution and a sodium chloride solution, to produce the title compound of Example 42b.

Example 42c (2R,6S,13aS,14aR,16aS,Z)-ethyl-6-(2-methylpyrimidine-5-carboxamido)-5,16-dioxo-2-(3-(benzo[d]thiazol-2-yl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylate hydrochloride The product of Example 42b can be subject to ring-closing metathesis in the presence of Zhan-B catalyst in toluene to produce (2R,6S,13aS,14aR,16aS,Z)-15-tert-butyl 14a-ethyl 6-(2-methylpyrimidine-5-carboxamido)-5,16-dioxo-2-(3-(benzo[d]thiazol-2-yl)quinoxalin-2-yloxy)-2,3,5,6,7,8,9,10,11,13a,14,14a,16,16a-tetradecahydrocyclopropa[e]pyrrolo[1,2-a][1,4]diazacyclopentadecine-14a,15(1H)-dicarboxylate. The catalyst can be quenched with imidazole after the reaction.

The ring-closed product in toluene can be solvent switched to acetonitrile, followed by addition of hydrogen chloride in dioxane and heated to produce the title compound of Example 42c.

Example 42d (2R,6S,13aS,14aR,16aS,Z)-N-(cyclopropylsulfonyl)-6-(2-methylpyrimidine-5-carboxamido)-5,16-dioxo-2-(3-(benzo[d]thiazol-2-yl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide The isolated product of Example 42c can be mixed with tetrahydrofuran, water and LiOH.H$_2$O, and then heated and stirred. The reaction mixture can be later cooled, added with aqueous H$_3$PO$_4$, aqueous NaCl and 2-methyl tetrahydrofuran, and the organic layer is separated, washed and filtered. MeCN is added to the concentrated organic layer, heated and cooled, and then diethylamine is added. The slurry is heated and cooled to form (2R,6S,13aS,14aR,16aS,Z)-6-(2-methylpyrimidine-5-carboxamido)-5,16-dioxo-2-(3-(benzo[d]thiazol-2-yl)quinoxalin-2-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylate diethylamine salt, which can be further washed and dried.

The diethylamine salt can be mixed with tetrahydrofuran, 2-methyl tetrahydrofuran and aqueous H3PO4. The organic layer is separated, washed with aqueous NaCl, and then concentrated and/or purified. The product can be subsequently mixed with NMP, followed by addition of carbonyldiimidazole (CDI) and then 1,8-diazabicyclo[5.4.0]undec-7-ene (DBU). Cyclopropylsulfonamide can be subsequently added. The reaction mixture is stirred for hours.

Isopropyl acetate can then be added, followed by aqueous KH$_2$PO$_4$ and then aqueous H$_3$PO$_4$. The organic layer can be isolated, washed, and purified to produce the title compound of Example 42d.

Example 43

N-((2R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-3-methylisoxazole-5-carboxamide Example 43 can be prepared according to the procedure described for the preparation of Example 42, replacing 2-methylpyrimidine-5-carboxylic acid from Example 42a with 3-methylisoxazole-5-carboxylic acid in Example 43a to produce (S)-2-(3-methylisoxazole-5-carboxamido)non-8-enoic acid. All subsequent steps should proceed in a similar fashion to Example 42 to produce Example 43.

Example 44

N-42R,6S,13aS,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide Example 44 can be prepared according to the procedure described for the preparation of Example 42, replacing 2-methylpyrimidine-5-carboxylic acid from Example 42a with 5-methylisoxazole-3-carboxylic acid in Example 44a to produce (S)-2-(5-methylisoxazole-3-carboxamido)non-8-enoic acid. All subsequent steps should proceed in a similar fashion to Example 42 to produce Example 44.

Example 45

(2R,6S,13aS,14aR,16aS,Z)-2-(3-(benzo[d]thiazol-2-yl)quinoxalin-2-yloxy)-N-(cyclopropylsulfonyl)-6-(3-fluorobenzamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 45 can be prepared according to the procedure described for the preparation of Example 42, replacing 2-methylpyrimidine-5-carboxylic acid from Example 42a with 3-fluorobenzoic acid in Example 45a to produce (S)-2-(3-fluorobenzamido)non-8-enoic acid. All subsequent steps should proceed in a similar fashion to Example 42 to produce Example 45.

Example 46

(2R,6S,13aS,14aR,16aS,Z)-2-(3-(benzo[d]thiazol-2-yl)quinoxalin-2-yloxy)-N-(cyclopropylsulfonyl)-5,16-dioxo-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 46 can be prepared according to the procedure described for the preparation of Example 42, replacing 2-methylpyrimidine-5-carboxylic acid from Example 42a with pyrimidine-4-carboxylic acid in Example 46a to produce (S)-2-(pyrimidine-4-carboxamido)non-8-enoic acid. All subsequent steps should proceed in a similar fashion to Example 42 to produce Example 46.

Example 47

N-((2R,6S,13aR,14aR,16aS,Z)-2-(3-(benzo[d]thiazol-2-yl)quinoxalin-2-yloxy)-14a-(cyclopropylsulfonylcarbamoyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-yl)isoxazole-5-carboxamide Example 47 can be prepared according to the procedure described for the preparation of Example 42, replacing 2-methylpyrimidine-5-carboxylic acid from Example 42a with isoxazole-5-carboxylic acid in Example 47a to produce (S)-2-(isoxazole-5-carboxamido)non-8-enoic acid. All subsequent steps should proceed in a similar fashion to Example 42 to produce Example 47.

Example 48

(2R,6S,13aR,14aR,16aS,Z)-2-(3-(benzo[d]thiazol-2-yl)quinoxalin-2-yloxy)-N-(cyclopropylsulfonyl)-6-(5-methylpyrazine-2-carboxamido)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 48 can be prepared according to the procedure described for the preparation of Example 42, replacing 2-methylpyrimidine-5-carboxylic acid from Example 42a with 5-methylpyrazine-2-carboxylic acid in Example 48a to produce (S)-2-(5-methylpyrazine-2--carboxamido)non-8-enoic acid. All subsequent steps should proceed in a similar fashion to Example 42 to produce Example 48.

Example 49

(2R,6S,13aR,14aR,16aS,Z)-N-(cyclopropylsulfonyl)-6-(5-methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide

Example 49a (S)-2-(5-methylpyrazine-2-carboxamido)non-8-enoic acid

Boc-2(5)-amino-non-8-eoic acid dicyclohexylamine salt can be suspended in isopropyl acetate, washed several times with an aqueous citric acid solution and then once with water. The washed product, concentrated and then re-diluted in isopropyl acetate, can be reacted with HCl to produce 2(S)-amino-non-8-eoic acid HCl salt. 5-Methyl-2-pyrazinecarboxylic acid, N,N'-disuccinimidyl carbonate, and N,N-dimethylaminopyridine can be dissolved in N-methyl-2-pyrrolidone (NMP) and stirred. 2(S)-Amino-non-8-eoic acid HCl salt is subsequently added, followed by triethylamine, and stirred to produce the title compound of Example 49a, which can be crystallized out by adding HCl followed by water.

Example 49b (1R,2S)-ethyl-1-((2S,4R)-N-(tert-butoxycarbonyl)-1-((S)-2-(5-methylpyrazine-2-carboxamido)non-8-enoyl)-4-(phenanthridin-6-yloxy)pyrrolidine-2-carboxamido)-2-vinylcyclopropanecarboxylate (2S,4R)-N-Boc-4-hydroxyproline can be reacted with 6-chlorophenanthridine in NMP, in the presence of sodium t-butoxide, to produce (2S,4R)-1-(tert-butoxycarbonyl)-4-(phenanthridin-6-yloxy)pyrrolidine-2-carboxylic acid. Methyl tertiary butyl ether (MTBE) and water can then be added. The aqueous layer is separated, washed, and then HCl is added, followed by extraction with MTBE. The extracted product can be mixed with diisopropylethylamine (DIPEA) and HATU (CAS #148893-10-1), and then reacted with (1R,2S)-ethyl-1-amino-2-vinylcyclopropanecarboxylate tosylate salt in dimethylformide (DMF) and toluene. The reaction produces (2S,4R)-tert-butyl 2-((1R,2S)-1-(ethoxycarbonyl)-2-vinylcyclopropylcarbamoyl)-4-(phenanthridin-6-yloxy)pyrrolidine-1-carboxylate, which can be extracted with MTBE and washed with HCl, further extracted, washed, dried, and dissolved in 2-propanol.

HCl can be added to the 2-propanol solution to produce (1R,2S)-ethyl 1-((2S,4R)-4-(phenanthridin-6-yloxy)pyrrolidine-2-carboxamido)-2-vinylcyclopropanecarboxylate, which can be crystallized out by neutralizing with NaOH.

(1R,2S)-ethyl 1-((2S,4R)-4-(phenanthridin-6-yloxy)pyrrolidine-2-carboxamido)-2-vinylcyclopropanecarboxylate, the title compound of Example 49a, N-hydroxy-5-norbornene-2,3-dicarboximide, and N-(3-dimethylaminopropyl)-N'-ethylcarbodiimide hydrochloride can be mixed and stirred in DMF, followed by addition of N,N-dimethylethylene diamine. The reaction produces (1R,2S)-ethyl 1-((2S,4R)-1-((S)-2-(5-methylpyrazine-2-carboxamido)non-8-enoyl)-4-(phenanthridin-6-yloxy)pyrrolidine-2-carboxamido)-2-vinylcyclopropanecarboxylate, which can be dissolved in isopropyl acetate and extracted with aqueous $H_3PO_4$, and then extracted with aqueous $K_2HPO_4$. The product can be reacted with di-tert-butyldicarbonate in the presence of dimethylaminopyridine, followed by extraction with a mixture of a citric acid solution and a sodium chloride solution, to produce the title compound of Example 49b.

Example 49c (2R,6S,13aS,14aR,16aS,Z)-ethyl-6-(5-methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylate hydrochloride The product of Example 49b can be subject to ring-closing metathesis in the presence of Zhan-B catalyst in toluene to produce (2R,6S,13aS,14aR,16aS,Z)-15-tert-butyl 14a-ethyl 6-(5-methylpyrazine-2-carboxamido)-5,16-dioxo-2-(phenanthridin-6-yloxy)-2,3,5,6,7,8,9,10,11,13a,14,14a,16,16a-tetradecahydrocyclopropa[e]pyrrolo[1,2-a][1,4]diazacyclopentadecine-14a,15(1H)-dicarboxylate. The catalyst can be quenched with imidazole after the reaction.

The ring-closed product in toluene can be solvent switched to acetonitrile, followed by addition of hydrogen chloride in dioxane and heated to produce the title compound of Example 49c.

Example 49d (2R,6S,13aS,14aR,16aS,Z)-N-(cyclopropylsulfonyl)-6-(5-methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide The isolated product of Example 49c can be mixed with tetrahydrofuran, water and LiOH.H$_2$O, and then heated and stirred. The reaction mixture can be later cooled, added with aqueous H$_3$PO$_4$, aqueous NaCl and 2-methyl tetrahydrofuran, and the organic layer is separated, washed and filtered. MeCN is added to the concentrated organic layer, heated and cooled, and then diethylamine is added. The slurry is heated and cooled to form (2R,6S,13aS,14aR,16aS,Z)-6-(5-Methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxylate diethylamine salt, which can be further washed and dried.

The diethylamine salt can be mixed with tetrahydrofuran, 2-methyl tetrahydrofuran and aqueous H3PO4. The organic layer is separated, washed with aqueous NaCl, and then concentrated and/or purified. The product can be subsequently mixed with NMP, followed by addition of carbonyldiimidazole (CDI) and then 1,8-diazabicyclo[5.4.0]undec-7-ene (DBU). Cyclopropylsulfonamide can be subsequently added. The reaction mixture is stirred for hours. Isopropyl acetate can then be added, followed by aqueous KH$_2$PO$_4$ and then aqueous H$_3$PO$_4$. The organic layer can be isolated, washed, and purified to produce the title compound of Example 49d. The isolated product can be further dissolved in isopropyl acetate and then the solution is diluted with ethanol. Water can be added to the resulting solution in portion-wise manner with adequate hold-times after each addition to ensure de-super-saturation. Water addition is terminated just as the ternary solvent system becomes bi-phasic due to the partial immiscibility of isopropyl acetate, ethanol, water solvent system. The slurry can be stirred for hours and then the solid is isolated via filtration and drying to produce the crystalline hydrate of the title compound.

Example 50

(2R,6S,13aS,14aR,16aS,Z)-N-(cyclopropylsulfonyl)-6-(1,5-dimethyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 50 can be prepared according to the procedure described for the preparation of Example 49, replacing 5-methylpyrazine-2-carboxylic acid from Example 49a with -(1,5-dimethyl-1H-pyrazole-3-carboxylic acid in Example 50a to produce (S)-2-(1,5-dimethyl-1H-pyrazole-3-carboxamido)non-8-enoic acid. All subsequent steps should proceed in a similar fashion to Example 49 to produce Example 50.

Example 51

(2R,6S,13aS,14aR,16aS,Z)-N-(cyclopropylsulfonyl)-6-(5-methyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 51 can be prepared according to the procedure described for the preparation of Example 49, replacing 5-methylpyrazine-2-carboxylic acid from Example 49a with 5-methyl-1H-pyrazole-3-carboxylic acid in Example 51a to produce (S)-2-(5-methyl-1H-pyrazole-3-carboxamido)non-8-enoic acid. All subsequent steps should proceed in a similar fashion to Example 49 to produce Example 51.

Example 52

(2R,6S,13aS,14aR,16aS,Z)-N-(cyclopropylsulfonyl)-6-(2-fluorobenzamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 52 can be prepared according to the procedure described for the preparation of Example 49, replacing 5-methylpyrazine-2-carboxylic acid from Example 49a with 2-fluorobenzoic acid in Example 52a to produce (S)-2-(2-fluorobenzamido)non-8-enoic acid. All subsequent steps should proceed in a similar fashion to Example 49 to produce Example 52.

Example 53

(2R,6S,13aS,14aR,16aS,Z)-N-(cyclopropylsulfonyl)-5,16-dioxo-2-(phenanthridin-6-yloxy)-6-(pyrazine-2-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide Example 53 can be prepared according to the procedure described for the preparation of Example 49, replacing 5-methylpyrazine-2-carboxylic acid from Example 49a with pyrazine carboxylic acid in Example 53a to produce (S)-2-(pyrazine-2-carboxamido)non-8-enoic acid. All subsequent steps should proceed in a similar fashion to Example 49 to produce Example 53.

Example 54 tert-butyl (2R,6S,13aS,14aR,16aS,Z)-14a-(cyclopropylsulfonylcarbamoyl)-5,16-dioxo-2-(thiazolo[4,5-c]quinolin-4-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate A mixture of 5-bromothiazole-4-carboxylic acid methyl ester (0.521 g, 2.35 mmol), 2-(4,4,5,5-tetramethyl-1,3,2-dioxaborolan-2-yl)aniline (0.514 g, 2.35 mmol), 1,1'-bis(di-t-butylphosphino)ferrocene palladium chloride (0.060 g, 0.094 mmol), and sodium carbonate (1.17 mL of 2M aqueous solution) in tetrahydrofuran (12 mL) was stirred under nitrogen at rt for 48 h. The reaction mixture was then heated at 50° C. for an additional 16 h. The reaction mixture was then cooled to rt, diluted with dichoromethane (120 mL) and dimethylformamide (40 mL) and washed with water (20 mL). The resulting solid was isolated by vacuum filtration to provide the title compound (0.251 mg, 53% yield, thiazolo[4,5-c]quinolin-4(5H)-one).

Example 55

Synthesis of the Cyclic Peptide Precursor

The dipeptide 42c (1.91 g) was dissolved in 15 mL of dioxane and 15 mL of 1 N LiOH aqueous solution and the hydrolysis reaction was carried out at room temperature for 4 hours. The reaction mixture was acidified by 5% citric acid and extracted with 100 mL EtOAc, and followed by washing with water 2×20 ml, and brine 2×20 ml, respectively. The organic phase was dried over anhydrous $Na_2SO_4$ and then

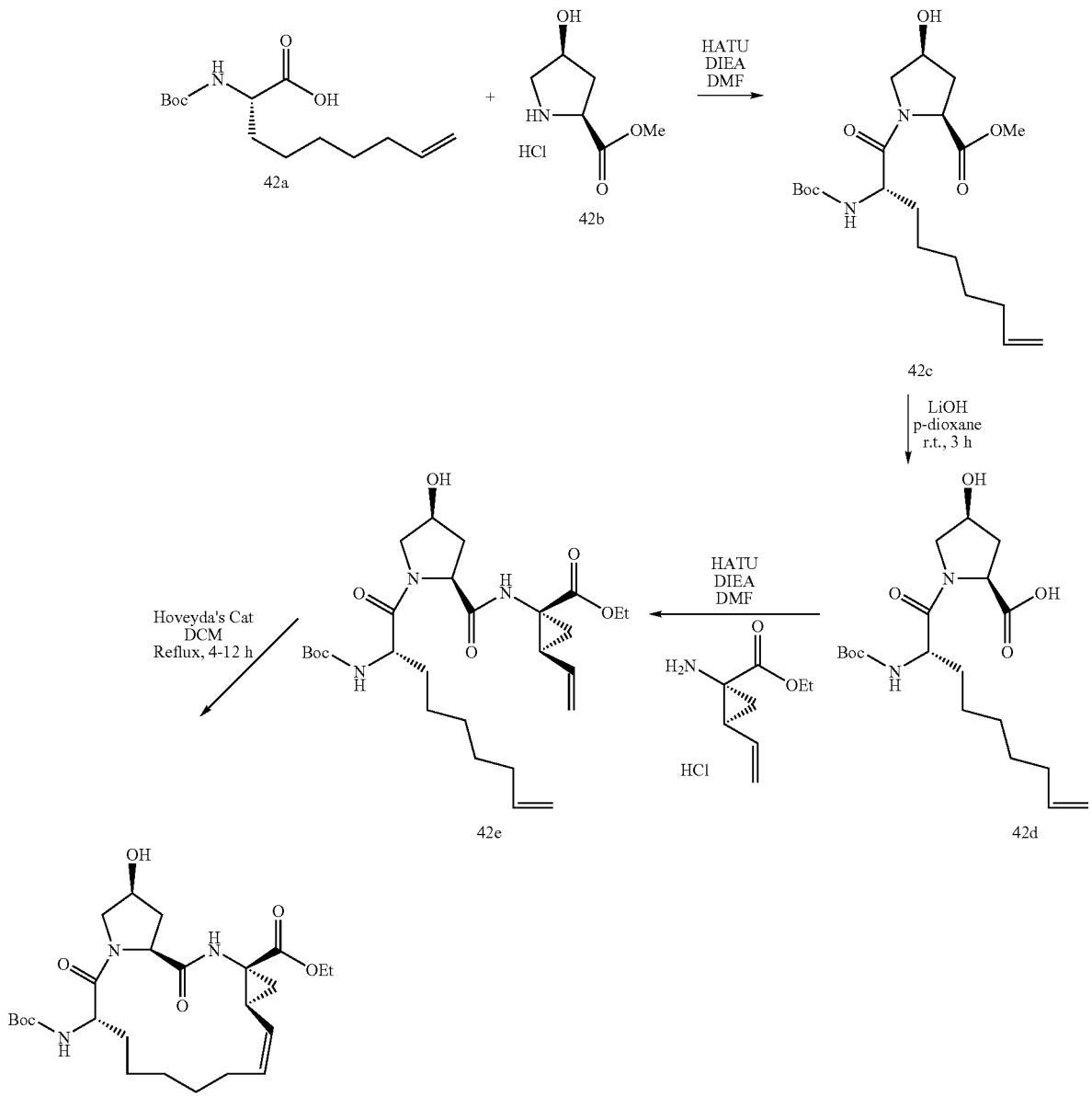

To a solution of Boc-L-2-amino-8-nonenoic acid 42a (1.36 g, 5 mol) and the commercially available cis-L-hydroxyproline methyl ester 42b (1.09 g, 6 mmol) in 15 ml DMF, was added DIEA (4 ml, 4eq.) and HATU (4 g, 2eq). The coupling was carried out at 0° C. over a period of 1 hour. The reaction mixture was diluted with 100 mL EtOAc, and followed by washing with 5% citric acid 2×20 ml, water 2×20 ml, 1M $NaHCO_3$ 4×20 ml and brine 2×10 ml, respectively. The organic phase was dried over anhydrous $Na_2SO_4$ and then was evaporated, affording the dipeptide 42c (1.91 g, 95.8%) that was identified by HPLC (Retention time=8.9 min, 30-70%, 90% B), and MS (found 421.37, M+$Na^+$).

removed in vacuum, yielding the free carboxylic acid compound 42d (1.79 g, 97%), which was used for next step synthesis without need for further purification.

To a solution of the free acid obtained above (1.77, 4.64 mmol) in 5 ml DMF, D-β-vinyl cyclopropane amino acid ethyl ester (0.95 g, 5 mmol), DIEA (4 ml, 4eq.) and HATU (4 g, 2eq) were added. The coupling was carried out at 0° C. over a period of 5 hours. The reaction mixture was diluted with 80 mL EtOAc, and followed by washing with 5% citric acid 2×20 ml, water 2×20 ml, 1M $NaHCO_3$ 4×20 ml and brine 2×10 ml, respectively. The organic phase was dried over anhydrous $Na_2SO_4$ and then evaporated. The residue was purified by silica gel flash chromatography using different ratios of hexanes:EtOAc as elution phase (5:1→3:1→1:1→1:2→1:5). The linear tripeptide 42e was isolated as an oil after removal of the elution solvents (1.59 g, 65.4%), identified by HPLC (Retention time=11.43 min) and MS (found 544.84, M+Na+).

A solution of the linear tripeptide 42e (1.51 g, 2.89 mmol) in 200 ml dry DCM was deoxygenated by bubbling $N_2$. Hoveyda's 1$^{st}$ generation catalyst (5 mol % eq.) was then added as solid. The reaction was refluxed under $N_2$ atmosphere 12 hours. The solvent was evaporated and the residue was purified by silica gel flash chromatography using different ratios of hexanes:EtOAc as elution phase (9:1→5:1→3:1→1:1→1:2→1:5). The cyclic peptide precursor was isolated as a white powder after removal of the elution solvents (1.24 g, 87%), identified by HPLC (Retention time=7.84 min, 30-70%, 90%B), and MS (found 516.28, M+Na+).

(2S,6S,13aS,14aR,16aS,Z)-ethyl 2-(4-bromophenylsulfonyloxy)-6-(tert-butoxycarbonylamino)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate

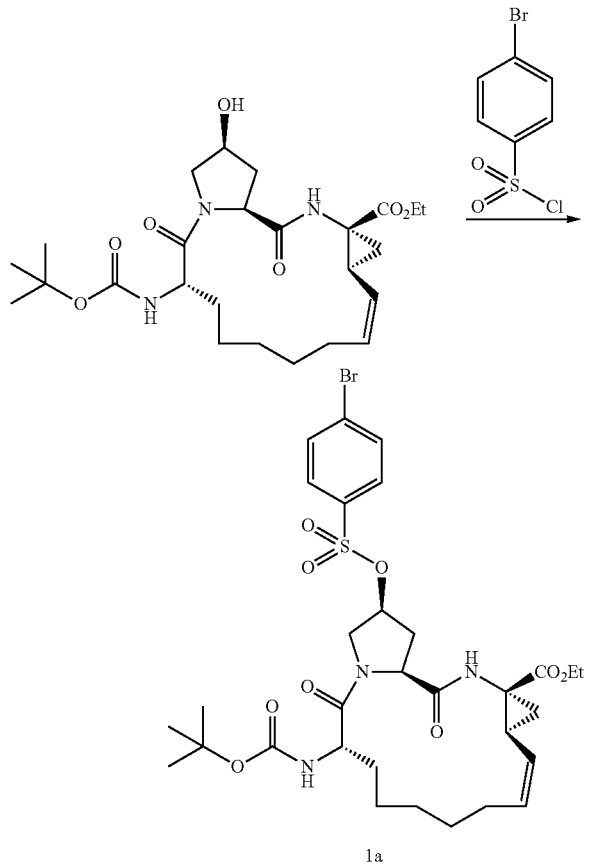

1a

A solution of (2S,6S,13aS,14aR,16aS,Z)-ethyl 6-(tert-butoxycarbonylamino)-2-hydroxy-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxylate (22.1 g, 44.8 mmol) and DABCO (8.5 g, 76.7 mmol) in toluene (88 mL) was stirred at room temperature. To this solution was added a solution of 4-bromobenzene-1-sulfonyl chloride 17.2 g, 67.2 mmol) in toluene (44 mL). After the addition was complete the reaction mixture was quenched with 10% aqueous sodium carbonate (110 mL) and the mixture stirred for 15 min. Tetrahydrofuran (44 mL) was added and the mixture was washed with 0.5 M HCl, water, and then saturated aqueous sodium chloride. The organic layer was dried over anhydrous magnesium sulfate, filtered, and evaporated under reduced pressure and dried to provide the title compound (27.7 g, 87% yield), which was used without further purification.

Example 56

Measurement of Potency of Inhibition with Purified NS3 Protease Enzyme

The activity of recombinant HCV NS3 proteases derived from isolates representing genotypes 1, 2, 3 or 4 is measured by cleavage of the following peptide substrate:

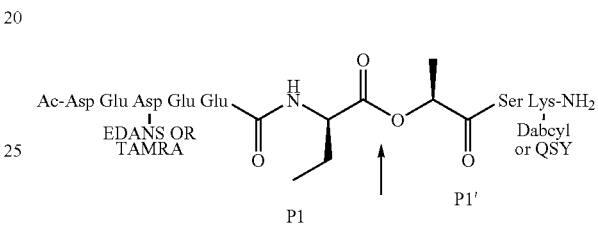

The substrate is labeled with a fluor and a fluorescence quencher. Cleavage results in release of the quencher and an increase in fluorescence. NS3 protease is incubated with a dilution series of inhibitor in 150 mM NaCl, 10% Glycerol, 5 mM DTT, with or without 0.01% dodecyl maltoside for either 30 minutes or 300 minutes. Substrate is added at a concentration of 5 uM to initiate the reaction, and fluorescence is measured at 2 minute intervals for 30 minutes. Enzyme concentrations range from 10 to 100 nM in the absence of detergent, or 10-fold lower in the presence of detergent. Substrate peptides are labeled with either EDANS and DABCYL (excitation 355 nm, emission 485 nm) or TAMRA and QSY (excitation 544 nm, emission 590 nm). For routine IC50 determination, 3-fold serial dilutions starting with initial concentrations of 100 μM, 200 μM, or 2 mM are used. For compounds with $K_i$ values approaching or lower than the enzyme concentration, a tight-binding calculation format is used, with 24 dilutions of inhibitor covering a range of 0 to 100 nM inhibitor. $K_i$ values are calculated using the tight binding assay format, according to the following equation: $V=A\{[(K+I-E)^2+4KE])^{1/2}-(K+I-E)\}$, where I=total inhibitor concentration, E=active enzyme concentration, K=apparent $K_i$ value and A=[$k_{cat}$)S/2][$K_m$=(S)].

Replicon Cell Lines

Two subgenomic replicon cell lines can be used for compound characterization in cell culture: one derived from genotype 1a and one derived from genotype 1b. Both replicon constructs are bicistronic subgenomic replicons essentially similar to those described by Bartenschlager and coworkers (Lohmann et al., *Science* (1999) 285(5424):110-113). The genotype 1a replicon construct contains the NS3-NS5B coding region derived from the H77 strain of HCV (1a-H77) (Blight et al., *J Virol* (2003) 77(5):3181-3190). The first cistron of the construct consists of the first 36 nucleotides of the HCV 1a-H77 core gene fused to a firefly luciferase reporter and a neomycin phosphotransferase (Neo) selectable marker. The luciferase and Neo coding regions are separated by the FMDV 2a protease. The second cistron contains the NS3-

NS5B coding region derived from 1a-H77 with the addition of adaptive mutations E1202G in NS3, K1691R in NS4A, and K2040R and S2204I in NS5A. The 1b-Con-1 replicon construct is identical to the 1a-H77 replicon, except that the 5' and 3' NTRs and the NS3-NS5B coding region can be derived from the 1b-Con-1 strain (Blight et al., *Science* (2000) 290 (5498):1972-1974), and the adaptive mutations are E1202G and T1280I in NS3 and S2204I in NS5A.

Replicon Compound Testing

Replicon cell lines can be maintained in Dulbecco's modified Eagles medium (DMEM) containing 100 IU/ml penicillin, 100 mg/ml streptomycin (Invitrogen), 200 mg/ml G418 (Invitrogen) and 10% (v/v) fetal bovine serum (FBS). Replicon-containing cells can be seeded into 96 well plates at a density of 5000 cells per well in 100 µl DMEM containing 5% FBS. The next day, the compound can be initially diluted in dimethyl sulfoxide (DMSO) to generate a 200× stock of the inhibitor in a series of 8 half-log dilutions. The dilution series can then be diluted 100-fold in the medium containing 5% FBS. One hundred microliters of medium with the inhibitor can be added to each well of the overnight cell culture plate already containing 100 µl of DMEM with 5% FBS. In assays where the protein binding effect on inhibitor potency is assessed, the medium from the overnight cell culture plates can be replaced with 200 µl DMEM containing 40% human plasma (Innovative Research) plus 5% FBS as well as compound. The cells can be grown for 4 days in tissue culture incubators. The inhibitory effects of compounds against the replicons can be determined by measuring either the level of luciferase or HCV RNA. The luciferase assay can be conducted using a Luciferase Assay System kit (Promega) following the manufacturer's instructions. Briefly, the cell culture medium is removed and wells are washed with 200 µl of phosphate-buffered saline. To each well Passive Lysis buffer (Promega, WI) is added and the plates are incubated for 30 min with rocking to lyse the cells. Luciferin solution (50 Promega) is added, and luciferase activity is measured with a Vktor II luminometer (Perkin-Elmer). To determine HCV RNA levels, RNA extractions can be performed using the CellsDirect kit (Invitrogen), and the HCV RNA copy number can be measured using the SuperScript III Platinum One-Step qRT-PCR system (Invitrogen) and primers specific to the HCV 5' nontranslated region. Cytotoxicity can be determined by the 3-[4,5-dimethythiazol-2-yl]-2,5-diphenyltetrazolium bromide (MTT) colorimetric assay as follows. Replicon cells is plated in 96-well plates (4000 cells per well), the next day compound dilutions are added as in the activity assay, and the cells are grown in the presence of the inhibitors for 4 days. The MTT solution is diluted in DMEM containing 5% FBS and 60 µl of the solution is added to the cells. After 4 hrs, the cells are solubilized by the addition of 30 µl SDS (20% in 0.02 N HCl). The plates are incubated overnight and the optical density can be measured at 570 nm. To determine compounds' $EC_{50}$ and $TD_{50}$, luciferase, RNA inhibition and MTT data can be analyzed using the GraphPad Prism 4 software (equation: sigmoidal dose-response–variable slope).

Mutants in Transient Replicons

Mutations detected in resistance selection studies can be introduced into wild type transient replicon constructs based on genotypes 1a-H77 and 1b-N. Both replicons are bicistronic sub-genomic constructs containing a firefly luciferase reporter similar to those described above, but they do not contain a Neo selectable marker and are therefore only suitable for transient replication assays. The 1a-H77 replicon for transient assays further differs from the replicon in the stable cell line in that it contains NS2 through NS5B in the second cistron. The 1b-N strain replicon contains NS3 through NS5B in the second cistron, with adaptive mutations E1202G in NS3 and S2204I in NS5A. Mutagenesis can be performed using the Stratagene QuikChange XL II site-directed mutagenesis kit. Mutants' sequences can be confirmed, plasmids can be linearized with Xba I restriction enzyme and used as template for in vitro transcription reactions to make mutant replicon RNA for transient transfections. In vitro transcription can be performed with the T7 Megascript kit (Ambion).

Transient replicon transfections can be performed essentially as described by Mo et al. (*Antimicrob Agents Chemother* (2005) 49(10):4305-4314) with slight modifications. Fifteen micrograms of template RNA can be used to electroporate $3×10^6$ cells in a 200 µl volume in a 0.2 cm cuvette. The cells used for transient transfections can be Huh7 cells obtained by curing replicon-containing cells with IFN (Mo et al., supra). Electroporation can be done with a Gene Pulser II (Bio-Rad, CA) at 480V and 25 µF, using two manual pulses. Transfected cells can be diluted to $7.5×10^4$ cells/ml and plated in 96 well plates at $7.5×10^3$ cells per well in DMEM with 5% FBS and 100 IU/ml penicillin, 100 mg/ml streptomycin (Invitrogen). Four hours post-transfection, one plate is harvested for luciferase measurement; this plate may provide a measure of the amount of input RNA that can be translated, and thus of transfection efficiency. To the remaining plates, test compound serial dilutions in DMSO can be added (0.5% DMSO final concentration), and plates are incubated for 4 days.

Exemplary compounds of the present invention were tested for their anti-HCV activities. Many of the compounds tested showed unexpected anti-HCV activities, including excellent activities in biochemical assays against HCV proteases representing various HCV genotypes, superior activities in standard HCV replicon assays including activity against 1a-H77 and 1b-con1 HCV strains in the absence or presence of 40% human plasma, and/or excellent activities in transient replicon assays against drug-resistant mutants in a number of different HCV genetic backgrounds.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Those skilled in the art will recognize, or be able to ascertain using no more than routine experimentation, many equivalents of the specific embodiments of the invention described herein. Such equivalents are intended with be encompassed by the following claims.

What is claimed:

1. A compound or a pharmaceutically acceptable salt thereof, selected from the following:
   (24) tert-butyl (2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate;
   (25) (2R,6S,13aS,14aR,16aS,Z)-N-(cyclopropylsulfonyl)-5,16-dioxo-2-(phenanthridin-6-yloxy)-6-(pyrazine-2-carboxamido)-1,2,3,5,6,7,8,9,10,11,13a,14,14a, 15,16,16a-hexadecahydrocyclopropa[e]pyrrolo[1,2-a] [1,4]diazacyclopentadecine-14a-carboxamide;
   (26) Cyclopentyl (2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16, 16a-hexadecahydrocyclopropa[e]pyrrolo[1,2-a][1,4]diazacyclopentadecin-6-ylcarbamate;

(27) (2R,6S,13aS,14aR,16aS,Z)-N-(cyclopropylsulfonyl)-6-(5-methyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(28) N-((2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide;

(29) (2R,6S,13aS,14aR,16aS,Z)-N-(cyclopropylsulfonyl)-6-(5-methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(30) N-((2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo [1,2-a][1,4]diazacyclopentadecin-6-yl)thiazole-5-carboxamide;

(31) (2R,6S,13aS,14aR,16aS,Z)-N-(cyclopropylsulfonyl)-6-(2-fluorobenzamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(32) (2R,6S,13aS,14aR,16aS,Z)-N-(cyclopropylsulfonyl)-5,16-dioxo-2-(phenanthridin-6-yloxy)-6-(pyridazine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(33) (2R,6S,13aS,14aR,16aS,Z)-N-(cyclopropylsulfonyl)-5,16-dioxo-2-(phenanthridin-6-yloxy)-6-(pyrimidine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(34) (2R,6S,13aS,14aR,16aS ,Z)-N-(cyclopropylsulfonyl)-6-(1-methyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(35) (2R,6S,13aS,14aR,16aS,Z)-N-(cyclopropylsulfonyl)-6-(2-hydroxy-2-methylpropanamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(36) (2R,6S,13aS,14aR,16aS,Z)-N-(cyclopropylsulfonyl)-6-(1,5-dimethyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide;

(37) Cyclopentyl (2R,6S,13aS,14aR,16aS,Z)-14a-(cyclopropylsulfonylcarbamoyl)-2-(2-fluorophenanthridin-6-yloxy)-5,16-dioxo-1,2,3,5,6,7,8,9,10,11,13a, 14,14a,15,16,16a-hexadecahydrocyclopropa[e]pyrrolo [1,2-a][1,4]diazacyclopentadecin-6-ylcarbamate;

(38) tert-Butyl (2R,6S,13aS,14aR,16aS,Z)-14a-(cyclopropylsulfonylcarbamoyl)-2-(2,9-difluorophenanthridin-6-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecin-6-ylcarbamate;

(39) tert-butyl (2R,6S,13aR,14aR,16aS)-14a-(cyclopropylsulfonylcarbamoyl)-5,16-dioxo-2-(phenanthridin-6-yloxy)octadecahydrocyclopropa[e]pyrrolo [1,2-a][1,4]diazacyclopentadecin-6-ylcarbamate;

(40) Cyclopentyl (2R,6S,13aR,14aR,16aS)-14a-(cyclopropylsulfonylcarbamoyl)-5,16-dioxo-2-(phenanthridin-6-yloxy)octadecahydrocyclopropa[e]pyrrolo[1,2-a][1,4]diazacyclopentadecin-6-ylcarbamate; and

(41) tert-Butyl (2R,6S,13aR,14aR,16aS)-5,16-dioxo-2-(phenanthridin-6-yloxy)-14a-(thiophen-2-ylsulfonylcarbamoyDoctadecahydrocyclopropa[e]pyrrolo[1,2-a][1,4]diazacyclopentadecin-6-ylcarbamate.

2. A pharmaceutical composition comprising a therapeutically effective amount of a compound of claim 1 or a pharmaceutically acceptable salt thereof, in combination with a pharmaceutically acceptable carrier or excipient.

3. A compound which is tert-butyl (2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-ylcarbamate, or a pharmaceutically acceptable salt thereof.

4. A compound which is (2R,6S,13aS,14aR,16aS,Z)-N-(cyclopropylsulfonyl)-5,16-dioxo-2-(phenanthridin-6-yloxy)-6-(pyrazine-2-carboxamido)-1,2,3,5,6,7,8,9,10,11,13a,14,14a,15,16,16a-hexadecahydrocyclopropa[e]pyrrolo[1,2-a][1,41diazacyclopentadecine-14a-carboxamide, or a pharmaceutically acceptable salt thereof.

5. A compound which is N-((2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)-5-methylisoxazole-3-carboxamide, or a pharmaceutically acceptable salt thereof.

6. A compound which is (2R,6S,13aS,14aR,16aS,Z)-N-(cyclopropylsulfonyl)-6-(5-methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo [1,2-a][1,4]diazacyclopentadecine-14a-carboxamide, or a pharmaceutically acceptable salt thereof.

7. A compound which is N-((2R,6S,13aS,14aR,16aS,Z)-14a-(cyclopropylsulfonylcarbamoyl)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecin-6-yl)thiazole-5-carboxamide, or a pharmaceutically acceptable salt thereof.

8. A compound which is (2R,6S,13aS,14aR,16aS,Z)-N-(cyclopropylsulfonyl)-5,16-dioxo-2-(phenanthridin-6-yloxy)-6-(pyridazine-4-carboxamido)-1,2,3,5,6,7,8,9,10,11,13a,14,14a,15,16,16a-hexadecahydrocyclopropa[e]pyrrolo[1,2-a][1,4]diazacyclopentadecine-14a-carboxamide, or a pharmaceutically acceptable salt thereof.

9. A compound which is (2R,6S,13aS,14aR,16aS,Z)-N-(cyclopropylsulfonyl)-6-(2-hydroxy-2-methylpropanamido)-5,16-dioxo-2-(phenanthridin-6-yloxy)-1,2,3,5,6,7,8,9,10,11,13a,14,14a,15,16,16a-hexadecahydrocyclopropa[e]pyrrolo [1,2-a][1,4]diazacyclopentadecine-14a-carboxamide, or a pharmaceutically acceptable salt thereof.

10. A compound which is (2R,6S,13aS,14aR,16aS,Z)-N-(cyclopropylsulfonyl)-6-(1,5-dimethyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide, or a pharmaceutically acceptable salt thereof.

11. A compound which is (2R,6S,13aS,14aR,16aS,Z)-N-(cyclopropylsulfonyl)-6-(5-methyl-1H-pyrazole-3-carboxamido)-5,16-dioxo-2-(phenanthridin-6-yloxy)-1,2,3,5,6,7,8,9,10,11,13a,14,14a,15,16,16a-hexadecahydrocyclopropa[e]

pyrrolo[1,2-a][1,4]diazacyclopentadecine-14a-carboxamide, or a pharmaceutically acceptable salt thereof.

12. A pharmaceutical composition comprising a therapeutically effective amount of the compound of claim 3 or a pharmaceutically acceptable salt thereof.

13. A pharmaceutical composition comprising a therapeutically effective amount of the compound of claim 4 or a pharmaceutically acceptable salt thereof.

14. A pharmaceutical composition comprising a therapeutically effective amount of the compound of claim 5 or a pharmaceutically acceptable salt thereof.

15. A pharmaceutical composition comprising a therapeutically effective amount of the compound of claim 6 or a pharmaceutically acceptable salt thereof.

16. A pharmaceutical composition comprising a therapeutically effective amount of the compound of claim 7 or a pharmaceutically acceptable salt thereof.

17. A pharmaceutical composition comprising a therapeutically effective amount of the compound of claim 8 or a pharmaceutically acceptable salt thereof.

18. A pharmaceutical composition comprising a therapeutically effective amount of the compound of claim 9 or a pharmaceutically acceptable salt thereof.

19. A pharmaceutical composition comprising a therapeutically effective amount of the compound of claim 10 or a pharmaceutically acceptable salt thereof.

20. A pharmaceutical composition comprising a therapeutically effective amount of the compound of claim 11 or a pharmaceutically acceptable salt thereof.

* * * * *